(12) United States Patent
Taft et al.

(10) Patent No.: US 8,399,007 B2
(45) Date of Patent: Mar. 19, 2013

(54) METHOD FOR FORMULATING A CONTROLLED-RELEASE PHARMACEUTICAL FORMULATION

(75) Inventors: David Taft, Atherton, CA (US); Stelios Tzannis, Newark, CA (US); Wei-Guo Dai, Sunnyvale, CA (US); Sandra Ottensmann, Mountain View, CA (US); Steven Bitler, Menlo Park, CA (US); Qiang Zheng, Palo Alto, CA (US); Adam Bell, Pacifica, CA (US)

(73) Assignee: Landec Corporation, Menlo Park, CA (US)

( * ) Notice: Subject to any disclaimer, the term of this patent is extended or adjusted under 35 U.S.C. 154(b) by 573 days.

(21) Appl. No.: 12/284,755

(22) Filed: Sep. 25, 2008

(65) Prior Publication Data

US 2009/0252777 A1 Oct. 8, 2009

Related U.S. Application Data

(63) Continuation-in-part of application No. 11/999,415, filed on Dec. 4, 2007.

(60) Provisional application No. 60/873,234, filed on Dec. 5, 2006, provisional application No. 61/005,400, filed on Dec. 4, 2007, provisional application No. 61/131,123, filed on Jun. 4, 2008, provisional application No. 61/131,716, filed on Jun. 10, 2008.

(51) Int. Cl.
*A61F 2/00* (2006.01)
*A61K 31/74* (2006.01)
*A61K 31/519* (2006.01)
*A61K 31/19* (2006.01)

(52) U.S. Cl. ........... 424/423; 424/78.17; 514/259.41; 514/567

(58) Field of Classification Search ................ None
See application file for complete search history.

(56) References Cited

U.S. PATENT DOCUMENTS

| | | |
|---|---|---|
| 3,608,549 A | 9/1971 | Merrill |
| 4,558,690 A | 12/1985 | Joyce |
| 4,830,855 A | 5/1989 | Stewart |
| 5,008,115 A * | 4/1991 | Lee et al. .............. 424/486 |
| 5,120,349 A | 6/1992 | Stewart |
| 5,129,180 A | 7/1992 | Stewart |
| 5,143,730 A | 9/1992 | Fues et al. |
| 5,156,911 A | 10/1992 | Stewart |
| 5,213,808 A | 5/1993 | Bar-Shalom et al. |
| 5,308,623 A | 5/1994 | Fues et al. |
| 5,384,333 A | 1/1995 | Davis et al. |
| 5,387,450 A * | 2/1995 | Stewart .................. 428/40.4 |
| 5,411,739 A * | 5/1995 | Jaeger et al. .............. 424/448 |
| 5,412,035 A | 5/1995 | Schmitt et al. |
| 5,429,654 A | 7/1995 | Swarup |
| 5,469,867 A | 11/1995 | Schmitt |
| 5,514,670 A * | 5/1996 | Friedman et al. .......... 424/185.1 |
| 5,662,711 A | 9/1997 | Douglas |
| 5,665,822 A * | 9/1997 | Bitler et al. .............. 525/92 C |
| 5,687,718 A | 11/1997 | Fischer et al. |
| 5,725,881 A | 3/1998 | Buchholz et al. |
| 5,783,302 A | 7/1998 | Bitler |
| 5,826,584 A | 10/1998 | Schmitt |
| 5,852,117 A | 12/1998 | Schoenberg et al. |
| 5,895,404 A | 4/1999 | Ruiz |
| 5,945,457 A | 8/1999 | Plate et al. |
| 6,001,395 A | 12/1999 | Coombes et al. |
| 6,004,549 A | 12/1999 | Reichert et al. |
| 6,174,546 B1 * | 1/2001 | Therriault et al. ............ 424/448 |
| 6,199,318 B1 | 3/2001 | Stewart |
| 6,214,901 B1 | 4/2001 | Chudzik |
| 6,221,368 B1 * | 4/2001 | Breitenbach et al. ......... 424/400 |
| 6,224,793 B1 * | 5/2001 | Hoffman et al. .............. 264/4.1 |
| 6,255,367 B1 | 7/2001 | Bitler |
| 6,297,337 B1 | 10/2001 | Marchant et al. |
| 6,319,521 B1 | 11/2001 | Randolph |
| 6,344,035 B1 | 2/2002 | Cudzik |
| 6,352,667 B1 | 3/2002 | English |
| 6,423,345 B2 | 7/2002 | Berstein et al. |
| 6,469,133 B2 | 10/2002 | Baker et al. |
| 6,524,274 B1 | 2/2003 | Rosenthal |
| 6,528,080 B2 | 3/2003 | Dunn et al. |
| 6,540,984 B2 | 4/2003 | Stewart |
| 6,569,128 B1 | 5/2003 | Christensen et al. |
| 6,576,254 B1 | 6/2003 | Uchegbu |
| 6,653,395 B1 | 11/2003 | Bergstrom et al. |
| 6,656,385 B2 | 12/2003 | Lynch |
| 6,657,042 B2 | 12/2003 | Rafler et al. |
| 6,699,952 B2 | 3/2004 | Chaikof |
| 6,730,322 B1 | 5/2004 | Berstein et al. |
| 6,780,930 B2 | 8/2004 | Lewis |
| 6,831,116 B2 | 12/2004 | Bitler |
| 6,858,634 B2 | 2/2005 | Asrar et al. |
| 6,866,860 B2 | 3/2005 | Nathan |
| 6,887,960 B2 | 5/2005 | Parker et al. |
| 6,890,583 B2 | 5/2005 | Chudzik |
| 6,951,642 B2 | 10/2005 | Scholz et al. |
| 6,964,778 B1 | 11/2005 | Hui |
| 6,967,234 B2 | 11/2005 | Nathan |

(Continued)

FOREIGN PATENT DOCUMENTS

| | | |
|---|---|---|
| AR | P 070104879 | 5/2009 |
| EP | 0064379 A1 | 11/1982 |
| EP | 0568345 A1 | 11/1993 |
| EP | 0778304 | 6/1997 |
| EP | 1348451 A1 | 10/2003 |

(Continued)

OTHER PUBLICATIONS

Lee, J. et al, "Thermosenstive Permeation From Side-Chain Crystalline Ionomers", Journal of Polymer Science: Part B: Polymer Physics, vol. 38, pp. 823-830; 2000.

(Continued)

*Primary Examiner* — Michael G Hartley
*Assistant Examiner* — Lance Rider
(74) *Attorney, Agent, or Firm* — James S. McDonald; Tim Richardson

(57) ABSTRACT

Methods for making formulations of drugs and crystalline side chain polymers which formulations provide controlled and/or sustained release drug formulations.

49 Claims, 7 Drawing Sheets

U.S. PATENT DOCUMENTS

| | | | |
|---|---|---|---|
| 6,989,417 | B2 | 1/2006 | Bitler et al. |
| 7,008,667 | B2 | 3/2006 | Chudnik |
| 7,030,082 | B2 | 4/2006 | Soltero et al. |
| 7,083,572 | B2 | 8/2006 | Unger et al. |
| 7,220,430 | B2 | 5/2007 | Ishibashi et al. |
| 2002/0106406 | A1 | 8/2002 | McHugh et al. |
| 2002/0114827 | A1 | 8/2002 | Zhang |
| 2002/0161437 | A1 | 10/2002 | Zhou et al. |
| 2003/0082217 | A1 | 5/2003 | Afriat |
| 2003/0224974 | A1 | 12/2003 | Bolotin |
| 2004/0052746 | A1 | 3/2004 | Tamareselvy |
| 2004/0117006 | A1 | 6/2004 | Lewis et al. |
| 2004/0208844 | A1 | 10/2004 | Ignatious |
| 2004/0236013 | A1 | 11/2004 | Lewis |
| 2004/0254419 | A1 | 12/2004 | Wang et al. |
| 2005/0019923 | A1 | 1/2005 | Uchegbu et al. |
| 2005/0112186 | A1* | 5/2005 | Devore et al. ............... 424/450 |
| 2005/0169977 | A1 | 8/2005 | Kanios et al. |
| 2005/0197251 | A1 | 9/2005 | Ding et al. |
| 2005/0249697 | A1 | 11/2005 | Uhrich et al. |
| 2005/0249799 | A1 | 11/2005 | Jacob |
| 2006/0018948 | A1 | 1/2006 | Guire |
| 2006/0024361 | A1 | 2/2006 | Odidi |
| 2006/0034891 | A1 | 2/2006 | Lawin et al. |
| 2006/0148982 | A1 | 7/2006 | Uchegbu et al. |
| 2006/0167116 | A1 | 7/2006 | Uchegbu et al. |
| 2006/0286064 | A1 | 12/2006 | Turnell et al. |
| 2006/0292222 | A1 | 12/2006 | Jonasse |
| 2007/0016284 | A1 | 1/2007 | Pacetti |
| 2007/0134310 | A1 | 6/2007 | Nedberge et al. |
| 2007/0142461 | A1 | 6/2007 | Baker et al. |
| 2007/0259584 | A1 | 11/2007 | Whitehouse |
| 2007/0023226 | A1 | 6/2008 | Schmitt |
| 2009/0124996 | A1 | 5/2009 | Krumme et al. |
| 2009/0177158 | A1 | 7/2009 | Krumme |
| 2009/0198183 | A1 | 8/2009 | Krumme |
| 2009/0240200 | A1 | 9/2009 | Krumme et al. |

FOREIGN PATENT DOCUMENTS

| | | |
|---|---|---|
| EP | 1430916 A1 | 6/2004 |
| EP | 1629835 A1 | 3/2006 |
| GB | 2160100 A | 12/1985 |
| GB | 2161819 A | 1/1986 |
| JP | 62042918 A | 2/1987 |
| JP | 3123730 A | 5/1991 |
| JP | 2002 138 033 A | 5/2002 |
| RU | 2092161 | 10/1997 |
| TW | 096141574 | 5/2008 |
| WO | WO 91/04015 A1 | 4/1991 |
| WO | WO 92/13901 | 8/1992 |
| WO | WO 94/07940 A1 | 4/1994 |
| WO | WO 96/18417 A1 | 6/1996 |
| WO | WO 99/36058 | 7/1999 |
| WO | WO 99/47543 A2 | 9/1999 |
| WO | WO 99/56731 | 11/1999 |
| WO | WO 01/54671 A1 | 8/2001 |
| WO | WO 01/87276 | 11/2001 |
| WO | WO 02/45685 A2 | 6/2002 |
| WO | WO 03/022323 A1 | 3/2003 |
| WO | WO 03/028653 | 4/2003 |
| WO | WO 03/033027 | 4/2003 |
| WO | WO 2004/024779 | 3/2004 |
| WO | WO 2004/026912 | 4/2004 |
| WO | WO 2004/052339 | 6/2004 |
| WO | WO 2005/051358 A1 | 6/2005 |
| WO | WO 2005/084639 | 9/2005 |
| WO | WO 2006/039152 | 4/2006 |
| WO | WO 2006/128471 A2 | 12/2006 |
| WO | PCT/US2007/023226 | 6/2008 |
| WO | WO 2008/066657 A2 | 6/2008 |

OTHER PUBLICATIONS

M. Dufresne et al.—Abstract—Preparation and characterization of water-soluble pH-sensitive nanocarriers for drug delivery Int. J. Pharmaceutics vol. 277, No. 1-2, 2004, pp. 81-90.

Emmanuel Roux et al. "Polymer based pH-sensitivecarriers as a means to improve the cytoplasmic delivery of drugs". Int. J. Pharmaceutics vol. 242, No. 1-2, 2002, pp. 25-36.

EPO examination report for corresponding European case.

Amsden, "Development of Biodegradable Injectable Thermoplastic Oligomers" Biomacromolecules 2004, vol. 5, pp. 637-642.

U.S. Appl. No. 60/856,430, filed Nov. 3, 2008, Schmitt.

U.S. Appl. No. 60/857,546, filed May 8, 2008, Schmitt.

U.S. Appl. No. 60/857,755, filed May 8, 2008, Krumme.

U.S. Appl. No. 60/964,066, filed Feb. 8, 2009, Krumme.

U.S. Appl. No. 60/993,541, filed Sep. 12, 2009, Krumme.

U.S. Appl. No. 61/016,223, filed Jun. 21, 2009, Krumme.

Mohr, J.M., et al., "Drug Delivery with Side Chain Crystallizable Polymer Blends", 1991; Proceedings of the 18th International Symposium on Controlled Release of Bioactive Materials, pp. 409-410; Controlled Release Society, U.S.A.

Mohr, J.M., et al, "Pulsatile Transdermal Drug Delivery", 1992; Proceedings of the 19th International Symposium on Controlled Release of Bioactive Materials, pp. 377-378; Controlled Release Society, U.S.A.

Brannon-Peppas, L., "Polymers in Controlled Drug Delivery", Medical Plastics and Biomaterials, p. 34, Nov. 1997.

Birnbaum, D., et al., "Microparticle Drug Delivery Systems" Drug Delivery Systems in Cancer Therapy, Chapter 6, pp. 117-135; Sep. 2003.

Du, J., et al., "pH Sensitive Vesicles Based on a Biocompatible Zwitterionic Diblock Copolymer", Journal of American Chemistry Society, vol. 127, #51, pp. 17982-17983; 2005.

Kaneko, T.; Miyazaki, T.; Yamaoka, K.; Katayama, Y.; Matsuda, A.; Gong, J.; and Osada, Y.; "Shape-Memory Gels with Multi-Stimuli Responses"; Proceedings of SPIE, vol. 3669, pp. 199-208, Smart Structures and Materials; May 1999: Electroactive Polymer Actuators and Devices.

Wei, J-S.; Zeng, H-B.; Liu, S-Q.; Wang, X-G.; Tay, E.H.; and Yang, Y-Y.; Temperature and pH Sensitive Core-Shell Nanoparticles Self-Assembled From Poly(N-Isopropylacrylamide-Co-Acrylic Acid-CO-Cholesteryl Acrylate) for Intracellular Delivery of Anticancer Drugs; Sep. 2005; Frontiers in Bioscience 10, pp. 3058-3067; Frontier in Bioscience, U.S.A.

Ng, C.C.; Cheng, Y-L.; Saville, B.A.; Thermoresponsive Polymer Membrane for the Local Delivery of Drugs; Summer 2001; Journal of Sexual and Reproductive Medicine, vol. 1 #1, pp. 21-27; Pulses Group Inc., Canada.

Luppi, B.; Cerchiara, T.; Bigucci, F.; Orienti, I.; and Zecchi, V.; pH-Sensitive Polymeric Physical-Mixture for Possible Site-Specific Delivery of Ibuprofen; Mar. 2003; European Journal of Pharmaceutics and Biopharmaceutics, 55, #2, pp. 199-202; Elsevier, Netherlands.

Bulmus, V.; Woodward, M.; Lin, L.; Murthy, N.; Stayton, P.; and Hoffman, A.; A New pH Responsive and Glutathione-Reactive, Endosomal Membrane Disruptive Polymeric Carrier for Intracellular Delivery of Biomolecular Drugs; Dec. 2003; Journal of Controlled Release, vol. 93, #2, pp. 105-120; Elsevier, Netherlands.

K.M. Scholsky and R.M. Fitch; Controlled Release of Pendant Bioactive Materials from Acrylic Polymer Colloids; 1986; Journal of Controlled Release, vol. 3, #1-4, pp. 87-102; Elsevier, Netherlands.

LaVan, D.A.; McGuire, T.; and Langer, R.; Small Scale Systems for In Vivo Drug Delivery; Oct. 2003; Nature Biotechnology, vol. 21, #10, pp. 1184-1191; Nature Publishing Group., U.K.

Schmidt, E.E.; Mohr, J.; and Stewart, R.F.; Side Chain Crystallizable Polymer Based Drug Delivery Phenomenon; 1991; in Proceedings of the 18th International Symposium on Controlled Release of Bioactive Materials, p. 134-135; Controlled Release Society, U.S.A.

Torchilin, V., "Structure and Design of Polymeric Surfactant-Based Drug Delivery Systems",Journal of Controlled Release, vol. 73, #2-3, pp. 137-172; Jun. 2001.

Boudreaux, C.J., et al., "Controlled Activity Polymers. XI Hydrolytic Release Studies of Hydrophilic Copolymers With Labile Esters of Model Allelopathic Phenols", Journal of Controlled Release, vol. 44, #2-3, pp. 185-194, Feb. 1997.

Loth, H., et al. "Methoxy-Polyethoxy Side-Chain Silastomers as Materials Controlling Drug Delivery by Diffusion Flux", Journal of Controlled Release, vol. 54, #3, pp. 273-282 Aug. 1998.

Yadav, S.K., et al., "Release Rates From Semi-Crystalline Polymer Microcapsules Formed By Interfacial Polycondensation", Journal of Membrane Science, vol. 125, #2, pp. 213-218; Mar. 1997.

Greene, L., "Side-Chain Crystallizable Polymers for Temperature-Activated Controlled Release", Polymeric Delivery Systems: Properties and Applications (ACS Symposium Series, No. 520), pp. 244-256, 1993.

Yu, L., et al., "A Subtle End-Group Effect on Macroscopic Physical Gelation of Triblock Copolymer Aqueous Solutions", Angew. Chem. Int. Ed. 2006, 45, 2232-2235.

Abayashinghe, N., et al., "Oligoethylene-End-Capped-Polylactides", Journal of Polymer Science: Part A: Polymer Chemistry, vol. 43, 5257-5266 (2005).

Mehvar, R., "Modulation of the Pharmacokinetics and Pharmacodynamics of Proteins by Polyethylene Glycol Conjugation", J. Pharm. Pharmaceut. Sci. 3(1):125-136, 2000.

Jiang, X., et al., ""Clickable" Polyglycolides: Tunable Synthons for Thermoresponsive, Degradable Polymers", Department of Chemistry, Michigan State University, East Lansing, MI, pp. 1-34, Date 2008.

Baker, G., et al., "New Polylactides from Hydroxyacids Derived from Renewable Sources". Polymer Preprints 2007, 48(2), 826.

Maruyama, S., et al., "A Synthetic Polymer, Poly(2-methacryloyloxyethyl phosphorylcholine-*co-n*-stearyl methacrylate), Stimulates Insulin Release form RINm5F Insulinoma Cells", Biosci. Biotechnol. Biochem., 68 (10), 2197-2200, 2004.

Pollino, J., et al., "Non-Covalent Side-Chain Polymers: Design Principles, Functionalization Strategies and Perspectives", Chem. Soc. Rev., 2005, 34, 193-207.

Roberts, M., et al., "Molecule Engineering Including Advanced PEGylation: Understanding the Full Potential", The Drug Delivery Companies Report Spring/Summer 2003, PharmaVentures, Ltd, 2003.

Ivan, B., et al., "New Nanophase Separated Intelligent Amphiphilic Conetworks and Gels", Macromolecular Symposia, Jul. 2005 vol. 227 (1), pp. 265-274, Wiley-VCH GmbH & Co. KgaA, Weinheim.

Shang, S., et al., "Comb-Like Ionomeric Copolymer: Itaconic Anhydride-co-Stearyl Methacrylate", ACS Polymer Preprints, 2007, vol. 48(2), pp. 871-872.

Davaran, S., et al., "Release of 5-Aminosalicylic Acid from Acrylic Type Polymeric Prodrugs Designed for Colon Drug Delivery", 1999; Journal of Controlled Release, 58, #3, pp. 279-287.

Bendix, Dieter, "Chemical Synthesis of Polyactide and its Copolymers for Medical Applications" 1998, Polymer Degradation and Stability, vol. 59, pp. 129-135; Elsevier Science Limited.

Mehta, Nozer M., "Oral Delivery and Recombinant Production of Peptide Hormones. Part I: Making Oral Delivery Possible" Jun. 2004 BIOPHARM International pp. 1-6.

Mehta, Nozer M., "Oral Delivery and Recombinant Production of Peptide Hormones. Part II: Recombinant Production of Therapeutic Peptides" Jul. 2004 BIOPHARM International pp. 7-9.

Morgan, V., "NOBEX: No Barriers" Overview. No date. File created Jun. 14, 2006; Nobex Corporation, Research Triangle Park, NC; 2 pp.

Quintana, A., et al., "Design and Function of a Dendrimer-Based Therapeutic Nanodevice Targeted to Tumor Cells Through the Folate Receptor" Pharmaceutical Research, vol. 19, #9, pp. 1310-1316; Sep. 2002.

Henry, C., "Cooking Cancer—Carbon Nanotubes and Near-Infrared Radiation Kill Cancer Cells by Heating" Chemical & Engineering News, vol. 83, #32, p. 16; 2005.

Yan, X., et al., "Cisplatin Delivery from Poly(acrylic acid-co-methyl methacrylate) Microparticles", Journal of Controlled Release, vol. 106, #1-2, pp. 198-208; Aug. 2005.

Nishino, S., et al. "Preparation and Interfacial Properties of a Novel Biodegradable Polymer Surfactant: Poly(ethylene oxide monooleate-*block*-DL-lactide)", Macromolecular Bioscience; vol. 5, pp. 1066-1073; 2005.

ANON. "Biodegradable Polymers: A Review" Environment and Plastics Industry Council (EPIC) Technical Report pp. 1-11; Nov. 24, 2000.

ANON. "What Are the Latest Drug Delivery Systems Made of?" Online Publication Science Scotland; The Royal Society of Edinburgh; Issue 2, pp. 9-10; Spring 2004.

Hadlington, S. "Special Delivery", "Chemistry World" (online edition, previously "Chemistry in Britain"), Royal Society of Chemistry, UK; No. 5, pp. 1-3; May 2003.

* cited by examiner

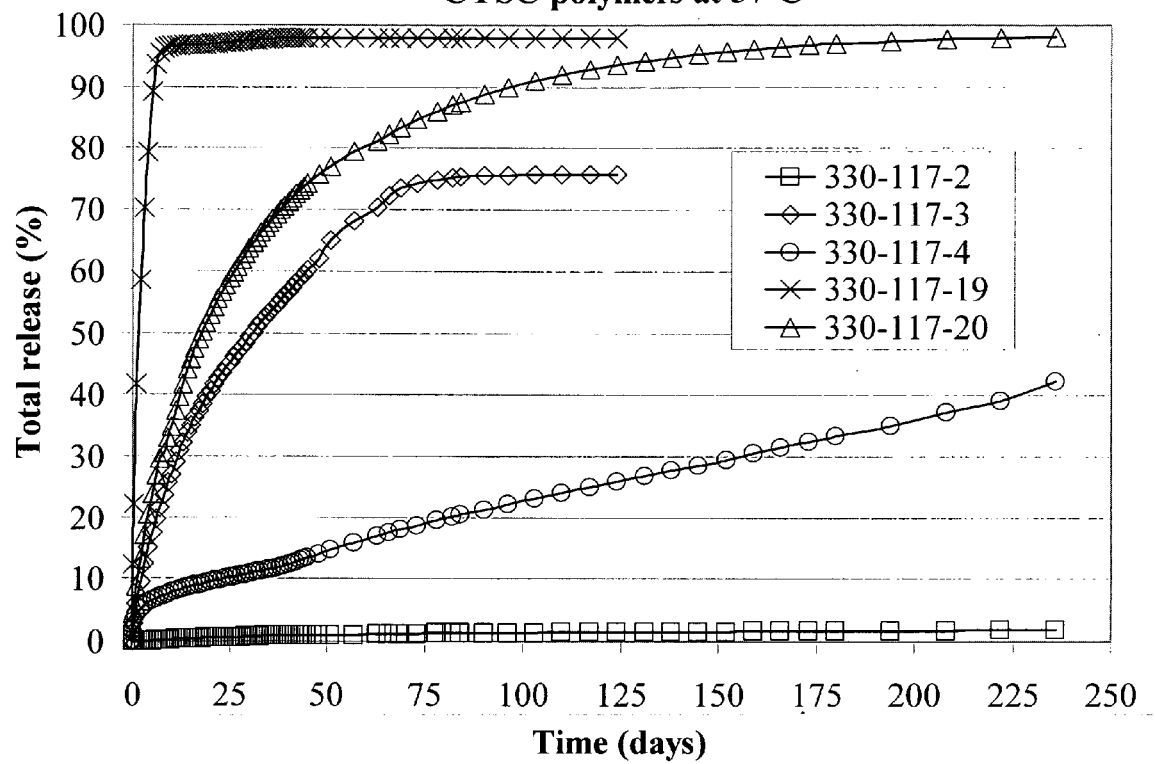
Figure J1. Cumulative release of risperidone from CYSC polymers at 37°C

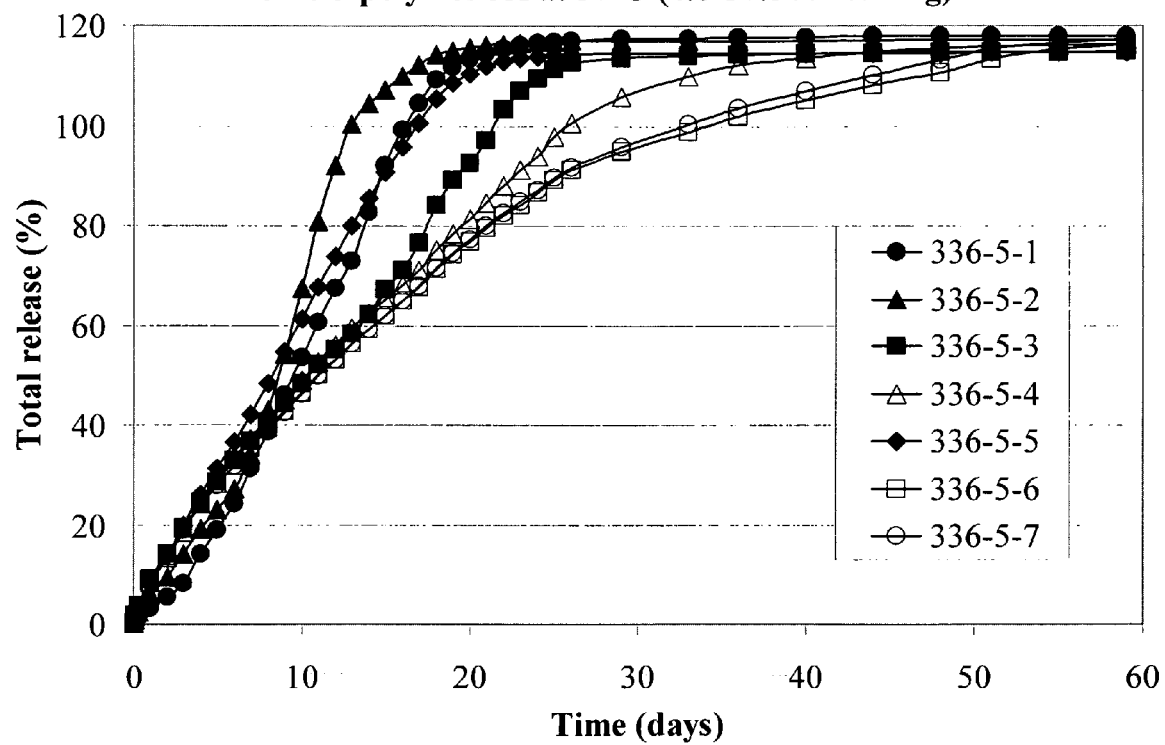
Figure K1. Cumulative release of risperidone from CYSC polymer 3A at 37°C (4.8-37.5% loading)

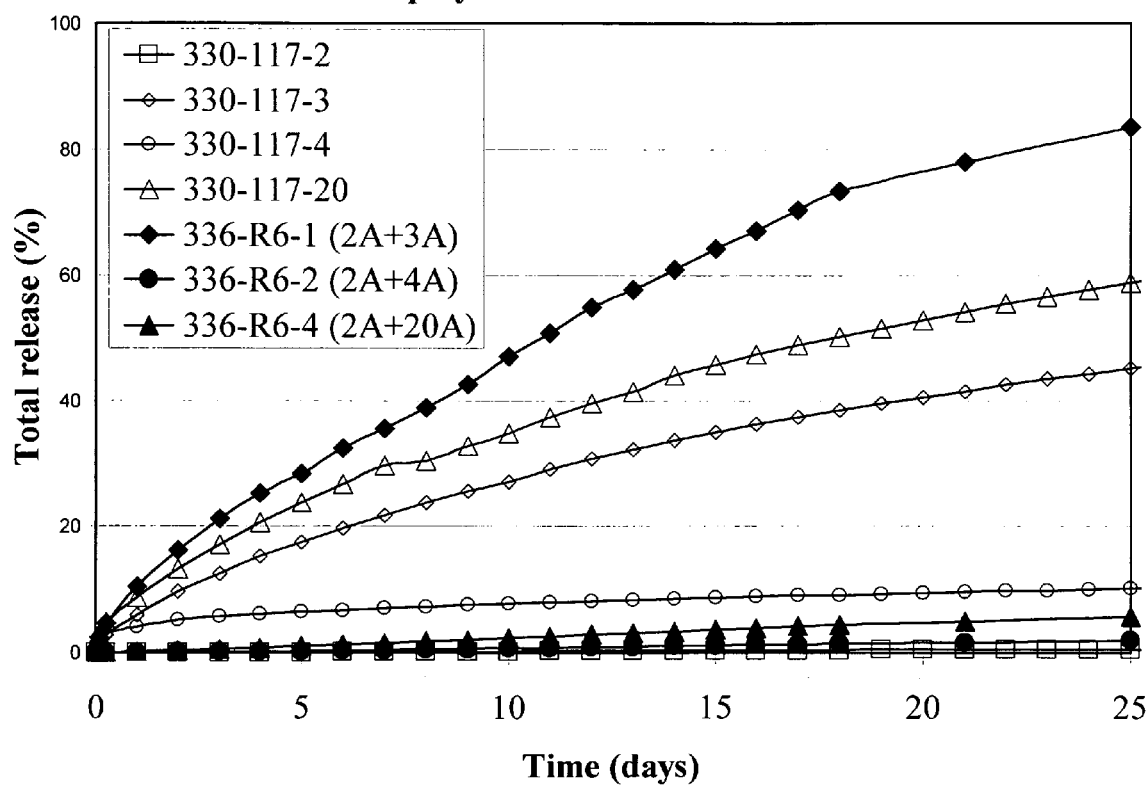
Figure L1. Cumulative release of risperidone from CYSC polymer mixtures at 37°C

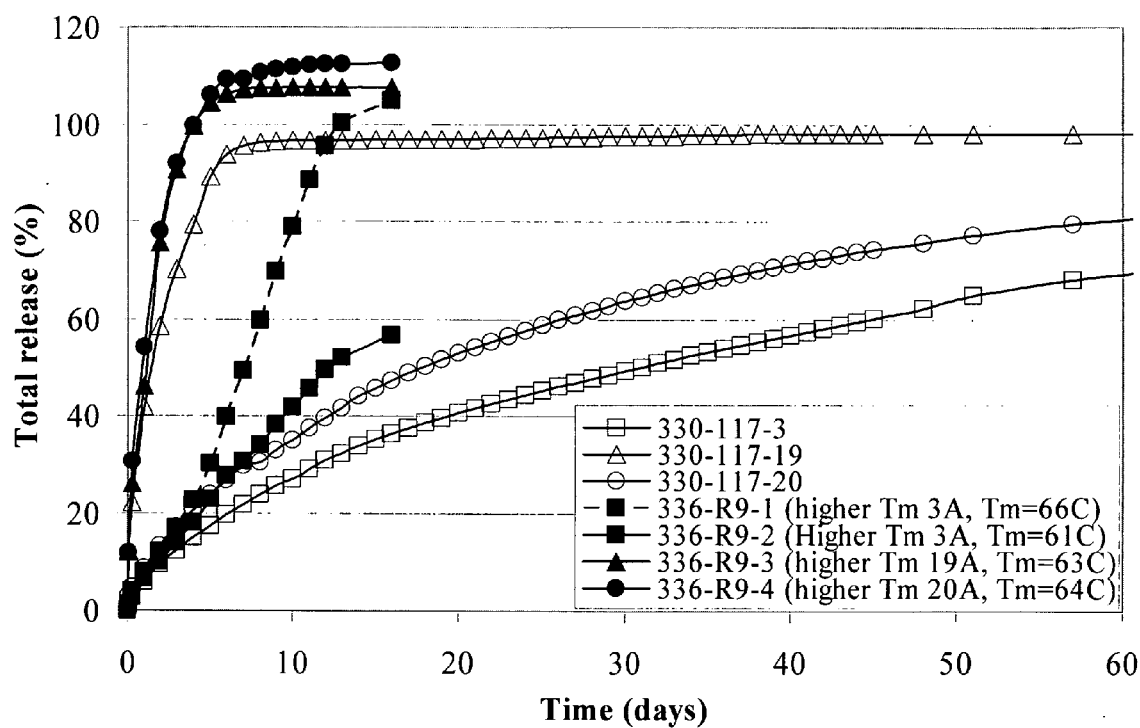
Figure M1. Cumulative release of risperidone from CYSC polymers with higher Tm at 37°C

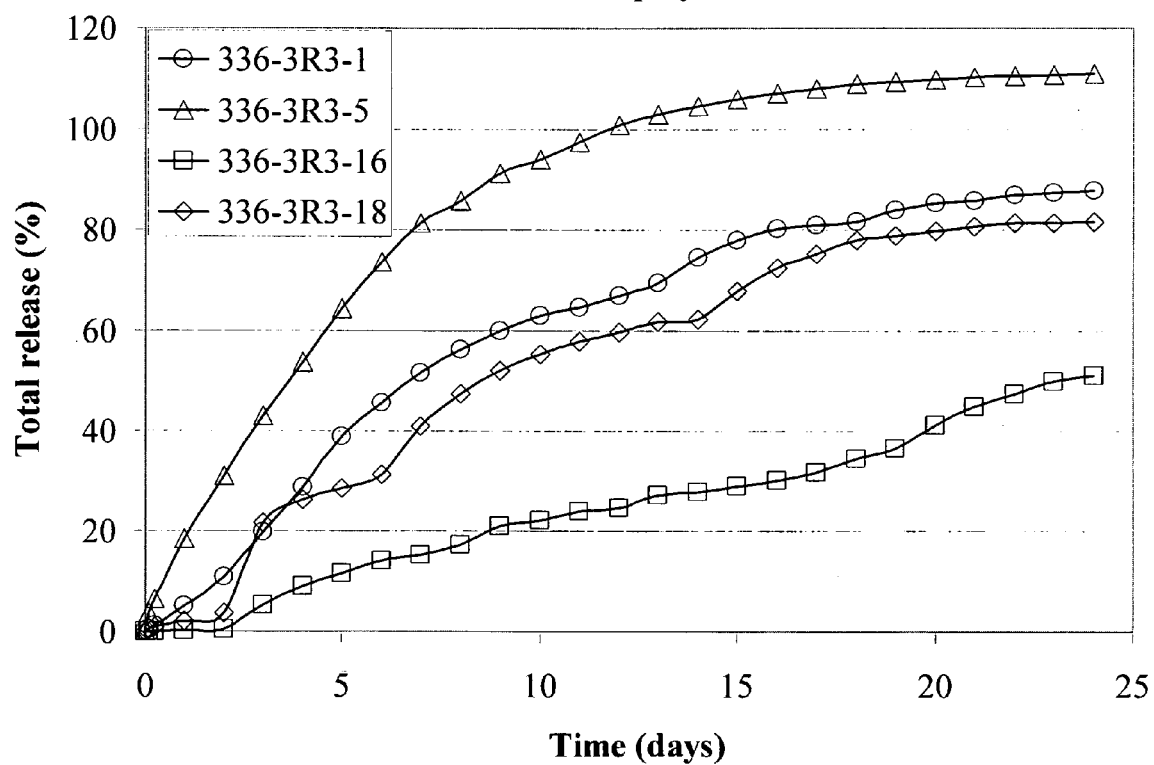
Figure N1. Cumulative release of risperidone from uniform 2 phase mixtures of CYSC polymers at 37°C

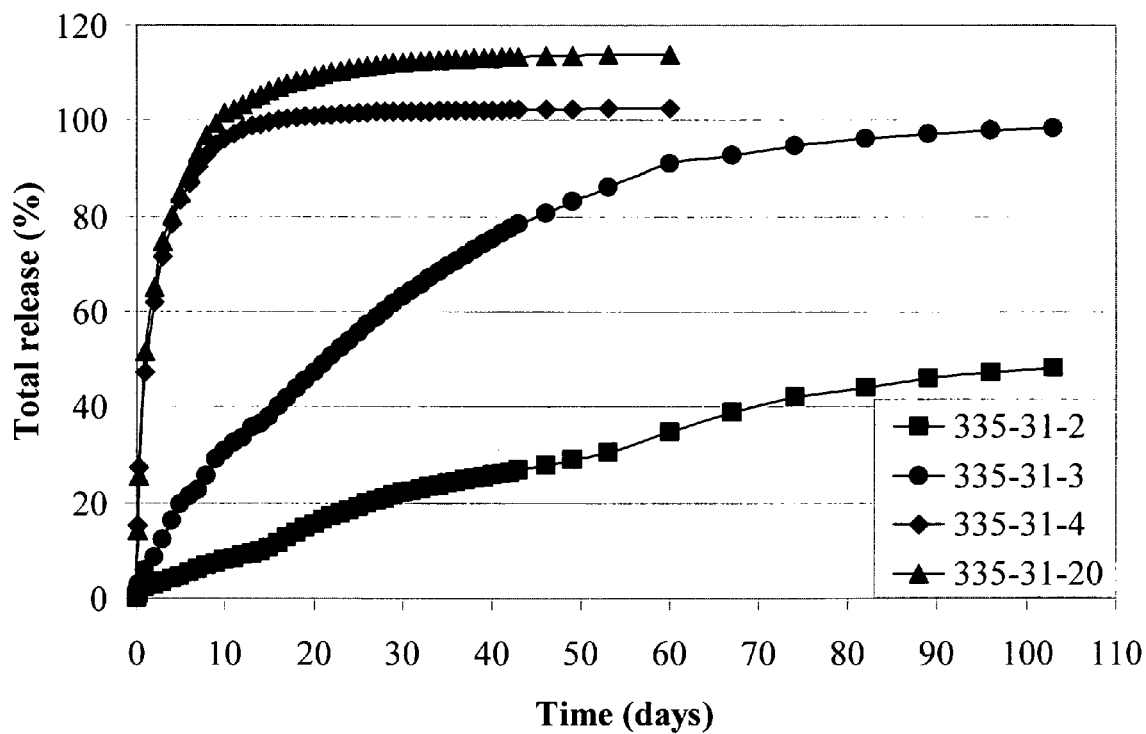
Figure O1. Cumulative release of risperidone from CYSC polymers in powder form at 37°C

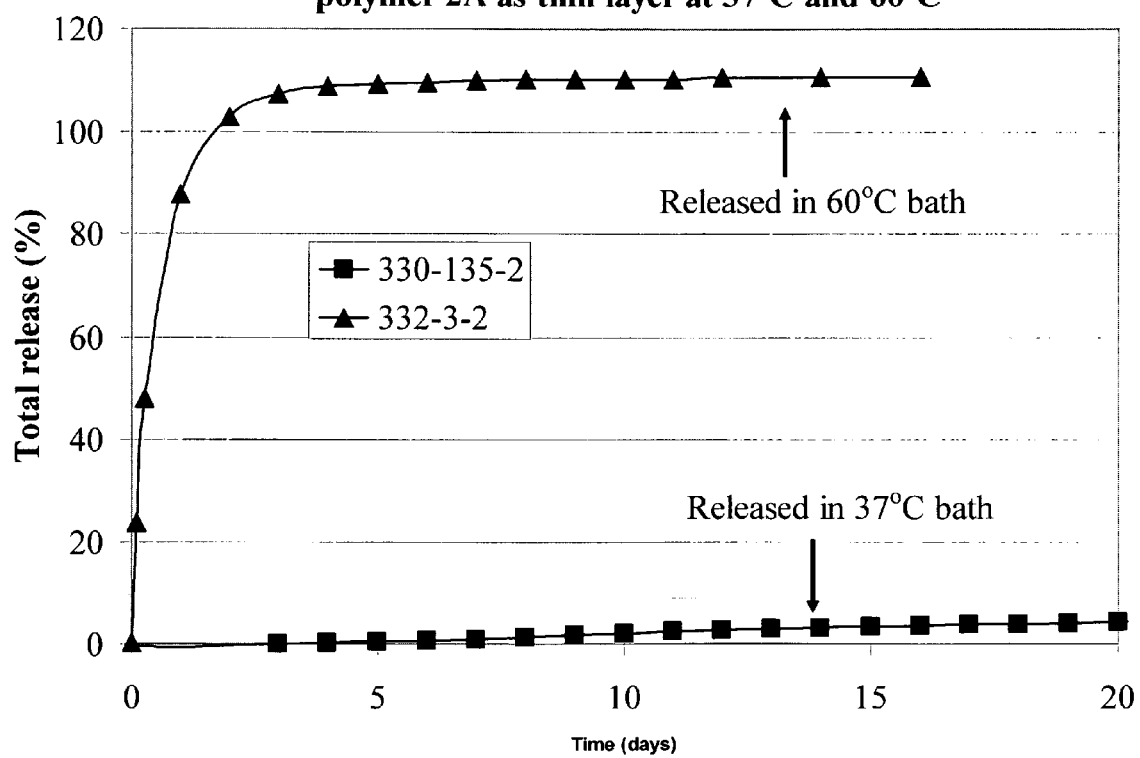
Figure P1. Cumulative release of risperidone from CYSC polymer 2A as thin layer at 37°C and 60°C

METHOD FOR FORMULATING A CONTROLLED-RELEASE PHARMACEUTICAL FORMULATION

CROSS-REFERENCE TO RELATED APPLICATION

This application is a continuation-in-part of pending U.S. application Ser. No. 11/999,415, filed Dec. 4, 2007, which claims priority from and the benefit of U.S. provisional Application No. 60/873,234, filed Dec. 5, 2006. This application also claims priority from and the benefit of U.S. provisional Application No. 61/005,400, filed Dec. 4, 2007, U.S. provisional Application No. 61/131,123, filed Jun. 4, 2008, and U.S. provisional Application No. 61/131,716, filed Jun. 10, 2008. This application is related to International Application No. PCT/US 2007/024909, filed Dec. 4, 2007, claiming priority from U.S. provisional Application No. 60/873,234, filed Dec. 5, 2006, and International Application No. PCT/US 2007/025032, filed Dec. 5, 2007, claiming priority from U.S. provisional Application No. 60/873,234, filed Dec. 5, 2007. The entire disclosure of each of those applications is incorporated herein by reference for all purposes.

FIELD OF THE INVENTION

This invention relates to polymeric systems for the delivery of bioactive materials.

BACKGROUND

Polymeric systems for the delivery of bioactive materials such as drugs are well known, but many inherent problems persist and there is a need for a controlled-release pharmaceutical formulation with high loading and precisely controlled drug release. The present invention addresses this need.

BRIEF DESCRIPTION OF THE DRAWINGS

The table below shows the correlation between the Example numbers in Tables 1A, 1B and 1C and the Sample numbers referred to elsewhere in the specification.

| Example No. | 1A | 2A | 3A | 4A | 5A | 6A | 7A |
|---|---|---|---|---|---|---|---|
| Sample No. | 328-133-1 | 326-1-1 | 326-2-1 | 326-3-1 | 326-5-1 | 327-1-1A | 327-39-1 |
| Example No. | 8A | 9A | 10A | 11A | 12A | 13A | 14A |
| Sample No. | 327-40-1 | 326-8-1A | 326-8-3 | 327-3-1B | 327-3-3B | 327-137-1 | 327-137-3 |
| Example No. | 15A | 16A | 17A | 18A | 19A | 20A | |
| Sample No. | 326-6-1 | 326-6-3 | 326-9-1 | 326-11-3 | 327-42-2 | 327-42-11 | |

FIG. J1 Cumulative release of Risperidone from CYSC polymer at 37° C.

FIG. K1 Cumulative release of Risperidone from CYSC polymer 3A at 37° C.

FIG. L1 Cumulative release of Risperidone from CYSC polymer at 37° C.

FIG. M1 Cumulative release of Risperidone from CYSC polymer with higher Tm at 37° C.

FIG. N1 Cumulative release of Risperidone from uniform 2 phase mixtures of CYSC polymer at 37° C.

FIG. O1 Cumulative release of Risperidone from CYSC polymer in powder form at 37° C.

FIG. P1 Cumulative release of Risperidone from CYSC polymer 2A as a thin layer at 37° C. and at 60° C.

SUMMARY OF THE INVENTION

Useful delivery of bioactive materials can be obtained through the association of bioactive materials with certain polymers which are referred to herein as CYSC (crystallizable side chain polymers) polymers as described herein.

The invention encompasses a method for making a drug formulation comprising a polymer and a drug distributed in the polymer, the polymer being a crystalline side chain (CYSC) polymer which:

(A) comprises a plurality of repeating units having the formula:

(1)

where $R^1$ is hydrogen or methyl, and
Cy is a moiety comprising an n-alkyl moiety containing 18-24 carbon atoms;

(B) has a crystalline melting temperature (Tp) of at least 40° C., an onset-of-melting temperature (To) such that Tp−To is less than $Tp^{0.7}$, and a heat of fusion of at least 5 J/g;

(C) has a number average molecular weight (Mn) less than 10,000;

(D) is not a thermoplastic elastomer, is not a block copolymer and is not a graft copolymer; and (E) is not cross-linked;

the method comprising the steps of (1) distributing the drug in the polymer by mixing the drug with the polymer while the polymer is at a temperature above its crystalline melting temperature, and (2) cooling the mixture.

In another embodiment the method encompasses a method for making a formulation by dissolving a drug in a polymer such that the drug is distributed within the formulation in such a way that there is no phase separation between the drug and the CYSC polymer. The drug is dissolved in the polymer while the polymer is at a temperature above its crystalline melting temperature and the mixture is cooled thereby obtaining a formulation wherein the drug is dissolved in the polymer.

Another embodiment encompasses a method for delivering a drug to a subject over a period of at least 30 days, the method comprising: (1) making an implantable sustained-release formulation which comprises a crystalline side chain (CYSC) polymer and a drug distributed in the polymer, the weight of the drug being at least 5% of the total weight of the formulation, (2) implanting the formulation within the subject, and (3) releasing a therapeutic dose of the drug from the formulation over a period of at least 30 days. Step (1), above, comprises the steps of (i) distributing the drug in the polymer by mixing the drug with the polymer while the polymer is at a temperature above its crystalline melting temperature, and (ii) cooling the mixture, wherein the polymer is a CYSC polymer which: (A) comprises a plurality of repeating units having the formula as described above.

Another embodiment encompasses a method for orally delivering a polypeptide or protein drug to a subject, the method comprising: (1) making a formulation comprising a side-chain crystalline (CYSC) polymer and a drug distributed in the polymer (2) orally administering to the subject the controlled-release pharmaceutical formulation, and (3) releasing a therapeutic dose of the drug from the formulation within the gastrointestinal tract only after the formulation had passed through the acid environment of the stomach into the small intestine, large intestine or colon. Step (1), above, comprises the steps of (i) distributing the drug in the polymer by mixing the drug with the polymer while the polymer is at a temperature above its crystalline melting temperature, and (ii) cooling the mixture, wherein the polymer is a CYSC polymer which: (A) comprises a plurality of repeating units having the formula as described above.

Other embodiments provide variations of the above-described inventions, for example (i) wherein the CYSC polymer does not possess main chain crystallinity, (ii) wherein mixing is carried out at a temperature of less than about 60° C., and the drug is a drug which is damaged by exposure to a temperature above about 60° C. (iii) wherein the CYSC polymer has a Tp of between 40° C. and 60° C., (iv) wherein Cy is an n-alkyl moiety containing either 18 carbon atoms or 22 carbon atoms, (v) wherein the CYSC polymer is a homopolymer, (vi) wherein the CYSC polymer is a random copolymer comprising two or more randomly polymerized monomers, (vii) wherein the weight of the drug is at least 5% of the total weight of the formulation, (viii) wherein the drug may be some or all of the following: a proteins or polypeptides, anti-pain medications, anti-psychotics, neurotransmitter agonists, neurotransmitter antagonists, anti-inflammatories, hormones, anti-osteoporosis drugs, anti-angeogenics, cytotoxic agents, chemotherapeutics or contraceptives or may be a compound containing functional groups of benzisoxazole and/or piperidine, olanzapine, fluphenazine maleate, chlorpromazine, chlorpromazine hibenzoate, sulpiride, carpipramine hydrochloride, carpipramine maleate, clocapramine hydrochloride, risperidone, fluoenthixole, perphenazine, quetiapine, mosapramine hydrochloride, clozapine, sertindole, an SSRI and a pharmacologically active derivative, congener or metabolite of any of the foregoing, for example the drug may be Risperidone or a pharmacologically active derivative, congener, pro-drug or metabolite thereof or Diclofenac or a pharmacologically active derivative, congener, pro-drug or metabolite thereof. Sustained release formulations may provide release of a therapeutic dose of the drug from the formulation over a period of at least 10, 20, 30, 40, 50, 60 days or more. The formulation may be made suitable for subcutaneous or intramuscular delivery to a subject. In such implantable dosage forms the dosage form may release the drug with a profile selected from the group consisting of: (i) release of drug no greater than 20 milligrams per day averaged over any 24 hour period during the first 168 hours of elution; (ii) release of drug continuously between 0.1 milligram and 20 milligrams per day over a period of at least 30 days; (iii) release of drug between 0.1 milligram and 20 milligrams per day, averaged over any 24 hour period during a period from 12 hours to 168 hours following inception of elution; and (iv) release of no more than 20% by weight of total drug loaded into the formulation over any period of 24 hours. Formulations for orally delivering a polypeptide or protein drug to a subject are also included in the invention particularly for delivery of polypeptide or protein drugs.

Documents describing drug delivery include for example U.S. Pat. No. 5,919,484, U.S. Pat. No. 6,423,345, US 2005/0249799, WO 2006/039152, U.S. Pat. No. 6,951,642, U.S. Pat. No. 6,656,385, US 2004/0236013, U.S. Pat. No. 6,699,952, U.S. Pat. No. 6,730,322, U.S. Pat. No. 6,964,778, U.S. Pat. No. 6,200,598, U.S. Pat. No. 6,524,274, US 2004/0052746, US 2004/0208844, WO 0187276, WO 2004/052339, U.S. Pat. No. 6,469,133, US. 2007/0142461, US 20010044514, U.S. Pat. No. 4,830,855, U.S. Pat. No. 4,558,690, U.S. Pat. No. 6,887,960, WO 99/36058, U.S. Pat. No. 6,951,642, U.S. Pat. No. 6,576,254, US 2006/0167116, J W Lee et al., Journal of Polymer Science, Part B Vol 38 #6, 823-830, J S Wei et al., Frontiers in Bioscience 10, supplement, 2005, Sep. 1, 2005, 3058-3067, C C Ng et al., J Sex Reprod Med Vol 1, #1 Summer 2001, pp 21-27, S Davaran et al., Journal of Controlled Release, 58, #3, pages 279-287 (1999), G Erdodi et al., Macromol. Sympos., Vol 227, 2005/July 2005, pp 265-273, Cheng et al., Biomacromolecules, 2006 May; 7(5):1509-20, C J Boudreaux et al., Journal of Controlled Release 44, #2-3, 1997 pp 185-194, V P Torchilin et al., Journal of Controlled Release Vol 73, #2, pages 137-172 (2001), V Bulmus et al., J Control Release 93, #2, 2003 Dec. 5, pp 105-120, K M Scholsky et al., J Controlled Release, 3, 87-108 (1986); Luppi et al, "pH-sensitive polymeric physical-mixture for possible site-specific delivery of ibuprofen", Eur-J-Pharm-Biopharm. 2003 March; 55(2): 199-202. Additional relevant publications include the Nathan patents: U.S. Pat. Nos. 6,866,860; 6,872,799; 6,967,234; 7,005,136; 7,026,374; 7,030,127; 7,034,037; 7,253,248; 7,326,426; 7,198,675. Also relevant are U.S. Pat. No. 6,967,234; U.S. Pat. No. 6,967,234; U.S. Pat. No. 7,005,136 and U.S. Pat. No. 7,0034,037; also EP 0778304 and U.S. Pat. No. 6,657,042 to Rafler; U.S. Pat. No. 7,220,469 to Daicel; U.S. Pat. No. 5,628,993 and U.S. Pat. No. 5,750,100 (Takeda); and U.S. Pat. No. 5,308,623 to Henkel. Other relevant publications are US2002/0161437; U.S. Pat. No. 6,989,417; U.S. Pat. No. 6,469,133 and CA 2487514.

Additional relevant non-patent literature includes Nilmini K. Abayasinghe, Sibylle Glaser. K. Prasanna, U Perera, Dennis W Smith Jr, Journal of polymer Science Part A Polymer Chemistry #43, 5257-5266 (2005), Oligoethylene-End-Capped Polylactides; and Lin Yu, Huan Zhang, Jiandong Ding, Angew. Chem. Int. Ed. 2006, 45, 2232-2235—A Subtle End-Group Effect on Macroscopic Physical Gelation of Triblock Copolymer Aqueous Solutions; and Dieter Bendix, Polymer Degradation and Stability 59 (1998) 129-135, Chemical Synthesis of Polylactide and its Copolymers for Medical Applications.

The entire disclosure of each of the publications, patents and patent publications referred to in this document is incorporated herein by reference for all purposes.

The term "CYSC polymer" (an abbreviation for crystalline side chain polymer) is defined herein as a polymer which:
(A) comprises at least one moiety which
   (i) has the formula -b-Cy-
   (ii) forms part of a repeating unit which
     (a) provides at least part of the polymeric backbone of the polymer and
     (b) has formula (1) below, and/or
   (iii) forms at least part of a terminal unit of the polymer backbone which has formula (2) below

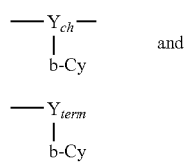

where $Y_{ch}$ is a trivalent moiety forming part of the backbone of the CYSC polymer,
$Y_{term}$ is a divalent moiety at the end of the backbone of the CYSC polymer,
$Y_{term}$ is a divalent moiety at the end of the backbone of the CYSC polymer,
b is a bond or a moiety having a valence of at least 2, the moiety linking the Cy moiety to
$Y_{ch}$ in the polymer backbone, and
Cy is a monovalent moiety which is capable of associating with other moieties (which may also be Cy moieties) to provide the CYSC polymer with crystallinity; and
(B) has a crystalline melting temperature, Tp, of at least 0° C. and a heat of fusion of at least 4 J/g which results from the association of the Cy moiety (Tp and heat of fusion being measured on a DSC as hereinafter described).

The moiety -b-Cy is also referred to in this specification as an -Rc moiety, i.e. Rc is synonymous with -b-Cy. The CYSC polymers which contain a moiety of formula (2) above are sometimes referred to in this specification as end capped (ECC) polymers.

The moieties $Y_{ch}$, $Y_{term}$, b and Cy can be of any kind, and in CYSC polymers containing more than one moiety of formula (1) and/or more than one moiety of formula (2), $Y_{ch}$, $Y_{term}$, b and Cy can be the same or different. A wide variety of such moieties are described below. The CYSC polymer can optionally contain, in addition to the moieties of formula (1) and (2), repeating units and/or terminal units having a different formula. Purely by way of example, $Y_{ch}$ can be a

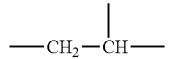

moiety, $Y_{term}$ can be a —$CH_2$—$CH_2$— moiety, b can be a —$CO_2$— moiety and Cy can be an n-alkyl moiety containing 18 carbon atoms.

Where reference is made in this specification to a moiety of formula —Y— or —Y(bCy)- or —Y(Rc)-, —Y— can be $Y_{ch}$ or $Y_{term}$.

The term CYSC compound is defined herein as a compound which
(A) has the formula $$Q(\text{-}b\text{-}Cy)_q$$

wherein q is at least 2, e.g. 3-8,
Q is a moiety having a vacancy of at least q,
b is a bond or a divalent moiety linking the Cy moiety to the Q moiety (i.e. the same definition as for b above, except that b links the Cy moiety to the Q moiety, rather than to the polymer backbone), and
Cy is a monovalent moiety which is capable of associating with other moieties (which may also be Cy moieties) to provide the CYSC compound with crystallinity; and
(B) has a crystalline melting temperature, Tp, of at least 0° C. and a heat of fusion of at least 4 J/g which results from the association of the Cy moieties (Tp and heat of fusion being measured on a DSC as hereinafter described).

A CYSC compound can, for example be obtained by esterification of a polyhydroxy compound, e.g. a sugar such as sorbitol, with an n-alkyl carboxylic acid (or the like) in which the n-alkyl moiety contains at least 14 carbon atoms, preferably 18-30 or 18-22 carbon atoms, or by esterification of a polycarboxylic compound with an n-alkyl alcohol in which the n-alkyl moiety contains at least 14 carbon atoms, preferably 18-30 or 18-22 carbon atoms.

A fatty acid as used herein is a carboxylic acid which contains a Cy radical. A fatty alcohol as used herein is a fatty alcohol which contains a Cy radical.

The number of free hydroxyl groups on the polyol will determine the number of end capped groups.

A bioactive material associated with a CYSC polymer can for example be delivered at a controlled rate and/or at a desired location, the rate and/or the location being influenced for example by a chemical and/or physical condition which modifies the association of the drug and the CYSC polymer. The condition can for example be an environment which causes the CYSC polymer to undergo a chemical change (for example the weakening or creation of any kind of chemical association, e.g. oxidation, reduction or hydration) and/or a change in physical state (for example the weakening or creation of any kind of physical association, e.g. a change in viscosity resulting from melting or crystallization, for example caused by internal or external heating) including an environment having a particular pH range or the presence of an enzyme. The term "controlled rate" includes, but is not limited to, a continuous, sustained rate, an increasing or decreasing rate, continuous or discontinuous release, or maintenance of a substantially constant rate. The bioactive material may be released, for example, with zero-, first- or second-order release kinetics.

Various Aspects of the Invention (1) A novel composition comprising a CYSC polymer and a bioactive material associated therewith. The polymer and the bioactive material may be mixed in such a way that the bioactive material is dispersed within the polymer, either evenly dispersed or unevenly dispursed.

(2) Novel methods of controlling the release of a bioactive material from a composition as defined above. The method may comprise subjecting the composition to conditions which affect (i.e. decrease, increase or maintain substantially constant) the strength of the association between the bioactive material and the CYSC polymer in at least part of the composition, for example at an exposed surface of the composition.

(3) Novel methods of treating an organism which comprise administering a CYSC polymer and a bioactive material to the organism, the polymer and bioactive material being associated with each other before administration or becoming associated with each other during or after administration.

(4) Novel methods of making a composition. In various embodiments, the methods of making the composition involve mixing a bioactive material and a CYSC polymer, specifically without the presence of a liquid (or solvent) at a mixing temperature which is below the temperature which would harm the bioactive material (by denaturing it or affecting it in some way which would substantially reduce its activity or produce degradation products that would reduce its short-term or long-term stability). In other embodiments, the mixing is carried out in the presence of a liquid (which liquid may be a solvent for one or both or neither of the active material and the polymer). The liquid can be, for example, water, an aqueous solvent, a non-aqueous solvent (e.g. an aliphatic, aromatic or mixed aliphatic/aromatic organic solvent), a polar solvent, or a non-polar solvent. The CYSC polymers can often be designed to melt over a relatively narrow temperature range and at a desired temperature between 10 and 120° C. (as measured on a differential scanning calorimeter (DSC) as described below). Furthermore, it is possible to obtain similar melting characteristics over a relatively wide range of molecular weight. The melting point can for example be about 30° C., about 35° C., about 37° C., about 40° C., about 45° C., about 50° C., about 55° C., about 60° C., about 65° C., about 70° C., about 75° C., or about 80° C. The melting point of a composition comprising a CYSC polymer and a bioactive material will often be different from, generally lower than, the melting point of the CYSC polymer. When the bioactive material is a drug to be administered to a mammal, it is often desirable for the composition to have a melting temperature above the body temperature of the mammal (e.g. above 37° C.). However, in some embodiments, the composition preferably has a melting temperature below 37° C., so that the composition, once implanted, maintains a non-solid consistency.

The relatively low melting point and narrow melting range of CYSC polymers is particularly useful for making compositions containing a bioactive material which is adversely affected by exposure to elevated temperatures and/or to solvents. For example, it is a well known problem that the preparation of many polymer-drug compositions requires either or both of elevated temperature or the presence of solvents, because many polymers, on their own, are sufficiently fluid only at elevated temperatures. Elevated temperatures can be harmful to the activity and/or the stability (short or long term) of many drugs and other bioactive materials (for example but not limited to, proteins), and many solvents are known to have deleterious effects on bioactive materials or on organisms to which the compositions are administered, e.g. toxicity to mammals. In addition, exposure of pharmaceutical compounds to such solvents may induce some chemical of physical degradation that may result in reduction of its potency or purity, either immediately upon exposure or during long-term shelf storage. The present invention allows low temperature mixing of a drug and polymer, often without using a solvent. The mixing temperature can for example be 40-80° C., e.g. 50-75° C. or 45-55° C.; it may be no greater than 40° C., 45° C., 50° C. or 55° C.; or it may be a temperature which is 5-55° C., e.g. 5-45° C. or 5-30° C., or 5-15° C. or 5-10° C. above the Tp of the polymer, for example no greater than 5° C., 10° C., 15° C. or 20° C. above the Tp of the polymer.

(5) Novel devices for administering a CYSC polymer and a bioactive material, the CYSC polymer and the bioactive material being in the form of a composition as defined in (1) or being separately administered. Such devices can for example comprise a substrate coated with such a composition or with ingredients for forming such a composition, or a reservoir which acts as a depot which consists essentially of, or which contains, such a composition; or which comprises components which form such a composition before or after administration.

(6) The use of a formulation as defined herein to deliver a therapeutically effective amount of a drug to a subject in a sustained manner over a protracted period of time, such as, for example, over at least 12 hours, over at least 24 hours or over at least 42 hours.

(7) Novel methods of making devices as defined above, the method comprising associating the bioactive material with a CYSC polymer while the CYSC polymer is supported by a substrate, e.g. a polymeric or metal substrate.

BRIEF DESCRIPTION OF THE DRAWINGS

The invention is illustrated in the accompanying drawings in which the Figures summarize results obtained in the Examples, as further described below.

The table below shows the correlation between the Example numbers in Tables 1A, 1B and 1C and the Sample numbers referred to elsewhere in the specification.

| Example No. | 1A | 2A | 3A | 4A | 5A | 6A | 7A |
|---|---|---|---|---|---|---|---|
| Sample No. | 328-133-1 | 326-1-1 | 326-2-1 | 326-3-1 | 326-5-1 | 327-1-1A | 327-39-1 |
| Example No. | 8A | 9A | 10A | 11A | 12A | 13A | 14A |
| Sample No. | 327-40-1 | 326-8-1A | 326-8-3 | 327-3-1B | 327-3-3B | 327-137-1 | 327-137-3 |
| Example No. | 15A | 16A | 17A | 18A | 19A | 20A | |
| Sample No. | 326-6-1 | 326-6-3 | 326-9-1 | 326-11-3 | 327-42-2 | 327-42-11 | |

DETAILED DESCRIPTION OF THE INVENTION

Definitions

In this disclosure the following definitions are employed.

The terms "pharmaceutical formulation," "pharmaceutical composition," and "drug formulation" mean any composition which (i) is suitable for administration to a human being or other mammal or which can be treated, e.g. sterilized, to make it suitable for such administration, and (ii) comprises at least one bioactive ingredient and at least one CYSC polymer. In addition, a formulation may comprise additional, non-active components, such as pharmaceutical excipients, fillers, carrier materials etc. that may be used to modify or improve the drug release, improve its physical and/or chemical stability, dosage form performance, processing, manufacturing, etc. Additionally, a pharmaceutical formulation may include nutrients, nutraceuticals and cosmetic compositions, including compositions sometimes referred to as cosmaceuticals.

The term "Personal Care" applies to all applications related to cosmetics, hygiene and non-medical applications involving application of a substance into or onto the human body including human hair.

The terms "drug", "therapeutic", "therapeutic agent", "active agent" or "bioactive material" refer to any bioactive material which is biologically, physiologically, or pharmacologically active, in a human being or other mammal, locally and/or systemically, and includes diagnostic agents. Examples of drugs are described in well known literature references such as the Merck Index and the Physicians Desk Reference and they include, without limitation, medicaments; vitamins; mineral supplements; substances used for the treatment, prevention, diagnosis, cure or mitigation of a disease or illness; substances which affect the structure or the function of the body; pro-drugs, which become biologically active or more active after they have been placed in a physiological environment, biologically active metabolites of drugs which become biologically active or more active once they have been produced by the metabolism of a precursor chemical. Different types of drugs which may be used with the invention are discussed in more detail later in this application. Multiple drugs may be included in a single formulation. Drugs suitable for use in the present invention are for example disclose in column 11, line 16, to column 12, line 58, of U.S. Pat. No. 6,297,337, and in paragraph 0045 of US 2003/0224974, the entire disclosures of which are incorporated by reference herein for all purposes.

The term "organism" encompasses, but is not limited to, human beings and other mammals, living tissue which is not part of a mammal, plants, seeds, and soil which contains living organisms. The invention is useful, for example, for delivering drugs to human beings and other mammals; for delivering biocides and/or fertilizers to plants, seeds and soil; and for delivering cosmetic ingredients to human beings.

The term "therapeutically effective amount" means an amount of a therapeutic agent, or a rate of delivery of a therapeutic agent, effective to facilitate a desired therapeutic effect. The precise desired therapeutic effect will vary according to the condition to be treated, the formulation to be administered, and a variety of other factors that are appreciated by those of ordinary skill in the art.

The term "diagnostic agent" means any chemical moiety that may be used for diagnosis or in a diagnostic test. For example, diagnostic agents include imaging agents containing radioisotopes, contrasting agents containing for example iodine, enzymes, fluorescent substances and the like.

The term "treatment" means the application of a process to an individual in order to alter a physiological state, whether or not the process includes a curative element.

As an indicator of the rate at which a drug will be released from a drug formulation in vivo, it is possible to make use of in vitro tests which are designed to mimic the expected physiological conditions in the delivery site or organ of interest (e.g. gastrointestinally for a pill or subcutaneously for an implant). In one example of such an in vitro test, the dosage form is placed in phosphate buffered saline (PBS) at a physiological pH and a physiologically relevant temperature, e.g. about 25° C. or 37° C.; preferably between 32° C. and 37 C. The amount of drug released and the time over which it is released in an in vitro test is no more than an indicator of in vivo results, but is useful for making comparative measurements.

"Controlled" release of a drug or other bioactive material means release of the bioactive material in a pre-determined or adjustable way such that the amount or rate or timing of release is pre-set or is altered in a desired way.

"Sustained" release of a drug or other bioactive material means release over an extended period of time, for example minutes, hours or days, such that less than all the bioactive material is released initially. A sustained release rate may provide, for example, a release of a certain specified amount of a drug from a dosage form, over a certain time period, under physiological conditions or in an in vitro test.

"Bolus" release means release of a large dose, for example all of a drug at one time or over a short period of time. Bolus release can be preceded or followed by sustained release.

The terms "controlled release device", "controlled release dosage form" and similar terms mean any formulation or device wherein the release rate (e.g., rate of timing of release) of a drug or other desired substance contained therein is controlled by the device or dosage form itself and/or by the environment of use. Controlled drug delivery includes delivery of an amount of drug to a particular target site at a particular time, for example delivery of a bolus of drug to a tumor site.

The term "device" when used in the context of drug delivery, such as "drug delivery device" means any device that can deliver a drug, including pills, capsules, gels, depots, medical implantable devices (e.g., stents, including self-expanding stents, balloon-expandable stents, drug-eluting stents and stent-grafts, grafts (e.g., aortic grafts), artificial heart valves, cerebrospinal fluid shunts, pacemaker electrodes, endocardial leads, bioerodable implants and the like, and externally manipulated devices (e.g. drug devices and catheters, including catheters which can release a drug, e.g. as a result of heating the tip of the catheter).

The term "dosage form" means a composition which comprises a drug compounded or processed or presented in such a way that it is suitable for administration to a subject. A dosage form comprises a CYSC polymer and, a drug, and may also include one or more other additives, for example pharmaceutically acceptable excipients, carriers, penetration enhancers, stabilizers, buffers or other materials physically associated with the drug and/or the CYSC polymer to enhance the deliverability of the dosage form and/or the effectiveness of the drug. A dosage form may be administered, for example, as a liquid, a suspension, a solid such as a tablet, pill, capsule (including a microcapsule), emulsion, micelle, ointment, gel, emulsion, depot (including a subcutaneously implanted depot), or coating on an implanted device, e.g. a stent or the like. The dosage form can for example be applied externally, e.g. as a patch, or a device applied partly externally and partly implanted, or completely implanted or injected subcutaneously.

The terms "association", "associated" and the like mean any type of interaction, including chemical bonds (including, for example, covalent, ionic and hydrogen bonds) and/or Van der Waals forces, and/or polar and non-polar interaction through other physical constraints provided by molecular structure, and interactions through physical mixing.

The term "functionalized", as applied to a chemical compound, including a polymer, means that the compound has been treated so that it contains a functional moiety (i.e. a moiety which will undergo a further desired chemical reaction) which was not present on the compound before the treatment, or so that the polarity of the compound is changed, as evidenced, for example, by a change in the solubility parameter.

The term "alkyl" is used in this specification to include alkyl moieties which are straight chain alkyl moieties, branched chain alkyl moieties, cycloalkyl moieties, and moieties which consist essentially of two or more of straight chain alkyl, branched chain alkyl and cycloalkyl moieties.

In this specification, parts, ratios and percentages are by weight, except where otherwise noted. Temperatures are in degrees Centigrade (° C.). Molecular weights of polymers are in Daltons, are number average molecular weights (Mn) unless stated to be weight average molecular weights (Mw), and are measured by gel permeation chromatography (GPC) with a light scattering detection method, using a DAWN DSP laser photometer from Wyatt Technology. In defining the polymers, this specification uses the terms "melting point" (often abbreviated to Tp or Tm), "onset of melting temperature" (often abbreviated to To) and "heat of fusion" (which is a measure of crystallinity of the polymer, is expressed in J/g and is often abbreviated to ΔH). Tp, To and ΔH are determined using a differential scanning calorimeter (hereinafter DSC), e.g. a Q 100 DSC from TA Instruments at a rate of temperature change of 10° C./min, e.g. from −10 to 150° C. Tp is the peak melting temperature, and To is the temperature at the intersection of the baseline of the DSC peak and the onset line, the onset line being defined as the tangent to the steepest part of the DSC curve below Tp. Unless otherwise stated, the values of Tp, To and ΔH are measured on the second heat cycle.

Bulk viscosities given herein are in centipoise and are measured using a Brookfield LVT viscometer with an electronically thermostat controlled thermal heater, controlled for example to 95° C., and small sample adapter using spindles 4 and 7.

General Representations Concerning the Disclosure

As used in this specification, the singular forms "a, an", and "the" include plural reference unless the context clearly dictates otherwise. Thus, for example, a reference to "a part" includes a plurality of such parts, and so forth.

The term "comprises" and grammatical equivalents thereof are used in this specification to mean that, in addition to the features specifically identified, other features are optionally present. For example, a composition "comprising" (or "which comprises") ingredients A, B and C can contain only ingredients A, B and C, or can contain not only ingredients A, B and C but also one or more other ingredients. The term "consisting essentially of" and grammatical equivalents thereof is used herein to mean that, in addition to the features specifically identified, other features may be present which do not materially alter the claimed invention. The term "at least" followed by a number is used herein to denote the start of a range beginning with that number (which may be a range having an upper limit or no upper limit, depending on the variable being defined). For example "at least 1" means 1 or more than 1, and "at least 80%" means 80% or more than 80%. The term "at most" followed by a number is used herein to denote the end of a range ending with that number (which may be a range having 1 or 0 as its lower limit, or a range having no lower limit, depending upon the variable being defined). For example, "at most 4" means 4 or less than 4, and "at most 40%" means 40% or less than 40%.

When, in this specification, a range is given as "(a first number) to (a second number)" or "(a first number)-(a second number)", this means a range whose lower limit is the first number and whose upper limit is the second number. For example, "from 8 to 20 carbon atoms" or "8-20 carbon atoms" means a range whose lower limit is 8 carbon atoms, and whose upper limit is 20 carbon atoms. The terms "plural", "multiple", "plurality" and "multiplicity" are used herein to denote two or more than two features.

Where reference is made in this specification to a method comprising two or more defined steps, the defined steps can be carried out in any order or simultaneously (except where the context excludes that possibility), and the method can optionally include one or more other steps which are carried out before any of the defined steps, between two of the defined steps, or after all the defined steps (except where the context excludes that possibility). Where reference is made herein to "first" and "second" features, this is generally done for identification purposes; unless the context requires otherwise, the first and second features can be the same or different, and reference to a first feature does not mean that a second feature is necessarily present (though it may be present). Where reference is made herein to "a" or "an" feature, this includes the possibility that there are two or more such features (except where the context excludes that possibility). For example, a composition which comprises a CYSC polymer and a drug, the composition can comprise two or more CYSC polymers and/or two or more drugs. Where reference is made herein to two or more features, this includes the possibility that the two or more features are replaced by a lesser number or greater number of features providing the same function (except where the context excludes that possibility). The numbers given herein should be construed with the latitude appropriate to their context and expression; for example, each number is subject to variation which depends on the accuracy with which it can be measured by methods conventionally used by those skilled in the art.

This specification incorporates by reference all documents referred to herein and all documents filed concurrently with this specification or filed previously in connection with this application, including but not limited to such documents which are open to public inspection with this specification.

CYSC Polymers b Moieties b is a bond or a divalent moiety linking the Cy moiety to an intermediate point on the polymer backbone or to a terminal moiety. Thus, b may for example be a covalent bond, or a divalent organic moiety (e.g. an aliphatic, aromatic or mixed aliphatic/aromatic moiety) or inorganic moiety. Examples of b moieties include ester, carbonyl, amide, amine oxide, hydrocarbon (for example phenylene), amino, ether, polyoxyalkylene, or an ionic salt linkage (for example a carboxyalkyl ammonium, sulfonium or phosphonium ion pair).

Cy Moieties

The Cy moieties (which provide side chains pendant from an intermediate location and/or from a terminal location of the polymer backbone) in a particular CYSC polymer may be the same or different. The Cy moieties must be such that they are capable of interacting with other Cy moieties, for example other Cy moieties elsewhere on the same polymer and/or on a different polymer (which may or may not be a CYSC polymer) and/or on a non-polymeric molecule, to provide crystallinity. The interaction between the Cy moieties is generally by way of hydrogen bonds or Van der Waals forces, and not via covalent or ionic bonding.

The Cy moieties can be of any kind, for example aliphatic, e.g. alkyl, or mixed aliphatic aromatic. The CYSC polymers contain moieties such that the polymer, when examined on a DSC in the manner defined below, has a heat of fusion of at least 4 J/g and an associated distinct melting temperature resulting from crystallization of the Cy moieties. Such polymers are known and have been referred to as side chain crystalline polymers (sometimes abbreviated to SCC polymers or SCCPs). Some SCC polymers contain Cy moieties whose nature, amount and distribution are such that the polymer has a heat of fusion of at least 10, at least 20, at least 25, at least 30, at least 35, at least 40, or at least 45, for example 4-50 or 10-50, or 10-40 or 15-35 or 20-30 J/g.

Patents and other publications relating to SCC polymers include J. Poly. Sci. 60, 19 (1962); J. Poly. Sci, (Polymer Chemistry) 7, 3053 (1969), 9, 1835, 3349, 3351, 3367, 10, 1657, 3347, 18, 2197, 19, 1871; J. Poly. Sci, Poly-Physics Ed 18 2197 (1980); J. Poly. Sci, Macromol. Rev, 8, 117 (1974); Macromolecules 12, 94 (1979), 13, 12, 15, 18, 2141, 19, 611; JACS 75, 3326 (1953), 76; 6280; Polymer J 17, 991 (1985); and Poly. Sci USSR 21, 241 (1979); U.S. Pat. Nos. 4,830,855, 5,120,349, 5,129,180, 5,156,911, 5,254,354, 5,387,450, 5,412,035, 5,469,867, 5,665,822, 5,752,926, 5,783,302, 6,013,293, 6,060,540, 6,199,318, 6,210,724, 6,224,793, 6,255,367, 6,376,032, 6,492,462, 6,540,984, 6,548,132, 6,831,116, 6,989,417, and 7,101,928; and US Patent Application Publications Nos. 2001/0018484 2002/0090425 and 2002/0127305. The entire disclosure of each of those publications, patents and patent publications is incorporated herein by reference for all purposes.

The Cy moieties often comprise a linear carbon chain of at least 8 or at least 12 carbon atoms directly linked to each other, e.g. 12-50 or 16-30 carbon atoms. The moiety is generally not branched, but can be branched providing that the branching does not prevent the moiety from being capable of crystallization. Similarly, the moiety can be unsubstituted or substituted predominantly only by fluorine atoms, or can be substituted by other moieties which do not prevent the moiety from being capable of crystallization.

Cy can be for example a moiety comprising 6 to 50, e.g. 12 to 50, preferably 12 to 22 or 16 to 22, substantially linear carbon atoms, e.g. a moiety comprising at least 11 methylene moieties, for example 11-49 methylene moieties and a terminal methyl moiety, or a moiety comprising at least 5, e.g. 5 to 49 linear perfluoro or substantially perfluoro methylene moieties and a terminal perfluoromethyl moiety or hydrogen atom. Specific examples of suitable Cy moieties include C14, C16, C18, C20, C22, C30, C40 and C50, in particular n-alkyl moieties containing 14, 16, 18, 20, 22, 30, 40 and 50 carbon atoms, and partially or fully fluorinated n-alkyl groups containing at least 8 carbon atoms, and mixtures of Cy moieties having similar average chain lengths.

All the moieties of the formula —Y(b-Cy)- in the CYSC polymer can be the same, or there can be a plurality of (i.e. two or more) different types of moiety which differ from each other in one or more of Y, b and Cy. In some CYSC polymers containing a plurality of different types of —Y(b-Cy)- moiety, the different types are randomly distributed throughout the polymer. In other CYSC polymers, the different types are distributed in a desired non-random fashion in at least part of the polymer, such as in a block copolymer or a graft copolymer. For example, the polymer can comprise at least one polymer block which comprises only one type of repeating unit of the formula —Y(Rc$_1$)- and a second polymer block which comprises only repeating units of the formula —Y(Rc$_2$)-. Alternatively the polymer may comprise one or more sections which contain a plurality of —Y(Rc$_1$)- and —Y(Rc$_2$)- units distributed randomly, and at least one polymer block which comprises (i) only another type of repeating unit of the formula —Y(Rc)-, or (ii) a plurality of randomly distributed different repeating units of the formula —Y(Rc)-.

When there are two or more different Cy moieties, they may have, for example, an average length of 6 to 50 linear carbon atoms, the average being calculated by adding all lengths of all the Cy moieties in the polymer (or, in the case of a block, including graft, copolymer, all the Cy moieties in the block) and dividing by the number of Cy moieties. The average length may have, for example, an accuracy of +/−3%, +/−5%, or +/−10% or any amount therebetween.

Cy Moieties Containing Polyoxyalkylene Moieties

Some useful Cy moieties include polyoxyalkylene, e.g. polyoxyethylene, units. Such Cy moiety can for example be derived from alkoxy polyoxyalkylene(meth)acrylates, where the alkyl portion of the alkoxy group is preferably an alkyl, particularly an n-alkyl, group containing 12 to 50, preferably 12 to 22 carbons, and the polyoxyalkylene unit is a homopolymer, random copolymer, or block copolymer containing 2 to 100, e.g. 5 to 100, preferably 5 to 60, oxyalkylene units, preferably 2-20, e.g. 2-4, oxyalkylene units. Specific examples of such monomers include cetyl polyethoxylated methacrylate, stearyl polyethoxylated (meth)acrylate, behenyl polyethoxylated (meth)acrylate, lauryl polyethoxylated (meth)acrylate, cholesterol polyethoxylated (meth)acrylate and the like. The polyoxyalkylene unit can be attached to the alkyl side chain portion, as for example in hydroxypolyalkyleneoxyalkyl (meth)acrylates with similar alkyl and polyalkyleneoxy groups as above, e.g. hydroxypolyethleneoxystearyl acrylate, hydroxypolyethyleneoxycetyl methacrylate and the like.

Other Moieties Optionally Present in the CYSC Polymer

A CYSC polymer can consist essentially of the moieties of the formula —Y(Rc)- or it can also contain other repeating units of a different type. Such other repeating units can be represented by the formula

$$—Z(Rz)- \quad (5)$$

where Z is a moiety forming part of the polymer backbone and Rz represents a monovalent moiety which is not an Rc moiety. All the repeating units of the formula —Z(Rz)- can be the same, or there can be a plurality of different types of repeating unit which differ from each other in Z, or in Rz, or in both Z and Rz. The moieties of the formula —Z(Rz) can be randomly distributed throughout the polymer, or they can be distributed in a desired non-random fashion in at least part of the polymer.

The presence of Z(Rz) moieties in a CYSC polymer generally depresses the melting temperature and reduces the crystallinity of the CYSC polymer, to an extent which is dependent on the proportion and distribution of the Z(Rz) moieties and the nature of the Z(Rz) moieties. The Z(Rz) moieties also contribute to the chemical and other characteristics of the CYSC polymer, and their presence can be valuable for this purpose. For example, many useful CYSC polymers have an amphiphilic character, with the Cy moieties providing hydrophobic characteristics and the Rz moieties providing hydrophilic characteristics.

The Z(Rz) moieties in a CYSC polymers can be of any kind, for example aliphatic, e.g. alkyl, or mixed aliphatic aromatic. The Z(Rz) moieties can contain any suitable linking group through which they are linked to each other and to the Y(Rc) moieties. For example the CYSC polymer can comprise sections which comprise the Z(Rz) moieties and which are polyacrylate, polymethacrylate, polyalkyl methacrylate, poly-N-alkyl acrylamide, poly-alkyl oxazoline, poly-alkyl vinyl ether, poly-alkyl 1,2-epoxide, poly-alkyl glycidyl ether, poly-vinyl ester, poly-acrylamide, poly-methacrylamide, poly-maleimide, poly-α-olefin, poly-p-alkyl styrene, poly-alkyl vinyl ether, polyolefin, polyether, polyurethane, polysilane, polysiloxane, or poly(alkyl phosphazene).

All the Z(Rz) moieties can be the same, or there can be two or more different Z(Rz) moieties, randomly distributed and/ or arranged in a desired distribution, as for example in a block copolymer in which one of the blocks comprises essentially only one type of Z(Rz) moiety, and another of the blocks comprises essentially only another type of Z(Rz) moiety. The Z moieties (which, when there are two or more different types of Z moiety, can be the same or different) can for example be derived from the addition and/or condensation polymerization of suitable monomers, e.g. acrylic, methacrylic, olefinic, epoxy or vinyl monomers.

The bond between Z and Rz can may be any bond as described in the section discussing the bonds between Y and Rc. The bond may be hydrolytically stable, unstable, or labile to hydrolysis or enzymatic cleavage.

Suitable monomers from which Z(Rz) moieties can be derived can contain the desired Rz moieties, and/or can contain Rz precursor moieties some or all of which are converted into Rz moieties during or after the polymerization. Suitable monomers are for example alkyl (e.g. 2-ethylhexyl, butyl, ethyl, methyl) (meth)acrylates, hydroxyalkyl (meth)acrylates (e.g. hydroxyethyl acrylate, hydroxyethyl methacrylate) alkoxyalkyl (meth)acrylates (e.g. methoxyethyl acrylate, ethoxyethyl methacrylate), and hydroxypolyoxyalkylene (meth)acrylates (e.g. -hydroxypolyoxyethylene methacrylate or acrylate where the ethyleneoxy units are from 4 to 50), other (meth)acrylates (e.g. glycidal methacrylate, (acetoacetoxy)ethyl methacrylate), acrylamides and methacrylamides; styrene; monoacrylic functional polystyrene; alkyl vinyl ethers, and alkyl vinyl esters; and in all of which monomers the alkyl groups are alkyl groups which are not Rc moieties, for example n-alkyl moieties containing less than 12, e.g. 1, 2, 3, 4, 5, 6, 7, 8, 9, 10, 11, or 12 carbon atoms (e.g. vinyl laurate); and polar monomers, for example acrylic acid, methacrylic acid, itaconic acid, dimethylaminoethyl methacrylate, diethylaminoethyl methacrylate, t-butyl acrylamide, dimethylaminopropyl methacrylamide, N-isopropyl acrylamide, acrylonitrile, methacrylonitrile, maleic anhydride, monobutyl fumarate, vinyl acetate, N-vinyl pyrrolidone, and comonomers containing amine groups.

In certain embodiments Rz may comprise polyoxyalkylene e.g. polyoxyethylene, moieties, for example a polyoxyalkylene moiety which links the Z moiety to an end group which is not an Rc moiety Functional Rz Moieties The Rz moieties can for example include one or more desired functional groups, including, but not limited to, the functional groups forming part of the compounds listed below (the disclosure of those functional groups being independent of the moiety forming the remainder of the listed compound). Useful Rz Moieties Include:

(1) Nitrogen-containing side chains, for example the moieties which result from the polymerization of the groups of monomers and specific monomers listed below. It is noted that the identified Rz moieties and/or the functional groups thereon can also be obtained through the use of other monomers:

N,N-dialkyl amino (in particular, dimethylamino) (meth) acrylates; ammonium salt-containing (meth)acrylates, for example 2-trimethylammonium methylmethacrylate chloride, methacrylamidopropyl trimethylammonium chloride, N,N-(diethyl or dimethyl)aminoethyl (meth)acrylate methosulfate; N-vinylpyrrolidinone; imides like the ring-closed reaction products of maleic or itaconic anhydride with primary amines; 2-methacryloxy-N-ethylmorpholine; n- or t-butylacrylamide; (meth)acrylamide; dimethylaminopropyl methacrylamide; 2-t-butylaminoethyl methacrylate; (meth) acrylonitrile; t-butylaminoethyl (meth)acrylate; acryloylmorpholine; N-(2-hydroxyethyl)acetamide; 1-piperidinoethyl (meth)acrylate; and amine oxide containing monomers obtained by reacting alkyl amine containing side chain containing monomers with an oxidizing agent to give an amine oxide of the precursor alkyl amine.

In certain specific embodiments, the formulations of the invention specifically exclude Rz side chains derived from N-vinylpyrrolidinone.

(2) Oxygen-containing side chains, for example the moieties which result from the polymerization of the groups of monomers and specific monomers listed below, including carboxyl- and sulfonic acid-containing monomers and salts thereof. It is noted that the identified Rz moieties and/or the functional groups thereon can also be obtained through the use of other monomers: acrylic acid, methacrylic acid; itaconic anhydride; itaconic acid; maleic anhydride; maleic acid; fumaric acid; monoesters and monoamides of fumaric acid, maleic acid, crotonic acid, and 2-acrylamido-2-methylpropane sulfonic acid ("AMPs"); vinyl sulfonic acid; hydroxyalkyl (meth)acrylates, in particular, hydroxyethyl, hydroxypropyl, and hydroxybutyl) (meth)acrylates; tetrahydrofurfuryl (meth)acrylate; glycidyl methacrylate; alkoxyalkyl (meth)acrylates, e.g. methoxyethyl (meth)acrylate; hydroxycaprolactone acrylate; 1-acryloxy-2-hydroxy-3-phenoxypropane; methylol methacrylate; ethoxyethyl (meth) acrylate; 2-(2-ethoxyethoxy)ethylacrylate; acetoacetoxyethyl (meth)acrylate; phenoxyethyl (meth)acrylate; (meth) acrolein; alkoxy or hydroxyl (polyoxyalkylene) alkyl (meth) acrylates, e.g. methoxy- or hydroxypolyoxyethylene (meth) acrylates, for example those in which the moles of ethyleneoxy units are from 2 to 80, preferably 6 to 50; alkoxy- or hydroxypolyoxypropylene-polyoxyethylene alkyl (meth) acrylates, for example those in which the blocks of each oxyethylene and oxypropylene unit are present in 1/1 to 1/3 ratios whereby the amount of oxyalkylene units in each block is 5 to 100, preferably, 5 to 60 units.

(3) Fluorine-containing side chains, for example the moieties which result from the polymerization of the groups of monomers and specific monomers listed below. It is noted that the identified Rz moieties and/or the functional groups thereon can also be obtained through the use of other monomers: trifluoroethyl (meth)acrylate; heptadecafluorodecyl (meth)acrylate; octafluoropentyl (meth)acrylate; eicosafluoroundecyl (meth)acrylate; hexadecafluorononyl (meth)acrylate; and tetrahydroperfluorodecyl (meth)acrylate.

(4) Phosphorus-containing side chains, for example the moieties which result from the polymerization of the monomers listed below and similar monomers. It is noted that the identified Rz moieties and/or the functional groups thereon can also be obtained through the use of other monomers: 2-methacryloyloxyethyl phosphoryl choline; 2-acryloyloxypropyl phosphoryl choline; and stearyl fumaroylethyl phosphoryl choline.

(5) Silicon-containing side chains for example the moieties which result from the polymerization of the groups of monomers and specific monomers listed below. It is noted that the identified Rz moieties and/or the functional groups thereon can also be obtained through the use of other monomers: silyl monomers, e.g. trimethylsiloxy ethyl (meth)acrylate, 3-acryloxypropyl trimethoxysilane, and 3-acryloxypropyl tris(trimethylsiloxy)silane, monomethacryloxymonotrimethylsiloxyterminated polyethylene oxide, monomethacryloxypropyl alkyl polydimethylsiloxane where the alkyl group contains 1-8 carbon atoms, preferably 1 or 4 carbon atoms, and similar materials sold by for example Gelest as MCR-M17 and MCR-M11, and the like.

(6) Ligand groups which bind to target receptor sites. e.g., receptor proteins that are differentially over-expressed on target cells, for example cancerous cells. Ligands can be physically mixed as well as being part of the CYSC polymer. Ligands are discussed in detail later.

Hydrophilic Rz Moieties

Some CYSC polymers include Z(Rz) moieties in which at least some of the Rz moieties are hydrophilic, the CYSC polymer then being an amphiphilic copolymer having both hydrophobic and hydrophilic characteristics. Formulations comprising such amphiphilic polymers may form micelles or emulsions or liposomes in water, for example containing a hydrophobic drug within the hydrophobic core. It is often convenient to provide CYSC polymers with hydrophilic character by the inclusion of polyoxyethylene oxide units ("pegylation").

Hydrophobic Rz Moieties

Some CYSC polymers include Z(Rz) moieties in which all the Rz moieties are hydrophobic, in which case the CYSC polymer will be a copolymer having only hydrophobic characteristics.

Proportions of Z(Rz) Moieties

The CYSC polymer generally contains Z(Rz) moieties in amount less than 95%, particularly less than 70%, especially less than 100% or less than 50%, e.g. 5 to 25%, based on the weight of the polymer (e.g., 5, 7, 10, 15, 17, 20, 23 or 25%).

The influence of Z(Rz) moieties on the properties and preparation of formulations is further discussed below.

Proportions of Y(Rc) Moieties

A CYSC polymer can be a homopolymer or copolymer which consists of Y(Rc) moieties. However, many useful CYSC polymers contain less than 75%, or less than 50%, e.g. 1 to 75%, 5 to 50%, 15-50%, 15-30% or 10 to 25%, of Y(Rc) moieties, for example no more than 1%, 3%, 5%, 7%, 10%, 15%, 20%, 25%, 30%, 40% or 50% of Y(Rc) moieties. At the lower end of the Y(Rc) moiety content, in order to enhance crystallinity, the Rc moiety preferably contains at least 18 linear carbon atoms and/or the Y(Rc) moieties are present as grafted chains or blocks which consists essentially of the Y(Rc) moieties.

CYSC Polymer Backbones

The backbone of a CYSC polymer can be of any kind. Thus, the —Y— moieties, and the —Z— moieties if present, which can be the same as, or different from, the —Y— moieties, can for example comprise carbon atoms which are linked to each other directly by covalent bonds or through other elements or combinations of elements, and repeating units can be linked to each other directly by covalent bonds or can contain linking units comprising one or more atoms e.g ester (including orthoester), amide, ether or phosphate linkages. For example, the CYSC polymer can be, or can comprise sections which are, polyacrylate, poly-alkyl acrylates, poly-fluoroacrylate, polymethacrylate, polyalkyl methacrylate, poly-N-alkyl methacrylamide, poly-alkyl oxazoline, poly-alkyl vinyl ether, poly-alkyl 1,2-epoxide, poly-alkyl glycidyl ether, poly-vinyl ester, poly-acrylamide, poly-methacrylamide, poly-maleimide, poly-α-olefin, poly-p-alkyl styrene, poly-alkyl vinyl ether, polyolefin, polyether, polyurethane, polysilane, polysiloxane, or poly(alkyl phosphazene). The CYSC polymer can, for example, be derived from the addition and/or condensation polymerization of suitable monomers, e.g. acrylic, methacrylic, olefinic, epoxy, vinyl or silicon-containing monomers.

Melting Behavior of CYSC Polymers

Generally, the melting temperature (Tp) of a CYSC polymer is primarily dependent on the number of carbon atoms directly linked to each other in a straight chain in the Cy moiety(s). Unlike most other crystalline polymers, whose crystallinity depends upon crystallization of the polymer backbone, CYSC polymers show relatively little change in melting temperature with changing molecular weight. Other things being equal, the greater the linear length of the Cy moiety, the higher the melting temperature. For example, the homopolymers of n-alkyl acrylates in which the n-alkyl group contains 14, 16, 18, 22, 30, 40 and 50 carbon atoms have melting temperatures of about 20, 36, 49, 60, 71, 76, 96 and 102° C. respectively. The homopolymers of the corresponding n-alkyl methacrylates have melting temperatures of about 10, 26, 39, 50, 62, 68, 91 and 95° C. respectively. The CYSC polymers used in this invention often have a melting temperature of 22 to 70° C., or 35 to 50° C., or 38 to 50° C., e.g. 37° C. to 42° C. or 40° C. to 47° C. However, CYSC polymers with melting temperatures below 22° C., for example as low as 2° C., or higher than 70° C. may be useful in certain embodiments.

The melting temperatures of copolymers consisting of two or more Y(Rc) moieties reflects the relative proportions of the different Y(Rc) moieties. The presence of Z(Rz) moieties generally reduces the melting temperature and broadens the melting range.

Random copolymers of the long linear chain n-alkyl acrylates and n-alkyl methacrylates generally have intermediate melting temperatures in the range of 0 to 85° C. dependent on the length of the n-alkyl chain. Random copolymers with other monomers, e.g. acrylic acid or butyl acrylate, typically have somewhat lower melting temperatures. Longer chain Z(Rz) comonomers exert greater influence on Tm depression than shorter chain Z(Rz) comonomers since the longer chain monomers have greater potential to disrupt the side chain crystalline domains.

In CYSC polymers containing relatively small amounts of Cy moieties, the extent of crystallinity can be enhanced by incorporating those moieties in blocks or grafts.

The heat of fusion of a polymer reflects the extent of its crystallinity. As a general rule, and other things being equal, the greater the proportion (if any) of Z(Rz) moieties, the lower the heat of fusion of a CYSC polymer. In a CYSC polymer containing particular proportions of particular Y(Rc) and Z(Rz) moieties, the heat of fusion will generally be greater if at least some of the Y(Rc) moieties are adjacent to each other. For example, a random copolymer containing Y(Rc) and Z(Rz) moieties will have less crystallinity (and therefore a lower heat of fusion) than (i) a block copolymer containing first blocks containing substantially all the Y(Rc) Moieties and second blocks containing substantially all the Z(Rz) moieties, or (ii) a graft copolymer in which the grafted chains consist essentially of all the Y(Rc) moieties.

The sharpness of the melting of the CYSC polymers can be quantified by reference to the value of Tp–To. For example, the CYSC polymer can have a Tp–To<$Tp^{0.7}$, e.g. <$Tp^{0.6}$, e.g. less than 15° C. or less than 10° C. or less than 5° C. Thus, for a Tp of 40° C., Tp–To can for example be less than 13.2° C., e.g. less than 9.1° C. This narrow melting range can be very valuable particularly in combination with the ability to control molecular weight substantially independently of Tp, and the ability to select a CYSC polymer having a Tp close to in vivo temperatures. For example, it can facilitate mixing of a CYSC polymer with a bioactive material at temperatures which do not degrade the drug.

Compared to polymers whose crystallinity results from crystallization of the main polymer backbone, the Tp of CYSC polymers is relatively little influenced by the molecular weight of the polymer. It is, therefore, possible, by selection of the repeating units of the polymer, to make CYSC polymers which melt at a desired temperature (e.g. from 2 to 105° C.) and over a relatively narrow temperature range, and which have a desired molecular weight. In addition, as further explained below, CYSC polymers can be designed to have desired chemical and physical properties. As a result, CYSC polymers provide important benefits for loading and delivery of drugs and other bioactive materials. These benefits include for example the ability to make formulations at desired temperatures, in particular at temperatures which do not have any substantial adverse effect on the bioactive material, and the ability to provide formulations having desired properties such as viscosity, adhesion, hydrophobicity, hydrophilicity, volume control, and permeability, loading and rate and/or pattern of release.

In many cases, the CYSC polymers used in the invention do not have any crystallinity which results from crystallization of the polymer backbone ("main chain crystallinity"). However, in some embodiments of the invention, the CYSC polymer is a polymer obtained by modifying a main chain crystalline polymer to introduce Rc moieties at intermediate and/or terminal points on the polymer.

Types of CYSC Polymer.

The CYSC polymer can for example be a random copolymer, graft copolymer or block copolymer (including a thermoplastic elastomer), or core-shell polymer. Non-exclusive examples are as follows.

(a) The polymer comprises one or more types of —Y(Rc)- moiety and one or more types of —Z(Rz)- moiety, all the moieties being randomly distributed.

(b) The polymer is a block copolymer comprising (i) polymer blocks consisting essentially of one or more —Z(Rz)- moieties, and (ii) polymer blocks which comprise one or more types of repeating unit of the formula —Y(Rc)-, and optionally one or more types of repeating units of the formula —Z(Rz)-.

(c) The polymer can be a graft polymer, for example (i) a polymer comprising a backbone which comprises, or consists essentially of, one or more —Y(Rc)- moieties, and grafted side chains each of which comprises, or consists essentially of, one or more —Z(Rz)- moieties, or (ii) a polymer comprising a backbone which comprises, or consists essentially of, one or more —Z(Rz)- moieties, and grafted side chains each of which comprises, or consists essentially of, one or more —Y(Rc)- moieties.

CYSC polymers which can be used in this invention include atactic, syndiotactic and isotactic polymers of n-alkyl α-olefins (e.g. the atactic and isotactic polymers of C16 olefin, having Tp's of 30° and 60° C. respectively); polymers of n-alkylglycidyl ethers (e.g. the polymer of C18 alkyl glycidylether); polymers of n-alkyl vinyl ethers (e.g. the polymer of C18 alkylvinylether having a Tp of 55° C.); polymers of n-alkyl-α-epoxides (e.g. the polymer of the C18 alkyl α-epoxide having a Tp of 60° C.); polymers of n-alkyl oxycarbonylamido-ethylmethacrylates (e.g. the polymers of C18 IEMA, C22 IEMA and C30 IEMA, having Tp's of 56° C., 75° C. and 79° C. respectively); polymers of n-fluoro alkyl acrylates (e.g. the polymer of C8 hexadecafluoroalkylacrylate and the polymer of a mixture of C8-12 alkyl fluoroacrylates, having Tp's of 74° C. and 88° C. respectively), polymers of n-alkyloxazolines (e.g. the polymer of C16 alkyl oxazoline having a Tp of 155° C.); polymers obtained by reacting an hydroxyalkyl acrylate or methacrylate with an alkyl isocyanate (e.g. the polymers obtained by reacting hydroxyethyl acrylate with C18 or C22 alkyl isocyanate and having Tp's of 78° and 85° respectively); and polymers obtained by reacting a difunctional isocyanate, a hydroxyalkyl acrylate or methacrylate, and a primary fatty alcohol (e.g. the polymers obtained by reacting hexamethylene diisocyanate, 2-hydroxyethyl acrylate, and C18 or C22 alcohols, and having Tps of 103° and 106° C. respectively), as well as the acrylate or methacrylate polymers formed from copolymers of very long chain mixtures of aliphatic alcohols like the Unilin alcohols sold by Baker Petrolite averaging C30 or C40 or C50 carbon atoms, which can be converted to (meth)acrylate monomers and polymerized to homopolymers melting about 80, 90 or 100° C. respectively.

The Cy moieties in the CYSC polymers form crystalline aggregates by overlap of the Cy moieties with other Cy moieties in the same molecule or in a different molecule which may or may not be part of a CYSC polymer leading to intermolecular aggregates or domains of crystalline regions. The greater the overlap, the stronger the crystalline aggregate.

Molecular Weight of the CYSC Polymer

The molecular weight of the CYSC polymer can influence the incorporation and/or retention and/or delivery of a bioactive material associated with the polymer. The Mn of the CYSC polymer can for example be 500 to 1,000,000, e.g. 1,000 to 50,000, 2000 to 40,000, 2000 to 25,000, 2000 to 30,000, or 3000 to 20,000 daltons. In some cases it is preferred to use a CYSC polymer having an average molecular weight (Mn) of less than 200,000, or less than 100,000, or less than 50,000, or less than 30,000, or less than 25,000, or less than 20,000, or less than 10,000, or less than 5000, or less than 2500, or less than 1000 daltons, e.g. 1,000 to 20,000, or 1,000 to 10,000 or 2,000 to 20,000, or 3,000 to 5,000 daltons.

In some cases it is preferable that the CYSC materials used for the administration of drugs to mammals should be non-absorbable or essentially nonabsorbable in the patient's body. This is so both for implanted applications and ingested formulations. The polymers as used by the invention are substantially physiologically inactive. For example, polymers which are of high molecular weight, e.g., Mn greater than 10,000 Daltons, charged or crosslinked polymers or polymers which are insoluble under physiological conditions, eliminate or significantly reduce transportation of the polymer across a cell membrane or gut wall. Thus in some embodiments, the CYSC polymers (or their break-down products have a molecular weight of below 20,000, or below 15,000 or more preferably below 10,000 Daltons and are not charged or crosslinked, and are thus voidable from the body.

Solubility Parameters of the CYSC Polymer

The solubility parameters of the polymer or various blocks or grafts within the copolymer can influence the solubility of a particular drug in the polymer, thereby, for example, improving the CYSC polymer's capacity and effectiveness as a drug reservoir. For example, solubility parameter estimations can be found in the book by D. W. Van Krevelan entitled "Properties of Polymers" Elsevier. 2003. As examples, the Log P of the hydrophobic crystalline side chain polymers (wherein Log P=Log of partition coefficient between organic and aqueous phases.) and the pKa (wherein pKa=dissociation constant of the acid or the base) of an amphiphilic crystalline side chain polymers are important in addition to the Tm of the solvated or hydrated CYSC polymers. The partition coefficient, P, and pKa may be used to estimate distribution of drugs, particularly in biological applications. The Log P and pKa assists in addressing CNS (central nervous system) penetration, oral absorption, intestinal absorption, colonic absorption, sub-lingual absorption, and percutaneous absorption, in addition to helping to optimise the physical form and composition of the drug formulation. Understanding the Log P, the pKa, and the Tm properties assists the selection of hydrophobic and hydrophilic groupings for the CYSC polymer to assist mixing with the drug or-other bioactive material for drug formulations. Also, these properties assist selection of the appropriate solvents if solvents are used in mixing of the CYSC polymer with the bioactive material.

Some embodiments of the invention are summarized by the following statements.

A. A pharmaceutical formulation which comprises a drug and a CYSC homopolymer or copolymer and which has one or more of the following characteristics:—
(a) the formulation contains at least 5% or at least 10%, e.g. 5 to 30%, by weight of the drug;
(b) the drug is associated with the polymer by one or more bonds selected from electrostatic bonds, hydrogen bonds, covalent bonds, or by entropic forces;
B. A method of using a pharmaceutical formulation according to Statement A wherein the drug is released in a controlled manner.

The method of Statement B optionally has one or more of the following characteristics.
(a) the drug is released over an extended period of time; and
(b) no more than 80%, preferably no more than 50%, for example no more than 30%, of the total drug loaded into the formulation is released from the formulation over a period of time of 6 hours following administration of the formulation to a subject;
(c) less than 50%, or less than 10%, of the total drug loaded into the formulation is released over a period of time of 1 hour, or over a period of time of two hours, following administration of the formulation to a subject;
(d) at least 75% of the total drug loaded into the formulation is released within 30 minutes of activation of the formulation;
(e) the drug is released from the formulation by one or more of the following changes in condition:
  (i) heating the formulation,
  (ii) hydration of the formulation,
  (iii) exposing of the formulation to an enzyme,
  (iv) changing the pH of the environment surrounding the formulation.

In certain embodiments the formulation may release a therapeutic dose of a drug only at or above a certain pH. For example, a formulation may release little or no drug in an aqueous environment at an acid pH (such as the stomach), but release a therapeutic dose or drug at a less acid pH such as at pH6, or at an alkali pH, such as pH7, pH8, pH9, or pH10 or above. This application is particularly useful for the oral delivery of acid albile drugs such as proteins or peptides that would be damaged by the acid environment of the stomach.

In certain embodiments, the formulation of the invention specifically excludes certain features, for example, in certain embodiments the polymer does not possess main chain crystallinity, or the polymer is not a block co-polymer and is not a graft co-polymer, or the polymer is not a hydrogel, or the polymer is hydrolytically stable, or the polymer does not comprise an anhydride, or the polymer does not contain the structure Ra—CO—O—CO—Rb where Ra and Rb may be any moiety, or the polymer does not comprise a polybasic acid.

Preparation of CYSC Polymers

The CYSC polymers can be prepared in any way, for example using techniques which are well-known to those skilled in the art, e.g. emulsion, solution, bulk and suspension polymerization techniques using conventional catalysts. Conventional additives and catalysts can be employed to achieve desired molecular weights, for example azo and peroxide catalysts, thiol chain transfer agents (e.g. alkyl mercaptans, hydroxyethyl mercaptan, butyl mercaptopropionate and mercapto acetic acid), or allyl chain transfer agents or regulators (e.g. including alpha-methyl styrene). The type of polymerisation can often be selected according to the form of CYSC formulation to be administered. For example, if a micelle or emulsion form is desired, emulsion polymerisation, optionally in the presence of the drug, can be employed; if a hydrogel form is preferred, polymerisation under aqueous or emulsion conditions can be employed; and if a spray-dried form is preferred, polymerisation under solvent conditions can be used.

Methods of preparing graft copolymers include preparing a preformed polymer comprising Y(Rc) moieties and optionally Z(Rz) moieties, and then grafting suitable monomers (which may contain Rc and/or Rz moieties) at reactive sites at the end or in the middle of the preformed polymer. Methods of preparing block copolymers include preparing two or more preformed polymers, at least one of the preformed polymers comprising Y(Rc) moieties and optionally Z(Rz) moieties, and at least one of the other preformed polymer(s) comprising Z(Rz) moieties, each of the preformed polymers having at least one reactive site at an end of, or between the ends of, the preformed polymer, and then reacting the preformed polymers to form the desired CYSC polymer.

For example, in a CYSC polymer may be prepared by copolymerising a vinyl type macromonomer with other monomers, or by making a CYSC polymer, and then reacting the functionalized polymer with the second block material, for example a urethane block, or an epoxy block, a polyether block, a polyester block, a polyethyleneoxide, polypropyleneoxide or polytetramethyleneoxide block, a polysiloxane block, or a poly(alkyl or alkoxy)silane block.

In certain embodiments, the CYSC polymers used in the formulations of the invention are specifically not cross-linked. In certain embodiments, such as hydrogel formulations, however, they may be cross-linked.

When a cross-linked CYSC polymer is desired, the monomer starting material can include a cross-linking monomer, for example to control crosslink density in a hydrogel. Crosslinking monomers or crosslinking reactants can be added at various times during the process including (a) when preparing the polymer in a desired shape followed later by the addition of therapeutic drug or (b) after separately preparing polymer, combining such polymer with therapeutic drug and then finally adding a crosslinking agent to set into a particular shape.

Mixtures of Polymers

A single CYSC polymer or a mixture of CYSC polymers can be used. The CYSC polymer or polymers can also be mixed with an additional polymer which is not a CYSC polymer. The criteria for the selection of a particular CYSC polymer or mixture of CYSC polymers, and optionally one or more additional polymers, depend upon the drug and its desired loading and/or delivery, as further discussed herein. Some embodiments of the invention make use of a composition containing a mixture of two or more CYSC polymers having substantially different melting temperatures, for example melting temperatures which differ from each other by at least 2° C., or at least 4° C. or at least 6° C. or at least 8° C. or at least 10° C. For example, the composition may contain one or more polymers melting at 37° C. and others melting at 39° C. and still others melting at 41° C. Other embodiments make use of mixtures of polymers having drug bound through a range of ionic strengths as defined by the pKa or pKb of the drug-polymer pair.

Formulations

In some formulations, the amount of the bioactive material is at least 5%, at least 8%, at least 10%, at least 20%, at least 25%, at least 30%, at least 35%, at least 40%, at least 50%, at least 55%, at least 60%, or at least 70% of the total weight of the composition. Some formulations may have between 0.1% and 5%, for example up to 2%, 3% or 4% bioactive material.

One of the many useful characteristics of this invention is the possibility of matching a particular bioactive material with a particular CYSC polymer or mixture of CYSC polymers so as to provide desired loading and release characteristics. For many bioactive materials, it is possible to select a CYSC polymer which contains hydrophobic side chains and optionally hydrophilic moieties provided by Rz moieties, and which therefore interacts favorably with the bioactive material. For example, the CYSC polymer can provide sites for association with a drug by van der Waal's forces, ionic association, hydrogen bonding, ligand attachment or covalent bonding. Covalent bonds may be formed for example through an amino or carboxyl linkage, or a divalent organic or inorganic moiety, e.g. an ester, carbonyl, amide, hydrocarbon, an amino, or ether link. Ionic bonds may be formed for example through an ionic salt linkage (for example a carboxyalkyl ammonium, sulfonium or phosphonium ion pair).

Since the CYSC polymer may comprise an amphiphilic structure, with both hydrophobic and hydrophilic moieties, entropic considerations will tend to produce a secondary structure wherein the hydrophilic moieties position themselves on the outside of the structure in an aqueous environment and wherein hydrophobic drug molecules are retained within the interior hydrophobic environment. Drugs may be hydrophobic or hydrophilic and may associate with the hydrophobic or hydrophilic moieties of the polymer.

A CYSC polymer comprises hydrophobic side chain moieties, and as a result a hydrophobic drug may associate with the hydrophobic moieties and thus be protected from an aqueous environment surrounding the formulation. Hydrophobic drugs include, for example, statins, such as atorvastatin, symvastin and pravastatin, SSRIs such as sertraline, anti-inflammatory steroid such as budesonide, risperidone and many other pharmaceutically important molecules.

In some embodiments, the CYSC polymer includes units comprising ionic groups, e.g. units derived from ionic vinyl monomers. The ionic groups can help to stabilize the polymer formulation or help in disassociating the formulation in body fluids. For example, a CYSC polymer containing carboxylate functional groups can reduce or eliminate release of a drug in the acidic environment of the stomach, but can swell in the alkaline environment of the small intestine, thereby releasing the drug in the upper intestine. Other embodiments may employ for example, PEGylated monomers or acidic or other non-ionic or ionic monomers respectively that may be incorporated together as part of the same CYSC polymer or may be present in separate CYSC polymers to be mixed with a drug. The route of drug administration will often be a factor in determining the desirability of the number of ionic or hydrogen bonding groups in the CYSC polymer. For example, a small protein or polypeptide can be mixed with a CYSC polymer to make a stable drug formulation and then administered orally. The protein administered by itself orally might be destroyed when exposed to the highly acidic environment of the stomach. When mixed with CYSC polymer, the protein would be protected from degradation. Alternatively an acid-stable component may be added such as transferrin. In certain embodiments, a protein may be complexed with an absorption enhancing component such as an organic acid, for example with deoxycholic acid, hydroxypropyl-g-cyclodextrin, cholic acid, etc.

In some embodiments the Z(Rz)- moieties may also enhance the physical surface properties of the formulation. For example, polyoxyethylene (meth)acrylate units can provide beneficial slip or hydrophilic properties to tubing, catheters, probes and other medical devices. In some embodiments, the Z(Rz) moieties may also help in the sustained release or delivery of the drug.

As an embodiment of this invention, it is often desirable to reduce burst in order to provide a more steady or zero order delivery of drug to an organism. For example, as noted above in the definition of burst, it is often observed in drug delivery formulations that upon administration there is an initial release of drug from the formulation above the desired therapeutic level, thereby, wasting and often overdosing the drug and in turn reducing the long term theoretical release of drug in the formulation to the organism.

We have found that many formulations of this invention exhibit a reduced burst effect. Moreover, the inventors can further reduce any "burst" of drug from a formulation prior to implantation by pre-treatment of the CYSC polymer-drug formulation before administration. Pre-treatment may be done by contacting the formulation with a liquid, such as water, or physiological saline or PBS or any buffered solution.

The CYSC drug formulation is easy to process, formulate and administer, partly because of the low molecular weight and easy processing ability of the CYSC polymer because of the selection of the Rz functionality to assist in mixing with the desired drug.

These same characteristics also allow easy processing, mixing and formulation of drug-polymer formulations.

Once the drug has been mixed with the CYSC polymer and isolated as a crystalline or semi-crystalline material, the CYSC polymer and drug formulation can be treated with solvents, buffered solutions, coating solutions or other aqueous or aqueous and organic solvent solutions for periods of time at ambient conditions. The coating solutions might contain small amounts of an excipient or polymer coating material. After this treatment the resulting CYSC polymer and drug formulation generally will exhibit a much lower and in some cases almost no burst effect. This embodiment is a significant advantage of preferred CYSC polymers of this invention compared to other drug delivery polymers.

In some embodiments, the presence of PEGylated groupings in the CYSC polymer can increase serum half-life levels of the PEGylated drug, and can reduce immunogenicity and immune recognition of the PEGylated drug. Other enhanced properties that may be provided by PEGylation include bioadhesive properties, and antithrombogenic properties.

In some embodiments, the Z(Rz) moiety can assist in making the polymer formulation more bioadhesive. For example, carboxylic acid or hydroxyl moieties can improve bioadhesivity to muco or intestinal surfaces, as can heparin and heparin sulphates. Hydroxyl or alkoxy polyoxyethlene moieties can also assist in bioadhesion and compatability of the drug.

In some embodiments of this invention, the CYSC polymer contains moieties which, either by hydrogen bonding or ionic bonding or covalent bonding, associate with the drug. These moieties may be derived from comonomers which constitute a minor proportion of the monomers from which the CYSC polymer is derived, for example 1% to 50% by weight (e.g., less than 1, 3, 5, 7, 10, 15, 20, 25, 30, 35 or 40% or from 1-5%, from 1-10%, or from 1-20%), or a major proportion, for example 50 to 95% or 75 to 95% by weight, or any weight in between, of the CYSC polymer (e.g., more than 30, 40, 50, 60, 70, 80, 85, 90 or 95% or from 20-40%, from 30-50%, or from 50-80%).

The selection and amount of the comonomers providing hydrogen bonding or ionic bonding is preferably based on:
a) The active or polar groupings in the comonomer or comonomers and the amount of complementary active or polar groupings in the drug molecule (Hydrophobic/Hydrophilic properties).
b) The hydrophilic or the hydrophobic properties of the drug.
c) The amount of drug to be mixed in the polymer formulation (loading).
d) The control and reduction of the "burst effect" normally observed with a polymer drug reservoir.
e) The desired control of sustained drug delivery which is affected by the interaction of the drug ionically, through hydrogen bonds, ligand attachment or through Van der Waal's forces with the crystalline side chain polymer (Controlled, Sustained Delivery).
f) The method of administration of dosage forms made from the formulation (Form).
g) Quick release of drug when pH activated.

In some embodiments, the presence of Z(Rz) moieties may result in a significant number of stoichiometric ionic interactions between the CYSC polymer and the drug or other bioactive material, thus making it possible to prepare a composition having a high loading of the bioactive material.

In some embodiments, the CYSC polymer includes Z(Rz) moieties that can form a covalent bond with the drug or other bioactive material. In such embodiments, the extent of covalent linkage between the CYSC polymer and the bioactive material will be an important factor in determining release characteristics of the formulation.

For example, with some orally administered drugs it is difficult to administer acid sensitive drugs as the drugs are degraded in the stomach. Likewise it is difficult to administer acid sensitive drugs directly to the stomach lining. By using a strongly covalently associated drug-polymer formulation, the drug can survive the highly acid environment of the stomach with the protective hydrophobic side chain groups surrounding and shielding the drug which is tightly bound through covalent linkage to the CYSC polymer. Once in the alkaline environment of the intestine, the presence of acid groups in the polymer formulation will cause the polymer formulation to swell and allow esterification or other lysis of the covalent bonds, thereby releasing the drug in the small intestine. In one such embodiment a copolymerizable monomer is used to bind the drug covalently to assist in the eventual release of the drug from the polymer formulation. Various covalent bonds may be used to bind the drug to the polymer; some may acid labile, some base labile, and some sensitive to enzymatic cleavage.

Any method can be used to covalently bind a bioactive material to a CYSC polymer. In one example, the CYSC polymer contains a reactive group which is reacted with the bioactive material. In another example, the bioactive material is modified so that it can be used as a comonomer in the preparation of the CYSC material.

In certain embodiments, such as for gastric delivery, the formulation is such that a covalently bound drug is released from the CYSC polymer under conditions of low pH or by gastric enzymes. Exemplary active ingredients are those medicinal agents wherein gastric release is preferred over intestinal release or wherein control of the rate of release of the active agent is desired for systemic action. For example, drugs in which delivery to the stomach is preferred include natural or synthetic prostaglandins and prostaglandin analogues and prostacyclins, (e.g., misoprostol, enisoprost, enprostil, iloprost, and arbaprostil) any drugs for the treatment of peptic ulcers, gastric antisecretory drugs, antimicrobial drugs, prokinetic drugs, cytoprotective drugs and the like. Exemplary antimicrobial drugs include tetracycline, metronidazole and erythromycin which can be used for eradication of gastric microbes such as *Heliobacter pylori*.

In some embodiments of the invention, drugs are bonded to a CYSC polymer for release in an acidic environment depending on the desired physiological action of the drug, systemic side effects associated with each drug, decomposition rate of the drug in a particular environment and other factors well known in the medicinal arts. Such a covalent bond may be pH sensitive and capable of being cleaved at pH values of up to about 7 but stable below that pH.

Covalent bonds which can be cleaved under acidic conditions include bonds of the following types: silyl ethers and esters, acetal, thioacetal, imines, amine, carbonates, and vinyl ethers. Silyl ether covalent bonds are preferred in certain embodiments because such a bond can be formed between a silyl functional group on the polymer (or linker group) and any hydroxyl functional groups on the drug. The drug can be covalently bonded to the polymer backbone or to a pendant functional group on the polymer backbone and can for example be released from the polymer by hydrolytic cleavage of the covalent bond at a pH below about 7. The drug can be incorporated into the polymer by way of a pH-sensitive covalent bond which can for example be cleaved at pH values of less than about 7 but not at higher pH values. Release of the drug at such higher pH values, such as about greater than 7, 8, 9 or 10 or higher, is inhibited.

In some embodiments, the CYSC polymer swells at desired pH values, for example pH values of about 1-7 to enhance release of an effective amount of the drug. The drug can for example be covalently bonded to the polymer as described above through a pH-sensitive linker such that when the polymer swells upon exposure to the acid environment, the release of the drug into the gastric environment is facilitated. In a related embodiment, the formulation releases the drug at pH values up to about 7 and inhibits release of the active ingredient at pH values above 7.

Alternatively, in some embodiments, the polymer can be designed such that the drug remains attached to the polymer at low pH and is triggered to release at high pH.

In one example of the preparation of a formulation in which a modified drug is incorporated into the CYSC polymer, ibuprofen (p-i-butylphenyl propionic acid) is modified by reaction with glycidyl methacrylate, and the modified drug is copolymerised with a linear alkyl acrylate (stearyl acrylate) and an additional copolymerizable monomer, acrylic acid, to give an Ibuprofen CYSC acid containing drug formulation. This drug formulation, administered as a crystalline solid, would bypass the stomach and once in the upper intestine would hydrate, swell, and hydrolyze, releasing ibuprofen for colonic delivery of this drug. Or, ibuprofen can be esterified with a preformed crystalline copolymer of stearyl acrylate and hydroxyethyl (meth)acrylate. A similar ibuprofen acid containing CYSC formulation would be available for colonic delivery of ibuprofen.

In another example, acryloyl chloride is reacted with a hydroxyl group or an amine group of a drug to provide a vinyl containing attachment covalently linked to the drug. This drug-vinyl monomer can then be reacted with the side chain crystalline monomer.

In another example, a vinyl anhydride, e.g. methacrylic anhydride, is reacted with a hydroxyl-containing drug to form a covalent ester linkage between the vinyl anhydride and the drug. Once the modified drug is formed, side chain crystalline monomer is introduced into the reaction mixture and a copolymer is formed between the modified drug, the side chain crystalline monomer and the by-product methacrylic acid (formed from the reaction of the hydroxyl containing drug with the vinyl anhydride). The reaction by-product of methacrylic acid in this case is easier to handle than the hydrochloric acid by-product obtained with the reaction of acryoyl chloride in the earlier example. The methacrylic acid by-product becomes a comonomer with the vinyl group containing therapeutic drug molecule. This type of formulation would be useful for an orally administered drug that, if administered alone, would be damaging to the stomach. In this formulation the presence of excess copolymerized methacrylic acid would help hydrate the molecule once the formulation has passed through the stomach to the small intestine for hydrolysis of the covalent bound drug and absorption in the small intestine.

In some embodiments, a covalently bound drug is released from the polymer carrier enzymatically, for example through ester hydrolysis by an esterase enzyme that would hydrolyze all the acrylate ester linkages.

In some embodiments for gastric delivery, the CYSC polymer provides a number of interacting ionic and hydrogen bonding groups that assist in sterically protecting the sensitive drug in the harsh acidic environment of the stomach. After mixing and cooling, the crystalline side chains will lock the protein or peptide in the hydrophobic side chains, thereby, providing steric protection to the acid sensitive drug. Once through the stomach, the higher pH upper intestine will hydrate the ionic groups of the CYSC polymer allowing release of the sensitive drug into the intestinal tract. The polymer may release or expose the drug by various means including swelling, hydrolysis and by melting by external thermal induction, or by any combination of these means.

For example, a CYSC polymer derived from a linear alkyl acrylate monomer and an acid-containing monomer can be mixed with an amine containing drug, e.g., Sertraline, and cooled to provide a formulation. Upon cooling, the polymer drug ionic structure crystallizes. Once ingested, the crystalline domains protect the drug from reaction with components of body fluids. In its crystalline form this drug is protected from the acidic stomach environment and would not be available for absorption, whereas in the upper intestine the CYSC polymer would hydrate with the excess of acid groups in the CYSC polymer, thereby, releasing the Sertraline for absorption in the upper intestine.

In some embodiments, the CYSC polymer is in the form of a hydrogel. (In other embodiments, it should be noted, the invention specifically excludes a hydrogel). Hydrogels are preferred in some cases because a solid powdered hydrogel can be easily mixed with a solid powdered drug and then hydrated for application. Hydrogels can be hydrophobic, or amphiphilic (i.e. hydrophobic and hydrophilic), and they can be ionic or non-ionic. For example, a CYSC polymer containing units derived from a N-iso-propyl acrylamide comonomer, either alone or in combination with units derived from acrylic and/or methacrylic acid can form hydrogels which are both hydrophobic (from the side chain crystalline monomers) and hydrophilic (from the N-iso-propyl acrylamide and acrylic acid monomers) and which can associate with (depending on the percentage of the hydrophobic and hydrophilic portions) either a hydrophobic or a hydrophilic drug.

Non-ionic hydrogels swell when they absorb water. Ionic hydrogels, which can be anionic or cationic, can be caused to swell to varying degrees by a change in pH. An alkaline pH causes swelling of an anionic gel (because ionic groups like carboxyl are ionized at high pH), whereas a low pH causes swelling of cationic gels.

In some embodiments, the formulation contains a crosslinked CYSC polymer which, because it at least partially retains its shape even under conditions which would cause melting or swelling of the corresponding non-cross-linked CYSC polymer, e.g. above its Tp, will tend to hold a drug longer than the corresponding non-crosslinked polymer. Other embodiments specifically exclude CYSC polymers which are cross linked or immobilized on a support so that they cannot flow at temperatures above their melting temperature.

When the formulation is administered orally, the molecular weight of the CYSC polymer is preferably high enough to limit or avoid absorption across the intestinal wall. For example, polymers which are of high molecular weight, e.g., 1,000-160,000 Mn, and/or which are charged or crosslinked, and/or which are insoluble under physiological conditions, eliminate or significantly reduce transportation of the polymer across the gut wall. The CYSC polymer carrier, after having released the drug, will be passed through the GI tract and be voided. It is generally preferable that the CYSC polymer be substantially physiologically inactive.

In some embodiments, the formulation is delivered intravenously. In such embodiments, it may be desirable to mix the CYSC polymer with, or to graft onto the CYSC polymer, a bioerodable polymer, e.g. portions of natural molecules. In one such embodiment, polylactic acid and/or polyglycolic acid can be grafted by covalent reaction to the CYSC polymer before it is associated with the drug.

Other bioerodable embodiments of the invention comprise formulations comprising a CYSC polymer and copolymers of glutamic acid and aspartic acid or derivatives or similar amino acids. These amino dicarboxylic acids can be alkylated at the amino group with a crystalline fatty acid. Then, these crystalline alkylated fatty amino dicarboxylic acids may be esterified or amidated to give CYSC alkylated amino polyesters or polyamides, respectively. For example, a stearic acid alkylated amino glutamic acid (prepared by alkylating the simple dimethyl or diethyl ester of glutamic acid with stearoyl chloride) may be esterified with a bioerodable polyol such as sorbitol, glycerine, or a low molecular weight polyethylene glycol to give a bioerodible polyester of glutamic acid which has a crystalline side chain attached to the amino group of the glutamate moiety of the polymer. Likewise, aspartic acid can form similar polyesters with crystalline side chain groups. For example, a stearoyl alkylated aspartic acid ester, N-stearoyl dimethyl aspartate may be reacted with glycerine and polyethylene glycol of 6 oxyethylene units to form a polyethylene (EO-6) glycol glyceryl aspartate crystalline side chain polyester.

In a similar manner, the hydroxylamino acids, serine and threonine, may be alkylated at the amino position as noted with the glutamic and aspartic acid examples aforementioned. Once alkylated these hydroxylamino acids can be self polymerized, copolymerized with each other or mixed with other alpha hydroxyl acids such as 3-HP, hyroxyvaleric acid, hydroxyalkonoic acids, or with mixtures of bioerodible diacids and polyols (succinic acid and glycerine respectively, by example) to give CYSC N-alkylated polyesters which are bioerodable.

Another bioerodable embodiment of the invention includes formulations comprising CYSC amino acid polymers. These may be crystalline side chain alkylated amino acids formed from lysine alkylated at the amino group by a crystalline fatty group to give a crystalline amino acid. These alkylated amino acids can be incorporated during polymerization with the CYSC glutamic or aspartic acid derivatives and copolymerized with simple bioerodable polyols like glycerin and sorbitol to give mixed CYSC polyesters and CYSC polyamides.

Another bioerodable embodiment of the invention includes formulations comprising alkyl glucosides in which simple carbohydrates, sugars, starches, etc. are alkylated with long chain alkyl groups or these same starting materials are esterified with crystalline fatty acids. Alternative possible embodiments include, for example, hyaluronic acid alkylated to introduce crystalline side chains into the hyaluronic acid or hydrolysed hyaluronic acid polymer structure.

Another bioerodable embodiment of the invention includes formulations comprising the crystalline and amorphous alkyl polylactides as homopolymers and copolymers with glycolic or lactic acid (from their respective glycolides) and subsequent reactions of these crystalline lactides or lactide copolymers with succinic anhydride or other naturally occurring acids e.g. malic acid, tartaric acid and citric acid and subsequent reactions of these crystalline lactides with ethylene oxide or polyethylene glycols to form pegylated versions of these lactide polymers.

Another bioerodable embodiment of the invention includes formulations comprising simple bioerodible polyesters of bioerodable acids and polyols, for example, succinic acid or anhydride, fumaric acid, tartaric acid, citric acid polyesters with glycerin, sorbitol, PEGs end capped with crystalline fatty acids and/or crystalline fatty alcohols to form ECC or end-cap crystalline polymers.

CYSC Polymers for Peptide and Protein Drug Delivery

The CYSC polymers of this invention are particularly well suited for the drug delivery of protein and peptide drugs. Suitable peptides or proteins which may be delivered by the CYSC polymers of this invention include but are not limited to by example: hormones (such as LHRH, extenatide, HGH, insulin), interferons, erythropoietin, monoclonal antibodies, cytokines, kemokines, cell cycle regulators, transcriptional modulators and the like.

These kinds of drugs are typically administered by subcutaneous injection or intravenous infusion. These drugs are labile and are often affected by temperature, pH, presence of acids, and the presence of ionic groupings as found in cationic and anionic surfactants, often used in drug formulations of small drug molecules. It would be desirable to have alternatives to injection by subcutaneous or infusion (IV—intravenous) methods. To avoid the trauma associated with injections, it would be highly desirable to be able to administer routinely peptide and protein drugs by other methods, for example, oral administration, or by prolonging the release of a peptide or protein using controlled or sustained drug delivery techniques and thereby reducing the number of injections required for administration. Unfortunately, with large hydrolytically unstable molecules like peptides and proteins, it is often difficult to use conventional drug delivery techniques to administer these peptides and proteins because of the unstable nature, in general, of these drugs in aqueous fluids, their acid and enzymic lability, and their water solubility which makes them difficult to mix with typical drug delivery polymers.

Making Drug-Polymer Formulations

Mixing a drug with a polymer to make a drug delivery device is a critically important step in the processing and manufacture of a drug delivery material. The selection of the process will be dependent upon what is desired in terms of drug delivery over time, how the drug will be administered, for example, as an oral tablet, as a parenteral subcutaneous injection or intravenous infusion, transdermal patch application, as an implant which may later be explanted, as a rectal administration, by pulmonary techniques or as a drug eluting coating on a medical device, i.e., drug eluting stent. Each of these application techniques will qualify in large part how a drug must be supplied for administration: as a solid, as a solution, as a coating, as a particle (micro- or nanoparticle), as an emulsion, a suspension, an ointment, capsule or tablet—as several examples of product administration forms.

Within each of these forms there are many possible methods to prepare, for example, a dispersion, an emulsion, or a suspension of a drug and polymer drug delivery system. One of the simplest forms is a solution of a polymer and a drug. In this case typically a solution is injected and if a solution the association of the drug and the polymer may delay slightly the absorption of drug in vivo, but only slightly. More typically, a drug delivery device may be applied as a dispersion, an emulsion or a suspension wherein the drug and polymer matrix is uniformly dispersed in an aqueous solution. A colloidal dispersion of 1 nm to 0.5 mm may be achieved by simple mixing or sonication or homogenation of an aqueous mixture of the drug and polymer matrix in the presence of a surfactant. The drug and polymer mixture may be dissolved in a solvent which evaporates during the sonication or homogenization process. This process can lead to microparticles as the solvent evaporates of from 1 to 1000 microns. These colloidal and emulsion mixtures of fluid and particles may be suitable for a variety of applications. For example, microsphere particles of 125 μm in diameter suspended in suitable aqueous vehicles may be injected through a conventional syringe using a 18 or 20 gauge needle. The type of drug may dictate the processing conditions. As an example, proteins with complex conformational or tertiary structures may be and likely will be affected by harsh manufacturing conditions of conventional emulsification used for microsphere production. Techniques to disperse proteins gently in a polymer solution and atomizing this mixture into liquid nitrogen with extraction of the frozen solvent for the polymer can lead to a stable protein microsphere for suspension and injection. Also, non aqueous formulation of proteins maintains the protein activity and conformation without the presence of an aqueous solution during storage. Or, a polymer and hydrophobic lipid-like material may be melted and mixed with a drug to get a uniform mixture which is then suspended above the melting point of the mixture in a non-solvent which upon cooling will lead to particle solidification, after which the particles may be washed and filtered before re-suspension in an injectible solution.

Microparticles may also be prepared by dissolving a polymer and hydrophobic material in a solvent and dispersing the solid or liquid drug into the solution followed by spray drying to form microparticles, a difficult process for batch-to-batch uniform particle size control.

A more common method of making microparticles is the water/oil/water double emulsion method. An aqueous phase containing the active drug, for example a protein, is dispersed into an oil phase consisting of drug delivery polymer dissolved in an organic solvent under high speed homogenization conditions. The water-in-oil emulsion is then dispersed in an aqueous solution containing a polymeric surfactant such as a polyvinyl alcohol and further homogenized to produce a Water/oil/water emulsion, which after stirring for several hours to allow evaporation of the solvent, the nano- or microparticles are collected by filtration.

Or, a drug delivery polymer may be prepared as an emulsion copolymer using emulsion polymerization technology either in the presence of small amounts of co-solvent. The active drug can then be added in a compatible solvent for the emulsion allowing migration of drug into the emulsion polymer particles.

What is clear is the selection of the form—microparticles, emulsion, solution—is dictated by the application intended and often by the kind of drug being administered using the controlled drug delivery polymer. The polymer and drug must have the ability to be uniformly dispersed together as a uniform matrix of drug and polymer. Also, the drug must be considered as to its stability under the conditions of processing and storage. For example, a protein or peptide may be very susceptible to temperature or mechanical agitation with respect to maintaining its activity and avoiding degradation during the mixing process with the drug delivery polymer and the isolation process as a microsphere or stable emulsion. The final form may be critical to maintaining the activity or stability of the protein and drug delivery particle in the presence of an aqueous carrier solution.

As a significant advantage of embodiments of the drug delivery polymers of this invention is the crystallinity of the polymer while at the same in many cases being low in molecular weight allowing for simple mixing at temperatures above the melting point of the polymer to provide a stable and uniform mixture of drug and polymer once cooled and isolated as a microsphere. Also, with the combination of the crystalline behavior of the drug delivery polymer and its low molecular weight, the drug delivery polymer may be mixed easily with a protein or peptide without disturbing mechanically by homogenization or sonication the conformation or activity of the protein or peptide. In this manner a small particle size drug delivery polymer and protein or peptide matrix system can be prepared. This matrix is uniform and small in particle size because of the crystallinity of the drug delivery polymer. This same crystallinity of the drug delivery polymer may protect the uniformly dispersed protein or peptide from the aqueous solution into which it is suspended.

In certain embodiments the formulation is prepared by melting the CYSC polymer, mixing the drug with the molten polymer, and cooling the mixture to below its melting point to cause crystallization and solidification of the formulation. In some embodiments a solvent may be used to help the drug and the polymer mix, but in other embodiments no solvent is required due to the low melting point of the CYSC polymers used. Carriers, fillers, excipients, dyes, colorings, flavors, distintegrants, stabilizers and other materials may be added to the mixture before it solidifies. The formulation can be processed, either while the polymer is still molten or when the object has solidified for example into rods, ovals, other forms, and tablets etc using known procedures. The CYSC polymer can be selected to have a Tp and a melting range such that there is little or no danger that the drug will be exposed to a temperature or pH which will damage it.

Some CYSC polymers have well defined, low melting temperatures such that it is unnecessary to use solvent to achieve the viscosity needed to allow easy mixing. Thus the invention is particularly useful for the formulation of drugs and other bioactive materials which can be damaged, e.g. denatured or partially or completely inactivated, by such exposure, for example drugs which are damaged by exposure to temperatures higher than a temperature which is more than 15° C., or more than 30° C. above the Tp of the CYSC polymer, for example more than 50° C. or more than 65° C. The melting temperature of the polymer (or polymer mixture) used in the formulation may, for example, be about (or alternatively be not more than) 30° C., about 35° C., about 37° C., about 40° C., about 42° C., about 45° C., about 50° C., about 55° C., about 60° C., about 65° C., about 70° C., about 75° C., about 80° C., or other temperature desired. The polymers may, for example, have melting temperature ranges from 35° C. to 65° C., 40° C. to 65° C., 45° C. to 60° C., 40° C. to 60° C., 50° C. to 65° C., or other range between or within any two of the above temperatures. Generally it is desirable that a polymer-drug composition will have a melting temperature above that of body temperature of the subject (e.g., 37° C.). However, in some embodiments, it will be desirable that the polymer-drug composition have a melting temperature below 37° C., so that the dosage form, once implanted maintains a non-solid consistency.

In certain alternative embodiments the mixture of the drug and melted polymer is dispersed rapidly into cold water or spray dried into a chamber, whereby the polymer formulation precipitates or dries, respectively, into an isolatable form. Microspheres and microcapsules may be formed in this way. However, in some embodiments the drug formulations of the invention exclude microspheres and microcapsules.

Many of the polymers which are already known for use in drug delivery require the use of solvents and/or high temperatures to produce a mixture of the polymer and drug. Some other known drug delivery systems employ hydrogel systems which require the use of ionic conditions to produce a mixture of the hydrogel with the drug. Such temperatures and/or the solvent conditions and/or ionic conditions can inactivate or denature totally or partially the drug. In the present invention, by selecting a CYSC polymer having a low melting temperature, the CYSC polymer can, if desired, be mixed readily in "neat" or 100% pure form with the drug, and it is unnecessary to use a solvent or apply excessive heat or unusual ionic groups that might harm or inactivate a sensitive drug.

Drug Loading & Release

In preferred embodiments, this invention provides one or more of high drug loading, low burst effect, and sustained release of a drug from a CYSC polymer formulation tailored to provide the desired characteristics for the particular drug.

Total drug loading is the amount (usually expressed as the percentage by weight) of the drug present in the formulation. The drug may be chemically and/or physically bound to the CYSC polymer, for example physically entrapped in the formulation. Binding of the drug to the polymer may be through covalent and/or ionic and/or hydrogen bonding and/or van der Waal's forces and/or hydrophobic interactions.

Conventional drug formulations generally contain less than 5% by weight of drug.

Tailoring drug loading and release properties for a particular drug may be achieved for example through selecting polymers with a combination of desired features relating to (a) ionic or covalent attachment of drug molecules to CYSC polymer, and/or (b) capturing the drug molecules in the crystalline hydrophobic domain, and/or (c) presenting a tortuous path around crystalline domains that drug molecules in the hydrophilic domains must navigate to reach the exterior and/or (d) ensuring that the crystalline domains are preferentially on the outside of the formulation. Methods of preferentially locating the crystalline domains on the exterior include, for example, forming particles in air using a spinning disk allowing the hydrophobic side chains to come to the low energy interface or in a hydrophobic medium that would again draw the hydrophobic side chain to the interface, or actually coating preformed particles.

Drug loading and release properties of CYSC polymer formulations can be controlled by altering the solubility of the drug in the polymer and providing association sites for the drug to interact with the CYSC polymer. For example, if the drug is a protein or polypeptide, the ionic groups in the CYSC polymer are preferably selected from those cationic or anionic groups which naturally associate ionically or through hydrogen bonding with the carboxyl or amide groups of the protein or polypeptide side chains. Such ionic groups can be derived from suitable cationic or anionic comonomers forming part of the CYSC polymer or can be subsequently prepared on the preformed polymer by quaternization of, for example, a tertiary amine comonomer copolymerized in the crystalline side chain polymer. Quaternization of a tertiary amine function on the crystalline side chain copolymer can be affected by methyl or some other alkyl chloride or by dimethyl or other dialkyl sulfate treatment of the t-amine to form the quaternary ammonium salt.

A more hydrophobic drug may have a lower concentration of hydrogen bondable or ionic group containing monomers. Yet, there are many hydrophobic monomers that contain ionic groups or contain hydrogen bonding capability to allow the more hydrophobic monomers to form strong ionic or hydrogen bonded associations with a therapeutic molecule.

In the case of sustained release formulations, several days, weeks or even months of therapeutic dosage may be required. A formulation of the invention (such as an implanted drug formulation or device, such as a coated stent or solid implant or polymeric drug depot) may provide at least 5 hours, at least 12 hours, at least 24 hours, at least 36 hours, at least 72 hours or at least 100 hours of therapeutically effective drug delivery. In certain embodiments, as can be seen from the experimental data disclosed, a formulation of the invention may provide at least a week or at least two weeks, at least three weeks or at least a month or at least three month's worth of therapeutically effective drug delivery to a subject. Other formulations may deliver a therapeutically effective amount of a drug to a subject for at least 6 months to at least a year.

In some uses of this invention, interactions between the drug and the CYSC polymer slow the release of the drug from the polymer into the surrounding physiological environment. For example, the interaction of the hydrophobic side chains of the crystalline side chain polymer with a hydrophobic drug will delay dissociation of the CYSC polymer and drug. If the drug is hydrophobic, the drug will tend to associate strongly with the hydrophobic side chains of the CYSC polymer, delaying release into a less hydrophobic (e.g. aqueous) environment. The side chains of the CYSC polymer influence melt temperature and once melted act somewhat like a plasticizer (i.e. an attached plasticizer). The molecular weight of the polymer also influences the release of the drug (for example molecular weight influences in drug diffusion from a crosslinked gel vs. a low molecular weight polymer). These factors are important in controlling the release rate of drug from the polymer drug formulation. If the CYSC polymer associates with the drug by ionic or hydrogen bonding, the drug will be slower to release.

Unexpectedly, it has been discovered that the crystallinity of the CYSC polymer is an important factor in drug loading and release.

The drug formulations of the invention can be specifically designed to provide controlled and/or sustained release. For example, a drug formulation of the invention may be designed so as to release no more than a certain amount of drug over a specific period of time under certain defined circumstances. The rate of loading and release will depend on the specific drug-polymer pair. For instance, a single dose of a drug formulation may release no more than 5% of the total drug loaded into the dosage form, or alternatively no more than 1%, 3%, 10%, 20%, 30%, 40%, 50%, 60% or 70% over a period of 1 hour, or alternatively 3 hours, 6 hours, 12 hours, 18 hours, 24 hours, 36 hours, 48 hours, 72 hours or any combination of the foregoing numbers.

The rate of drug released may be approximately zero order during the main period of therapeutic administration, for example over 99% or 95% or 90% or 80% or 75% of the period of therapeutic administration, or over a period defined by the period of implantation. The maximal variation of drug release rate over the main period of therapeutic administration (for example during the period when therapeutic administration is occurring, at least 12 hours following administration, and before drug release falls below a therapeutically effective level) may not be greater than 50% (or 40% or 30% or 20% or 10%) from the mean rate of release during that period.

The plasma concentration of a drug will be related to the rate of release into the blood balanced against the rate of clearing of the drug from the blood (the drug half-life concentration). The aim of sustained drug delivery is to achieve a therapeutic plasma concentration of the drug over a desirable extended period of time. The desired therapeutic plasma concentration will be a concentration within the therapeutic window below which drug is ineffective, and above which the drug is toxic, or alternatively has no additional beneficial effect.

In a typical embodiment of the invention, a therapeutic dose of the drug as measured by plasma concentration (but alternatively as measured by clinical measurements) will be released over a period of time ranging from at least an hour to at least twelve months. Exemplary drugs suitable for sustained release include, for example, anti-pain medications (e.g. morphine analogues), anti-psychotics (e.g. risperidone or olanzapine), anti-inflammatories (e.g. steroids or NSAIDs), cholesterol lowering drugs (e.g., statins), osteoporosis drugs (e.g. biphosphonates), anti-angeogenics (e.g., anti-VEGF) and contraceptives. In the case of certain drugs such as contraceptives and osteoporosis drugs, sustained release may be desirable over a period of more than a year, for example at least 2, 3, 4, or 5 years. Prior formulations (Norplant) have been used to deliver a therapeutic dose of contraceptives over a period of three years. Long term sustained release formulations will generally be formulated for implantation within the body, e.g., subcutaneously.

The amount (weight) of drug released over a period of time will of course be related to therapeutically effective plasma concentration of the drug, the potency of the drug and drug kinetics including the residence time in the various tissues of interest and the rate of clearing. In use, the rate of release of a drug from the pharmaceutical composition of the invention may be no greater than, for example 10 ng per hour, or alternatively, 50 ng 100 ng 500 ng 1000 ng 2500 ng or 5000 ng or in other embodiments, no more than 10 µg, 50 µg or 100 µg or 500 µg or 1000 µg per hour during the first 6 (or 12 or 24 or 36) hours following implantation. Of course, the desired rate of release of the drug will depend on its potency, its therapeutic window and its half life. For example, Risperidone may be released over a period of time to provide a serum concentration of about 15 ng/ml up to about 100 ng/ml. A release of about 4 mg/day (or in other studies between 1 and 60 mg/day) is found to provide adequate therapeutic serum levels of Risperidone.

In practice, when the drug is released from the formulation, it is released into the surrounding environment, which may be, for example, the intestinal lumen, gastric fluid, subcutaneous tissue, blood, muscle, the colonic space, a body cavity, or any surrounding tissue and/or into interstitial space. The rate of the release is not always easy to measure in practice, and the invention includes methods of determining the rate of release of a drug from a formulation of the invention in vitro, such as by using standard methods such as those described in the United States Pharmacopoeia. One such method, employs a large volume (usually about a liter) of phosphate buffer, pH 7.2, maintained at 37±0.5° C. and stirred at 100 rpm by using a paddle-type dissolution apparatus (such as may be obtained from Electrolab, Mumbai, India). Drug release studies are generally carried out in triplicate and the mean values are calculated. Many standard methods are well known, and when release rates are described and discussed herein, such release rates may be calculated and compared by these standard methods.

In some embodiments, the formulation is such that less than 20%, or less than 15%, or less than 10% (or less than 1%, 3%, 5% or 7%) of the total drug loaded into the formulation is released from the formulation prior to activation of the formulation by a specified condition which triggers a substantially greater rate of release. Such release triggers include, for example, a change in pH and/or swelling of the polymer by hydration and/or contact with an enzyme and/or heating of the formulation. Immediately following the specified condition, the formulation may release drug quickly as a bolus, or steadily over a period of time. For example it may release at least 50% (or 30%, 60% or 75%) of the total loaded drug over a period of not more than 1, 3, 5, 7, 10, 20, 30, 45, 60, 120 or 360 minutes following activation. In embodiments wherein a bolus release is required, substantially all the drug may be released over a very short period of time, such as not more than 1, 2 or 3 minutes, or not more than 30 minutes.

In some embodiments, the rapid melting characteristic of CYSC polymers is used to provide formulations which can be administered in the body and transported to a targeted disease site with little or no release of the drug during transport, but which can be triggered to release the drug at the site by targeted radiation which melts the CYSC polymer at the site. In this way a large dose of a drug can be delivered specifically at the target site when needed. Such embodiments include formulations to target tumour tissue whereby, upon heating, a chemotherapeutic agent is released locally, providing a concentrated bolus of drug at the target site, but minimizing systemic exposure. For example, a chemotherapeutic agent such as carboplatin may be formulated with a CYSC polymer and a targeting ligand such as an antibody or folate that binds selectively to a cell surface receptor differentially expressed on the surface of a specific type tumour cell, for example a colon cancer cell. The formulation may for example be formulated as an emulsion and delivered orally. The emulsion will pass through the stomach and gut to the colon where it will preferentially adhere to tumour tissue. Excess formulation will be voided. An infra-red (IR) source will be used to target the tumour site, heating the adhered formulation and releasing the Carboplatin at high concentration to the target site. Little or none of the drug will be released from the formulation until the formulation is heated. In certain embodiments, a material which can be heated by heat or other radiation.

Often a formulation of the invention may be implanted directly into a subject to provide acceptable burst effect and sustained release. But for some formulations, and particularly with some particularly toxic drugs that have a narrow upper limit to their therapeutic window, pre-treatment of the formulation may be done to reduce burst effect in vivo. Pre-treatment may simply involve soaking the formulation in a biocompatible liquid or elution buffer, for example phosphate buffered saline (PBS) or water for a period of time before implantation. In such an embodiment, the solid polymer formulation would be removed from its packaging, and placed in the elution buffer for, for example 30 minutes to an hour. In some embodiments longer soaking times may be desirable, for example overnight. Soaking may continue for any duration, for example for up to (or alternatively not more than) 1, 3, 6, 9, 12, 24 or 46 hours. This period of soaking will allow the formulation to equilibrate with its liquid environment and may provide some degree of hydration (if hydration does occur), such that any drug that has migrated to the surface, or any drug that would provide a burst release when implanted into the subject will be released during the soaking period. After the soaking period the formulation will be implanted into the subject to provide sustained release of the drug within a therapeutic window.

Induced Drug Release

In some embodiments a therapeutically effective dose of the drug may be released at a predetermined time wherein the drug is released from the formulation by one or more of the following changes in condition (i) heating the formulation, (ii) hydration of the formulation, (iii) exposing of the formulation to an enzyme, or (iv) changing the pH of the environment surrounding the formulation.

Administration of the Formulation

The formulations of the invention may be administered in various ways. Exemplary types of administration include: ingestion, injection, parenteral administration, oral, subdermal, transdermal, transmucosal, intrathecal, intramuscular, inhalation, and application to the skin. Compositions and devices of the invention include lozenges, capsules, tablets, pills, pessaries, lavages, suppositories, inhalable powders, creams, solutions, suspensions, oral suspensions, emulsions, micelle systems, nanoparticles, vesicles, nanocapsules, microcapsules, microparticles, microspheres, microparticles, particles, hydrogels, pills, tablets, including sub-lingual tablets, depots and injectables.

Drugs and Diagnostic Agents, Carriers and Excipients Used with the Invention

Any desired drug may be incorporated into the CYSC polymer formulation of the invention, depending on the particular application sought. The CYSC polymer may be loaded with one or more hydrophilic or hydrophobic drugs, for example, a small molecule, peptide, polypeptide, protein, carbohydrate, polynucleotide, nucleoside, siRNA, immunoglobulin of Fc or Fab fraction thereof, a cyclic compound, alkaloid, beta-lactam, or other antibiotic. The drug may also be an agonist or antagonist of neurotransmitters, an antipsychotic (for example fluphenazine maleate, chlorpromazine, chlorpromazine hibenzoate, sulpiride, carpipramine hydrochloride, carpipramine maleate, clocapramine hydrochloride, mosapramine hydrochloride, Risperidone (or any compound containing functional groups of benzisoxazole and/or piperidine or a pharmacologically active derivative, congener, prodrug or metabolite of the drug), clozapine, olanzapine and sertindole and flupenthixole and perphenazine); or an SSRI; or it may comprise cell signalling molecules such as cytokines such as lymphokines, monokines, chemokines, interleukins, prostoglandins etc a statin, a Cox-2 inhibitor, an SSRI, a calcium channel blocker, psychotropic drug, bisphosphonate, anti-proliferative, mitotic inhibitor, angiogenic factor, antangiogenic factor, small molecule such as rapamycin or derivatives, or almost any other type of drug. Specific drugs and drug classes include ibuprofen, uracils (e.g., 5-fluorouracil), steroids and esters of steroids or other hormones (e.g., estrogen, progesterone, testosterone, androsterone, cholesterol, norethinidrone, digoxigenin, cholic acid, deoxycholic acid, and chenodeoxycholic acid), boron containing compounds (e.g., carborane), chemotherapeutic nucleotides, drugs (e.g., antibiotics, antivirals, antifungals), enediynes (e.g., calicheamicins, esperamicins, dynemicin, neocarzinostatin chromophore, kedarcidin chromophore), heavy metal complexes (e.g., cisplatin, carboplatin), hormone antagonists (e.g., tamoxifen), non-specific (non-antibody) proteins (e.g., sugar oligomers, insulin), polynucleotodes and oligonucleotides (e.g., mRNA sequence), radio-nuclides, toxins (e.g., ricin, and transcription based pharmaceuticals. In certain embodiments the drug may be or may contain bacterial toxins such as botulinum toxin ("botox").

Some Advantages of Invention

CYSC polymers can comprise a desired balance of hydrophobic and/or hydrophilic radicals which can be selected to associate with a wide range of drugs through chemical and/or physical bonds, thus providing formulations which can be delivered to organisms in a wide variety of ways. The CYSC can have sharp and relatively low melting points; can have a desired molecular weight; do not have any adverse effects on organisms; and can be eliminated from organisms after the drug mixed with the CYSC polymer has been delivered to the organism. CYSC polymers can be easily mixed and processed with drugs. One specific example of a formulation containing the psychoactive (antipsychotic) agent Risperidone, (4-[2-[4-(6-fluorobenzo[d]isoxazol-3-yl)-1-piperidyl]ethyl]-3-methyl-2,6-diazabicyclo[4.4.0]deca-1,3-dien-5-one) is the following. Risperidone may be physically mixed with a CYSC polymer, or may be pre-associated, for example with a surfactant, PEG, human (or bovine etc) serum albumin, or with proteins etc. to provide immunological shielding, increased half-life, and improved bioavailability. The formulation may be formed into a shaped solid implant suitable for introduction, e.g. by trocar, under the skin or intramuscularly or by injection above the formulation's melting temperature. It is believed that a dose of Risperidone of about 4 mg/day is sufficient to prevent psychotic episodes in many patients. Individual variations in tolerance and effectiveness, however, can be wide. Therefore the current invention may be formulated to supply from 1 to 60 mg/day over a period of 1 to 200 days. The advantage of an implanted dosage form is increased compliance, which with psychosis, is a major issue. In one embodiment, at least 50 mg of Risperidone is formulated into a single implantable dosage form by mixing the drug in powdered form with a CYSC polymer at a temperature above the Tm of the polymer, for example at between 42° C. and 60° C. No solvent is required. The mixture is cooled and shaped into solid elongated or approximately spherical implants. In other embodiments, the amount of Risperidone formulated into a single implantable dosage form may be at least 100 mg, or at least 200 mg, or at least 500 mg, or at least 1000 mg, or at least 1500 mg, or at least 2000 mg. In some dosage forms, the total amount of drug may be up to 3, 4 or 5 grams. The Risperidone implant is introduced subcutaneously into a subject using a trocar or minor incision. The implant releases Risperidone at an average rate of between 1 and 60 mg (for example no more than 1, 2, 3, 4, 5, 7, 10, 20, 40, 80, 120, 200, or 300 mg) per day over a period of at least 5, 10, 15, 20, 25, 30, 40, 60 or 90 days. In one exemplary embodiment the implant releases Risperidone at an average rate of between 4 and 12 mg per day over a period of at least 7 days. During this period, a desired therapeutic effect is provided for at least 75% of the time. The implant is then removed, or may be left in to erode over time. If a larger bolus of drug is desired, the local area of skin above the implant may be heated by any convenient means. In other embodiments the implant releases Risperidone at an average rate of between 1 and 20 mg per day, or 3 and 100 mg per day or 4 and 30 mg per day over a period of at least 7 days or at least 14, 21, 30, 45, 60 or 90 days. The Risperidone is delivered in such a manner and rate that the blood plasma level of risperidone is within the human therapeutic window, between 1 to 125 ng/ml over the period of 30 or 60 or 90 days. In certain related embodiments, Risperidone may be pre-associated with a surfactant, PEG, human serum albumin or with proteins. In another embodiment, the CYSC polymer comprises side chains having an average length of, for example, between 6 and 50 monomer units. In another embodiment, the CYSC polymer has side chains with an average length of between about 12 and 50 alkyl ester acrylate or methacrylate monomer units.

EXAMPLES

Various formulations of the invention are illustrated by the Examples, the graphs in the Figures and in the following Tables 1A, 1B and 1C. The graphs show the release of substances from the formulations over time. All the graphs show the cumulative release and as can be seen several of the formulations release drug at a fairly steady and predictable rate over a period of time up to and beyond 200 days. Further information about the materials and procedures used in the Examples is given after the Tables.

FIG. 1J shows sustained/controlled release of Risperidone. Typical release testing involving risperidone was conducted by covering the polymer/drug disc with 12.6 grams of buffer solution with pH 5.5, which was removed and replaced by 12.6 grams of fresh buffer solution at the scheduled sampling times at 1 min, 2 hr, 6 hr, daily, weekly, or as necessary. The amount of risperidone released into the sample solution was measured by UV-Vis against a standard curve established by using the absorption signal at $\lambda=276.93$ nm. Uniform mixtures in example 1J were subjected to release testing in phosphate buffer solution (50 mM ionic strength, pH 5.5 made isotonic with 150 mM NaCl and containing 0.01% w/v Tween-20). The following describes the procedure used to prepare the buffer solution. To 100 ml DI water was added 0.16 g of monosodium phosphate monohydrate and 1.04 g disodium phosphate, followed by NaCl and Tween-20 to final concentration of 0.9% and 0.01% w/v, respectively. The pH was adjusted to 5.5 with 0.1N HCl as necessary. The formulations in example 1J are labelled as 330-117-XX, where the numbers XX correspond to the numbers in Tables 1A, 1B &1C. FIG. J1 shows the release profile of risperidone from the mixtures of 9.1% risperidone in 5 polymers.

FIG. K1 shows cumulative release of Risperidone from CYSC polymer 3A at 37° C. This example shows the controlled release profiles of risperidone using 7 uniform mixtures labelled as 336-5-X, where the number X corresponds to the numbers 3K1 to 3K7 in Table K1. FIG. K1 shows the cumulative release of up to 37.5% risperidone from polymer 3A.

FIG. L1 shows sustained/controlled release of risperidone using the 3 uniform mixtures in examples 1L-20L and are labelled as 336-R6-X, where the number X corresponds to the numbers L1 to L4 in Table L1. FIG. L1 summarizes the release profile of risperidone from mixtures of 2A with 3A, 4A and 20A, as well as from single polymers 2A, 3A, 4A and 20A as comparison.

FIG. M1 shows sustained/controlled release of risperidone using the 4 uniform mixtures H1 to H4 in Table H1 in examples 1M-20M and are labelled as 336-R9-X, where the number X corresponds to the polymer numbers H1 to H4 in Table H1. FIG. M1 summarizes the release profile of risperidone from polymers with higher Tm.

FIG. N1 shows sustained/controlled release of risperidone using the 4 uniform 2 phase mixtures in examples 1N-20N and are labelled as 336-3R3-X, where the number X corresponds to the numbers in Tables 1A, 1B &1C. FIG. N1 summarizes the release profile of risperidone from the 4 polymers.

FIG. O1 shows sustained/controlled release of risperidone from polymers 2A, 3A, 4A and 20A in powder form in examples 1O-20O and are labelled as 335-31-XX, where the number XX corresponds to the number for the polymer IDs in Tables 1A, 1B &1C. FIG. O1 summarizes the release profile of risperidone from the 4 polymers.

FIG. P1 shows static temperature triggered release of risperidone from polymer 2A in examples 1P-20P as 0.05 gram scale thin discs at 37° C. and 60° C. The release IDs are labelled as 330-135-2 and 332-3-2 at 37° C. and 60° C., respectively. FIG. P1 summarizes the release profile of risperidone from polymer 2A as 0.05 gram scale thin disc at 37° C. and 60° C.

TABLE 1A

| | Example No. | | | | | | |
|---|---|---|---|---|---|---|---|
| | 1A | 2A | 3A | 4A | 5A | 6A | 7A |
| | 328-133-1 | 326-1-1 | 326-2-1 | 326-3-1 | 326-5-1 | 327-1-1A | 327-39-1 |
| 1 CYSC (molar ratio) | | | | | | | |
| C18A | 1 | 4 | 1 | 4 | 4 | 1.2 | 4 |
| C22A | | | | | | 2.8 | |
| AA | | 1 | 4 | 1 | | | |
| PEG6 A | | | | 1 | | | |
| PEG6 MA | | | | | | 1 | |
| DMAEA | | | | | 1 | | |
| DMAEMA | | | | | | 1 | |
| DMAEA quat | | | | | | | 1 |
| 2 Mw | 3491 | 3012 | 4241 | 3310 | 8876 | 1294850 | 56,825 |
| 3 Mn | 2546 | 2154 | 3376 | 2342 | 7917 | 304,300 | 49,275 |
| 4 DSC $1^{st}$ heat Tp | 50.64 | 51.83 | 44.24 | 45.50 | 46.90 | 55.07 | 56.35 |
| $1^{st}$ heat To | 48.26 | 49.11 | 37.88 | 41.68 | 45.39 | 49.91 | 53.83 |
| $2^{nd}$ heat Tp | 47.06 | 47.55 | 27.90 | 42.06 | 42.85 | 48.94 | 51.69 |
| $2^{nd}$ heat To | 42.22 | 42.92 | 9.6 | 33.39 | 37.70 | 36.07 | 47.62 |

| | Example No. | | | | | | |
|---|---|---|---|---|---|---|---|
| | 1B | 2B | 3B | 4B | 5B | 6B | 7B |
| 5 Sol. In Miglyol (18.97) | Yes | Yes | No | Yes | Yes | Yes | Yes |
| EtOAc (21.02) | Yes | Yes | Yes | Yes | Yes | Yes | Yes |
| NMP (23.12) | Yes | Yes | Yes | Yes | Yes | Yes | Yes |
| $H_2O$ (48.00) | No | No | Yes | No | No | No | No |
| 6 Gel form'n in Miglyol | Yes | Yes | No | Yes | Yes | Yes | Yes |
| EtAc | Yes | Yes | Yes | Yes | Yes | No | Yes |
| NMP | Yes | Yes | No | Yes | Yes | Yes | Yes |
| $H_2O$ | No | No | Yes | No | No | No | No |
| 7 Solubility parameter | 17.17 | 17.31 | 19.14 | 17.50 | 17.31 | 17.43 | 18.09 |

| | Example No. | | | | | | |
|---|---|---|---|---|---|---|---|
| | 1C | 2C | 3C | 4C | 5C | 6C | 7C |
| 8 Dcl/CYSC 1/10 via IPA (9.1%) uniform? | No | Yes | Yes | Yes | No | Yes | Yes |
| 9 DSC $1^{st}$ heat Tp (° C.) | | 49.6 | 42.8 | 47.2 | | 52.7 | 45.9 |
| $1^{st}$ heat To (° C.) | | 45.3 | 40.5 | 43.9 | | 47.2 | 39.1 |
| $2^{nd}$ heat Tp (° C.) | | 43.8 | 40.2 | 41.6 | | 49.4 | 48.3 |
| $2^{nd}$ heat To (° C.) | | 38.7 | 29.1 | 32.9 | | 36.2 | 40.7 |

| | Example No. | | | | | | |
|---|---|---|---|---|---|---|---|
| | 1D | 2D | 3D | 4D | 5D | 6D | 7D |
| 10 Dcl/CYSC/NMP 10/50/50 (9.1%) uniform gel? | No | No | No | Yes | No | No | No |

| | Example No. | | | | | | |
|---|---|---|---|---|---|---|---|
| | 1E | 2E | 3E | 4E | 5E | 6E | 7E |
| 11 Dcl/CYSC/NMP 10/10/90 (9.1%) uniform gel? | No | No | No | No | No | No | No |

| | Example No. | | | | | | |
|---|---|---|---|---|---|---|---|
| | 1F | 2F | 3F | 4F | 5F | 6F | 7F |
| 12 Dcl/CYSC 2/10 via IPA (16.7%) miscible? | | Yes | Yes | Yes | | Yes | Yes |
| 13 Dcl/CYSC 3/10 via IPA (23.1%) miscible? | | Yes | Yes | Yes | | No | No |

TABLE 1A-continued

| | Example No. | | | | | | |
|---|---|---|---|---|---|---|---|
| | 1 I | 2 I | 3 I | 4 I | 5 I | 6 I | 7 I |
| 14 Dcl/CYSC 1/10 via melt (9.1%) uniform? | Yes | | | | Yes | | |

| | Example No. | | | | | | |
|---|---|---|---|---|---|---|---|
| | 1J 328-133-1 | 2J 326-1-1 | 3J 326-2-1 | 4J 326-3-1 | 5J 326-5-1 | 6J 327-1-1A | 7J 327-39-1 |
| 15 Risp/CYSC 1/10 via IPA (9.1%) uniform? | No | Yes | Yes | Yes | No | No | No |
| 16 DSC 1st heat Tp (° C.) | | 50.0 | 38.0 | 45.4 | | | |
| 1st heat To (° C.) | | 45.0 | 30.6 | 40.3 | | | |
| 2nd heat Tp (° C.) | | 42.7 | 35.8 | 40.5 | | | |
| 2nd heat To (° C.) | | 36.8 | 28.9 | 32.3 | | | |

| | Example No. | | | | | | |
|---|---|---|---|---|---|---|---|
| | 1K | 2K | 3K | 4K | 5K | 6K | 7K |
| 17 Risp/CYSC 2/10 via IPA (16.7%) uniform? | | No | Yes | No | | | |

| | Example No. | | | | | | |
|---|---|---|---|---|---|---|---|
| | 1N | 2N | 3N | 4N | 5N | 6N | 7N |
| 18 Risp/CYSC 10/90 via melt (9.1%) uniform? | Yes | | | | Yes | | |

| | Example No. | | | | | | |
|---|---|---|---|---|---|---|---|
| | 1S | 2S | 3S | 4S | 5S | 6S | 7S |
| 19 Prav/CYSC 1/10 via IPA (9.1%) uniform? | Yes | Yes | Yes | Yes | Yes | Yes | Yes |
| 20 DSC 1st heat Tp (° C.) | 47.80 | 51.09 | 44.56 | 46.85 | 48.25 | 55.09 | 54.84 |
| 1st heat To (° C.) | 44.15 | 48.73 | 36.84 | 44.48 | 46.40 | 40.60 | 51.07 |
| 2nd heat Tp (° C.) | 46.64 | 46.98 | 42.63 | 43.02 | 44.04 | 54.14 | 50.23 |
| 2nd heat To (° C.) | 42.51 | 42.59 | 34.74 | 33.18 | 38.92 | 38.25 | 42.97 |

| | Example No. | | | | | | |
|---|---|---|---|---|---|---|---|
| | 1T | 2T | 3T | 4T | 5T | 6T | 7T |
| 21 Dexa/CYSC 1/10 via IPA (9.1%) uniform? | No | No | Yes | No | No | No | No |
| 22 DSC 1st heat Tp (° C.) | | | 44.00 | | | | |
| 1st heat To (° C.) | | | 36.01 | | | | |
| 2nd heat Tp (° C.) | | | 19.84 | | | | |
| 2nd heat To (° C.) | | | 6.43 | | | | |
| 23 Dexa/CYSC 1/10 via melt (9.1%) uniform? | | Yes | | Yes | | | Yes |
| 24 DSC 1st heat Tp (° C.) | | 49.41 | | 45.63 | | | 55.67 |
| 1st heat To (° C.) | | 45.71 | | 41.78 | | | 50.26 |
| 2nd heat Tp (° C.) | | 47.00 | | 42.35 | | | 52.94 |
| 2nd heat To (° C.) | | 43.15 | | 33.02 | | | 47.02 |

| | Example No. | | | | | | |
|---|---|---|---|---|---|---|---|
| | 1W | 2W | 3W | 4W | 5W | 6W | 7W |
| 25 Tacro/CYSC/1/10 via IPA (9.1%) uniform? | Yes | Yes | Yes | Yes | Yes | Yes | Yes |
| 26 DSC 1st heat Tp (° C.) | 49.42 | 50.46 | 43.67 | 47.37 | 48.71 | 54.55 | 53.44 |
| 1st heat To (° C.) | 46.45 | 46.94 | 37.53 | 44.01 | 45.06 | 51.68 | 48.47 |
| 2nd heat Tp (° C.) | 46.25 | 46.43 | 30.71 | 41.91 | 39.56 | 51.74 | 50.25 |
| 2nd heat To (° C.) | 41.71 | 41.99 | 15.78 | 34.74 | 44.27 | 37.67 | 44.17 |

TABLE 1B

| | Example No. | | | | | | |
|---|---|---|---|---|---|---|---|
| | 8A<br>327-40-1 | 9A<br>326-8-1A | 10A<br>326-8-3 | 11A<br>327-3-1 B | 12A<br>327-3-3 B | 13A<br>327-137-1 | 14A<br>327-137-3 |
| 1 CYSC (molar ratio) | | | | | | | |
| C18A | 4 | 3 | 4 | 3 | 2.5 | 3 | 2.8 |
| C22A | | 1 | | 1 | 1.5 | 1 | 1.2 |
| PEG12-OCH3MA | | | | | | 1 | |
| PEG23-OCH3MA | | | | 1 | | | |
| PEG6MA | 1 | | 1 | | | | |
| PEG25-OC22MA | | | | | | | 1 |
| PEG46-OCH3MA | | | | | 1 | | |
| PEG9-OCH3MA | | 1 | | | | | |
| DMAEMA quat | 1 | | | | | | |
| 2 Mw | 67,545 | 3046 | 3459 | 60,845 | 17,785 | 3281 | 4597 |
| 3 Mn | 49,745 | 2220 | 2490 | 21,378 | 6542 | 2064 | 2166 |
| 4 DSC $1^{st}$ heat Tp (° C.) | 49.57 | 47.48 | 45.73 | 49.08 | 51.02 | 48.19 | 48.50 |
| $1^{st}$ heat To (° C.) | 47.00 | 45.76 | 42.08 | 41.74 | 45.04 | 45.30 | 41.98 |
| $2^{nd}$ heat Tp (° C.) | 45.41 | 40.57 | 41.87 | 45.61 | 48.86 | 42.38 | 45.96 |
| $2^{nd}$ heat To (° C.) | 37.33 | 33.03 | 32.55 | 34.17 | 45.26 | 34.30 | 34.26 |
| | Example No. | | | | | | |
| | 8 B | 9 B | 10 B | 11 B | 12 B | 13 B | 14 B |
| 5 Sol. In Miglyol (18.97) | Yes | Yes | Yes | Yes | Yes | Yes | Yes |
| EtAc (21.02) | Yes | Yes | Yes | Yes | Yes | Yes | Yes |
| NMP (23.12) | Yes | Yes | Yes | Yes | Yes | Yes | Yes |
| $H_2O$ (48.00) | Yes | No | No | Yes | Yes | No | No |
| 6 Gel form'n in Miglyol | Yes | Yes | Yes | Yes | Yes | Yes | Yes |
| EtAc | Yes | No | Yes | No | No | Yes | Yes |
| NMP | Yes | Yes | Yes | Yes | Yes | Yes | Yes |
| $H_2O$ | No | No | No | No | No | No | No |
| 7 Solubility parameter | 18.06 | 17.36 | 17.32 | 17.49 | 17.61 | 17.40 | 17.38 |
| | Example No. | | | | | | |
| | 8C | 9C | 10C | 11C | 12C | 13C | 14C |
| 8 Dcl/CYSC (1/10) via IPA (9.1%) uniform? | Yes | Yes | Yes | Yes | Yes | Yes | Yes |
| 9 DSC $1^{st}$ heat Tp (° C.) | 46.3 | 47.2 | 45.4 | 48.6 | 49.9 | 47.7 | 49.8 |
| $1^{st}$ heat To (° C.) | 39.2 | 44.0 | 42.2 | 43.3 | 33.8 | 41.8 | 37.2 |
| $2^{nd}$ heat Tp (° C.) | 43.0 | 42.3 | 41.4 | 46.7 | 44.6 | 44.6 | 46.3 |
| $2^{nd}$ heat To (° C.) | 37.1 | 34.4 | 32.5 | 34.4 | 39.6 | 34.6 | 40.1 |
| | Example No. | | | | | | |
| | 8D | 9D | 10D | 11D | 12D | 13D | 14D |
| 10 Dcl/CYSC/NMP 10/50/50 (9.1%) uniform gel? | Yes | No | No | Yes | Yes | Yes | Yes |
| | Example No. | | | | | | |
| | 8E | 9E | 10E | 11E | 12E | 13E | 14E |
| 11 Dcl/CYSC/NMP 10/10/90 (9.1%) uniform gel? | No | No | No | Yes | Yes | Yes | Yes |
| | Example No. | | | | | | |
| | 8F<br>327-40-1 | 9F<br>326-8-1A | 10F<br>326-8-3 | 11F<br>327-3-1 B | 12F<br>327-3-3 B | 13F<br>327-137-1 | 14F<br>327-137-3 |
| 12 Dcl/CYSC 2/10 via IPA (16.7%) miscible? | Yes | Yes | Yes | Yes | Yes | Yes | Yes |
| 13 Dcl/CYSC 3/10 via IPA (23.1%) miscible? | Yes | Yes | Yes | Yes | Yes | Yes | Yes |
| | Example No. | | | | | | |
| | 8I | 9I | 10I | 11I | 12I | 13I | 14I |
| 14 Dcl/CYSC 1/10 via melt (9.1%) uniform? | | | | | | | |

TABLE 1B-continued

| | Example No. | | | | | | |
|---|---|---|---|---|---|---|---|
| | 8J | 9J | 10J | 11J | 12J | 13J | 14J |
| 15 Risp/CYSC 1/10 via IPA (9.1%) uniform? | No | No | No | No | No | No | No |
| 16 DSC 1st heat Tp (° C.) | | | | | | | |
| 1st heat To (° C.) | | | | | | | |
| 2nd heat Tp (° C.) | | | | | | | |
| 2nd heat To (° C.) | | | | | | | |

| | Example No. | | | | | | |
|---|---|---|---|---|---|---|---|
| | 8K | 9K | 10K | 11K | 12K | 13K | 14K |
| 17 Risp/CYSC 2/10 via IPA (16.7%) uniform? | | | | | | | |

| | Example No. | | | | | | |
|---|---|---|---|---|---|---|---|
| | 8N | 9N | 10N | 11N | 12N | 13N | 14N |
| 18 Risp/CYSC 10/90 via melt (9.1%) uniform? | | | | | | | |

| | Example No. | | | | | | |
|---|---|---|---|---|---|---|---|
| | 8S | 9S | 10S | 11S | 12S | 13S | 14S |
| 19 Prav/CYSC 1/10 via IPA (9.1%) uniform? | Yes | Yes | Yes | Yes | Yes | Yes | Yes |
| 20 DSC 1st heat Tp (° C.) | 47.68 | 47.89 | 47.18 | 52.65 | 52.75 | 48.27 | 50.61 |
| 1st heat To (° C.) | 39.15 | 42.52 | 35.17 | 34.04 | 37.26 | 37.68 | 46.22 |
| 2nd heat Tp (° C.) | 44.41 | 44.65 | 44.20 | 51.16 | 53.17 | 45.46 | 47.59 |
| 2nd heat To (° C.) | 32.24 | 35.37 | 32.65 | 38.06 | 36.46 | 35.98 | 35.63 |

| | Example No. | | | | | | |
|---|---|---|---|---|---|---|---|
| | 8T | 9T | 10T | 11T | 12T | 13T | 14T |
| 21 Dexa/CYSC 1/10 via IPA (9.1%) uniform? | No | No | No | No | No | No | No |
| 22 DSC 1st heat Tp (° C.) | | | | | | | |
| 1st heat To (° C.) | | | | | | | |
| 2nd heat Tp (° C.) | | | | | | | |
| 2nd heat To (° C.) | | | | | | | |
| 23 Dexa/CYSC 1/10 via melt (9.1%) uniform? | | | Yes | | | | |
| 24 DSC 1st heat Tp (° C.) | | | 44.39 | | | | |
| 1st heat To (° C.) | | | 41.79 | | | | |
| 2nd heat Tp (° C.) | | | 39.77 | | | | |
| 2nd heat To (° C.) | | | 32.70 | | | | |

| | Example No. | | | | | | |
|---|---|---|---|---|---|---|---|
| | 8W | 9W | 10W | 11W | 12W | 13W | 14W |
| 25 Tacro/CYSC 1/10 via IPA (9.1%) uniform? | Yes | Yes | Yes | Yes | Yes | Yes | Yes |
| 26 DSC 1st heat Tp (° C.) | 50.20 | 47.85 | 44.69 | 48.22 | 42.87 | 46.89 | 49.49 |
| 1st heat To (° C.) | 44.92 | 45.53 | 42.20 | 45.47 | 50.25 | 42.91 | 42.32 |
| 2nd heat Tp (° C.) | 45.35 | 42.56 | 39.35 | 34.61 | 40.92 | 43.70 | 46.33 |
| 2nd heat To (° C.) | 39.93 | 34.16 | 32.02 | 38.64 | 35.74 | 34.72 | 34.20 |

TABLE 1C

| | Example No. | | | | | |
|---|---|---|---|---|---|---|
| | 15A 326-6-1 | 16A 326-6-3 | 17A 326-9-1 | 18A 326-11-3 | 19A 327-42-2 | 20A 327-42-11 |
| 1 CYSC (molar ratio) | | | | | | |
| C18A | 4 | 4 | 4 | 4 | 1 | 4 |
| AA | | | | | 1 | 1 |
| PEG6-OH A | 1 | | | | | |
| PPG6-OH A | | 1 | | | | |
| PEG6MA | | | | | 1 | 1 |

TABLE 1C-continued

|   |   |   |   |   |   |   |
|---|---|---|---|---|---|---|
| 2-HEA |   |   | 1 |   |   |   |
| VP |   |   |   | 1 |   |   |
| HEMA |   |   |   |   | 1 | 1 |
| Acrylamide |   |   |   |   | 1 | 1 |
| 2 Mw | 3155 | 2419 | 3058 | 3183 | 806 | 4563 |
| 3 Mn | 1938 | 1568 | 2199 | 2318 | 464 | 3049 |
| 4 DSC |   |   |   |   |   |   |
| 1st heat Tp (° C.) | 47.82 | 44.94 | 49.32 | 46.64 | 43.15 | 47.78 |
| 1st heat To (° C.) | 44.17 | 41.46 | 46.05 | 44.71 | 37.60 | 41.39 |
| 2nd heat Tp (° C.) | 43.33 | 42.17 | 45.77 | 43.96 | 41.96 | 44.08 |
| 2nd heat To (° C.) | 37.68 | 35.27 | 42.05 | 40.02 | 38.64 | 38.8 |

|   | Example No. | | | | | |
|---|---|---|---|---|---|---|
|   | 15B | 16B | 17B | 18B | 19B | 20B |
| 5 Sol. in Miglyol (18.97) | Yes | Yes | Yes | Yes | No | Yes |
| EtOAc (21.02) | Yes | Yes | Yes | Yes | Yes | Yes |
| NMP (23.12) | Yes | Yes | Yes | Yes | Yes | Yes |
| $H_2O$ (48.00) | No | No | No | No | No | No |
| 6 Gel form'n in Miglyol | Yes | Yes | Yes | Yes | No | Yes |
| EtOAc | Yes | Yes | Yes | Yes | Yes | Yes |
| NMP | Yes | Yes | Yes | Yes | No | Yes |
| $H_2O$ | No | No | No | No | No | No |
| 7 Solubility parameter | 17.61 | 17.36 | 17.56 | 17.26 | 19.31 | 18.14 |

|   | Example No. | | | | | |
|---|---|---|---|---|---|---|
|   | 15C | 16C | 17C | 18C | 19C | 20C |
| 8 Dcl/CYSC 1/10 via IPA (9.1%) uniform? | Yes | No | No | No | Yes | Yes |
| 9 DSC 1st heat Tp (° C.) | 46.9 |   |   |   | 41.6 | 49.2 |
| 1st heat To (° C.) | 45.8 |   |   |   | 35.5 | 43.5 |
| 2nd heat Tp (° C.) | 43.6 |   |   |   | 41.1 | 44.1 |
| 2nd heat To (° C.) | 37.9 |   |   |   | 37.8 | 39.2 |

|   | Example No. | | | | | |
|---|---|---|---|---|---|---|
|   | 15D | 16D | 17D | 18D | 19D | 20D |
| 10 Dcl/CYSC/NMP 10/50/50 (9.1%) uniform gel? | No | No | No | No | Yes | Yes |

|   | Example No. | | | | | |
|---|---|---|---|---|---|---|
|   | 15E | 16E | 17E | 18E | 19E | 20E |
| 11 Dcl/CYSC/NMP 10/10/90 (9.1%) uniform gel? | No | No | No | No | No | Yes |

|   | Example No. | | | | | |
|---|---|---|---|---|---|---|
|   | 15F | 16F | 17F | 18F | 19F | 20F |
| 12 Dcl/CYSC/IPA 2/10/7 (16.7%) miscible? | Yes |   |   |   | Yes | Yes |
| 13 Dcl/CYSC/IPA 3/10/7 (23.1%) miscible? | No |   |   |   | Yes | Yes |

|   | Example No. | | | | | |
|---|---|---|---|---|---|---|
|   | 15 I | 16 I | 17 I | 18 I | 19 I | 20 I |
|   | 326-6-1 | 326-6-3 | 326-9-1 | 326-11-3 | 327-42-2 | 327-42-11 |
| 14 Dcl/CYSC 1/10 via melt (9.1%) uniform? |   | Yes | Yes | Yes |   |   |

|   | Example No. | | | | | |
|---|---|---|---|---|---|---|
|   | 15J | 16J | 17J | 18J | 19J | 20J |
| 15 Risp/CYSC 1/10 via IPA (9.1%) uniform? | No | No | No | No | Yes | Yes |
| 16 DSC 1st heat Tp (° C.) |   |   |   |   | 47.4 | 43.5 |
| 1st heat To (° C.) |   |   |   |   | 42.1 | 40.7 |
| 2nd heat Tp (° C.) |   |   |   |   | 43.6 | 42.2 |
| 2nd heat To (° C.) |   |   |   |   | 31.3 | 37.2 |

TABLE 1C-continued

| | Example No. | | | | | |
|---|---|---|---|---|---|---|
| | 15K | 16K | 17K | 18K | 19K | 20K |
| 17 Risp/CYSC 2/10 via IPA (16.7%) uniform? | | | | | No | No |

| | Example No. | | | | | |
|---|---|---|---|---|---|---|
| | 15N | 16N | 17N | 18N | 19N | 20N |
| 18 Risp/CYSC 10/90 via melt (9.1%) uniform? | | Yes | | Yes | | |

| | Example No. | | | | | |
|---|---|---|---|---|---|---|
| | 15S | 16S | 17S | 18S | 19S | 20S |
| 19 Prav/CYSC 1/10 via IPA (9.1%) uniform? | Yes | Yes | Yes | Yes | Yes | Yes |
| 20 DSC 1st heat Tp (° C.) | 50.66 | 46.13 | 50.32 | 49.73 | 48.37 | 50.34 |
| 1st heat To (° C.) | 40.36 | 34.90 | 41.09 | 43.52 | 45.45 | 45.36 |
| 2nd heat Tp (° C.) | 44.65 | 45.54 | 48.68 | 45.83 | 43.73 | 45.56 |
| 2nd heat To (° C.) | 37.10 | 33.33 | 41.58 | 40.91 | 39.77 | 39.39 |

| | Example No. | | | | | |
|---|---|---|---|---|---|---|
| | 15T | 16T | 17T | 18T | 19T | 20T |
| 21 Dexa/CYSC 1/10 via IPA (9.1%) uniform? | No | No | No | No | Yes | No |
| 22 DSC 1st heat Tp (° C.) | | | | | 46.91 | |
| 1st heat To (° C.) | | | | | 43.35 | |
| 2nd heat Tp (° C.) | | | | | 49.24 | |
| 2nd heat To (° C.) | | | | | 39.31 | |
| 23 Dexa/CYSC 1/10 via melt (9.1%) melt | | | Yes | Yes | | Yes |
| 24 DSC 1st heat Tp (° C.) | | | 48.99 | 48.41 | | 46.17 |
| 1st heat To (° C.) | | | 44.82 | 45.38 | | 42.67 |
| 2nd heat Tp (° C.) | | | 46.32 | 45.22 | | 44.31 |
| 2nd heat To (° C.) | | | 42.14 | 40.55 | | 37.44 |

| | Example No. | | | | | |
|---|---|---|---|---|---|---|
| | 15W | 16W | 17W | 18W | 19W | 20W |
| 25 Ttacro/CYSC 1/10 via IPA (9.1%) uniform? | Yes | Yes | Yes | Yes | Yes | Yes |
| 26 DSC 1st heat Tp (° C.) | 46.34 | 45.75 | 47.88 | 49.12 | 45.95 | 47.14 |
| 1st heat To (° C.) | 43.17 | 43.40 | 46.36 | 44.33 | 42.28 | 36.21 |
| 2nd heat Tp (° C.) | 43.74 | 43.09 | 45.36 | 44.97 | 42.49 | 43.84 |
| 2nd heat To (° C.) | 38.48 | 36.33 | 41.11 | 40.39 | 39.97 | 39.69 |

This table below sets out terms and abbreviations used in the Examples and elsewhere in this specification, and the meanings to be attributed to them. Solubility parameters given herein were calculated using methods described in D. W. Van Krevelen "Properties of Polymer", Elsevier, 1997, 200-214, especially 214, and are expressed in units of $J^{1/2}/cm^{3/2}$.

| Abbreviation | Meaning |
|---|---|
| Cx | a linear moiety containing x carbon atoms, optionally directly linked to each other. |
| CxA | an n-alkyl acrylate in which the n-alkyl group contains x carbon atoms, e.g. C16A is hexadecyl acrylate. |
| CxMA | an n-alkyl methacrylate in which the n-alkyl group contains x carbon atoms, e.g. C16MA is hexadecyl methacrylate. |
| (meth)-acrylate | an acrylate or methacrylate |
| (meth)-acrylic acid | acrylic acid or methacrylic acid |
| AA | Acrylic acid |
| MA | Methacrylic acid |
| MiBK | Methyl isobutyl ketone |
| AIBN | Azobisisobutyronitrile |
| DMAEA | dimethylaminoethyl acrylate |
| DMAEMA | dimethylaminoethyl methacrylate |
| PEG6A | $CH_2=CH-CO-O-(CH_2CH_2O)_6H$ |
| PEG6MA | $CH_2=C(CH_3)-CO-O-(CH_2CH_2O)_5CH_2CH_2OH$ |
| PEG6-OCH3MA | $CH_2=C(CH_3)-CO-O-(CH_2CH_2O)_5CH_2CH_2OCH_3$ |
| PEG9-OCH3MA | $CH_2=C(CH_3)-CO-O-(CH_2CH_2O)_8CH_2CH_2OCH_3$ |
| PEG12-OCH3MA | $CH_2=C(CH_3)-CO-O-(CH_2CH_2O)_{11}CH_2CH_2OCH_3$ |
| PEG23-OCH3MA | $CH_2=C(CH_3)-CO-O-(CH_2CH_2O)_{22}CH_2CH_2OCH_3$ |
| PEG25-OCH3MA | $CH_2=C(CH_3)-CO-O-(CH_2CH_2O)_{24}CH_2CH_2OCH_3$ |

-continued

| Abbreviation | Meaning |
| --- | --- |
| PEG46-OCH3MA | $CH_2=C(CH_3)-CO-O-(CH_2CH_2O)_{45}CH_2CH_2OCH_3$ |
| PPG6-OHMA | $CH_2=C(CH_3)-C)-O-(CH_2CH(CH_3)O)_6H$ |
| PEG25 C22 MA | $CH_2=C(CH_3)-C)-O-(CH_2CH(CH_3)O)_6C_{22}H_{45}$ |
| IPA | isopropyl alcohol |
| EtAc | ethyl acetate |
| NMP | N-methyl pyrrolidone |
| BMP | butyl-3-mercapto propionate |
| Miglyol | Miglyol 812, a triglyceride with a mixture of C8 and C10 |
| Triganox | Triganox 428 -- t-butyl peroxy-3,5,5-trimethyl hexanoate |
| Dexa | Dexamethasone, which has a solubility parameter of 20.85 (9-fluoro-11β,17,21-trihydroxy-16a-methylpregna-1,4-diene-3,20-dione) |
| Prav | Pravachol, which has a solubility parameter of 21.07, (3,5-dihydroxy-7-[6-hydroxy-2-methyl-8-(2-methylbutanoyloxy)-1,2,6,7,8,8a-hexahydronaphthalen-1-yl]-heptanoic acid) |
| Risp | Risperidone, which has a solubility parameter of 17.48, (4-[2-[4-(6-fluorobenzo[d]isoxazol-3-yl)-1-piperidyl]ethyl]-3-methyl-2,6-diazabicyclo[4.4.0]deca-1,3-dien-5-one) |
| Dcl | Diclofenac sodium, which has a solubility parameter of 23.4, (2-[2-(2,6-dichlorophenyl)-aminophenyl]ethanoic acid) |
| Tacro | Tacrolimus, which has a solubility parameter of 19.32, (3S-[3R*[E(1S*,3S*,4S*)], 4S*,5R*,8S*,9E,12R*,14R*,15S*, 16R*,18S*,19S*,26aR*]]-5,6,8,11,12,13,14, 15,16,17,18,19,24,25,26,26a-hexadecahydro-5, 19-dihydroxy-3-[2-(4-hydroxy-3-methoxycyclohexyl)-1-methylethenyl]-14,16-dimethoxy-4,10,12,18-tetramethyl-8-(2-propenyl)-15,19-epoxy-3H-pyrido[2,1-c][1,4] oxaazacyclotricosine-1,7,20,21(4H,23H)-tetrone, monohydrate) |
| Leu | Leuprolide, which has a solubility parameter of 21.03, (N-[1-[[1-[[1-[[1-[[1-[[5-(diamino-methylideneamino)-1-[2-(ethylcarbamoyl)pyrrolidin-1-yl]-1-oxo-pentan-2-yl]carbamoyl]-3-methyl-butyl]carbamoyl]-3-methyl-butyl]carbamoyl]-2-(4-hydroxyphenyl)ethyl]carbamoyl]-2-hydroxy-ethyl]carbamoyl]-2-(1H-indol-3-yl)ethyl]carbamoyl]-2-(3H-imidazol-4-yl)ethyl]-5-oxo-pyrrolidine-2-carboxamide) |

The CYSC polymers described in the Examples were prepared by solution polymerization of the monomers in IPA at about 80° C. for 3 hours under a nitrogen blanket with 0.1% AIBN. BMP (6%) was used to control the molecular weight under 10,000, e.g. around 5000. IPA was removed under reduced pressure at elevated temperature. At the end of the reduced pressure stage, the internal temperature reached 120-130° C. and, in all the examples except Example 3A, 0.5 g of Trigonox was added. The reaction was continued at 120-130° C. for at least 1 hr, followed by 1 hr under reduced pressure. In Example 7A, one of the components of the polymer was DMAEA quat, and the polymer was prepared by converting the amine polymer of Example 5A into the quaternary ammonium salt by reaction with dimethyl sulphate in MiBK at 1/1 molar ratio (50-55° C., 3 hours) followed by removal of MiBK under reduced pressure at elevated temperature. Similarly, the polymer of Example 8A, which contains DMAEMA quat, was prepared by converting the amine polymer of Example 6 into the quaternary ammonium salt.

Tables 1A, 1B and 1C summarize the preparation and testing of 20 CYSC polymers 1A-20A. The polymers were prepared by the procedure described above, using the monomers, and the molar amounts thereof, shown in line 1 of Tables 1A, 1B and 1C.

Lines 2, 3 and 4 in Tables 1A, 1B and 1C show the values of Mw and Mn, and the DSC test results, for each of the 20 polymers. Lines 5 and 6 show shows the behavior of the polymers in four solvents with various polarities at 10% loading at 70° C. and room temperature (RT) respectively. The solubility parameters of the solvents are shown in parentheses in the Table. A typical procedure was to weigh 0.5 g of polymer and 4.5 g solvent into a 20 ml vial, followed by heating in a 70° C. oven for 10 to 15 min. The mixture was shaken by hand while warm. Lines 5, 6 and 7 (Examples 1B-20B) show respectively (line 5) whether the polymer dissolved at 70° C., (line 6) whether a uniform gel was formed after cooling to room temperature, and (line 7) the calculated solubility parameters of the CYSC polymers.

Lines 8 and 9 (Examples 1C-20C) in Tables 1A, 1B and 1C show the results of mixing the polymers with diclofenac sodium (dcl). The mixtures were prepared at 9.1% drug loading by mixing dcl with the polymer in IPA at the ratio of dcl/polymer/IPA=1/10/35 at 70° C., followed by evaporation of IPA in a 70° C. oven. A dry mixture was obtained by removing residual IPA under reduced pressure at 70° C. As noted in line 8, the mixtures were uniform except when using the polymers of Examples 1A, 5A, 16A, 17A and 18A. Line 9 shows the results of DSC examination of the uniform mixtures. A typical release sample of each of these 15 uniform mixtures and other mixtures in subsequent examples was prepared as a thin flat disc in a 20 ml scintillation vial (28×61 mm=OD×H) by loading 0.5 gram of the drug/polymer mixture into the vial and warming to 60-70° C., allowing the mixture to flow and fuse together. This resulted, after cooling, in a solid thin disc with a smooth uniform surface.

Line 10 (Examples 1D-20D) shows the results of preparing gel mixtures containing dcl, CYSC polymer and NMP at 10/50/50. Eight of the polymers formed uniform gels at RT.

Line 11 (Examples 1E-20E) shows the results of preparing mixtures containing dcl (9.1%), CYSC polymer NMP at the ratio of 10/10/90. Six of the 20 polymers (8A, 11A, 12A, 13A, 14A and 20A) formed a uniform gel at RT. Examples 1D-20D and 1E-20E demonstrate the effect of NMP on release rate.

Lines 12 and 13 (Examples 1F-20F) show the results of using the 15 polymers which formed uniform mixtures in Examples 10 to 20C, to prepare compositions containing more than 10% of dcl using the same process as in Examples 10 to 20C. For 16.7% and 23.1% loading, mixtures of dcl/CYSC polymer/IPA in ratios of 2/10/70 and 3/10/100 respectively were prepared at 70° C. After IPA was removed, all the tested CYSC polymers were miscible with dcl at 16.7% and 12 of them at 23.1%. Polymers 6A, 7A and 15A were not miscible and did not yield uniform mixtures.

Examples 2F1-2F7

The polymer of Example 2A was used to produce uniform dry mixtures having loadings of up to 37.5% of dcl, using the same process as in Examples C1-C, as shown in Table F1 below.

TABLE F1

| Example | Dcl g | Ex 2A pol g | IPA g | % dcl on polymer | % dcl on composition |
| --- | --- | --- | --- | --- | --- |
| 1F | 0.15 | 3.0 | 5.25 | 5.0 | 4.8 |
| 2F | 0.30 | 3.0 | 10.50 | 10.0 | 9.1 |
| 3F | 0.60 | 3.0 | 21.00 | 20.0 | 16.7 |
| 4F | 0.90 | 3.0 | 31.50 | 30.0 | 23.1 |
| 5F | 1.20 | 3.0 | 42.00 | 40.0 | 28.6 |
| 6F | 1.50 | 3.0 | 52.50 | 50.0 | 33.3 |
| 7F | 1.80 | 3.0 | 63.00 | 60.0 | 37.5 |

Examples 1G-20G

Using the same process as in Examples 1C-20C, 4 mixtures were prepared by mixing dcl with polymers 2A and 3A, polymers 2A and 4A, polymers 2A and 19A, and polymers 2A and 20A, respectively, using the amounts (in grams) shown in Table G1. Dry mixtures G1, G2 and G4 were uniform.

TABLE G1

| Example | dcl | 2A | 3A | 4A | 19A | 20A | IPA |
|---------|-----|-----|-----|-----|-----|-----|------|
| 1G | 0.5 | 2.5 | 2.5 | | | | 17.5 |
| 2G | 0.5 | 2.5 | | 2.5 | | | 17.5 |
| 3G | 0.5 | 2.5 | | | 2.5 | | 17.5 |
| 4G | 0.5 | 2.5 | | | | 2.5 | 17.5 |

Examples 1H-20H

Table H1 summarizes the preparation and testing of 4 CYSC polymers 1H-4H. The polymers were prepared by the procedure described above, using the monomers, and the molar amounts thereof, shown in lines 1 of Table H1. The Mw, Mn and DSC characteristics of the polymers are shown in lines 2, 3 and 4 of Table H1.

Uniform mixtures of dcl with these polymers were prepared in the same manner as in Examples 1C-20C.

TABLE H1

| | | Example No. | | | |
|---|---|---|---|---|---|
| | | 1H 328-57-5 | 2H 328-57-8 | 3H 327-42-3 | 4H 327-42-12 |
| 1 | CYSC pol units (molar) | | | | |
| | C18A | | 0.3 | | |
| | C22A | 1 | 0.7 | 1 | 4 |
| | AA | 4 | 4 | 1 | 1 |
| | PEG6MA | | | 1 | 1 |
| | HEMA | | | 1 | 1 |
| | Acrylamide | | | 1 | 1 |
| 2 | Mw | 2976 | 12,645 | 711 | 4736 |
| 3 | Mn | 2140 | 7136 | 440 | 3115 |
| 4 | DSC | | | | |
| | $1^{st}$ heat Tp | 66.73 | 60.70 | 62.88 | 63.74 |
| | $1^{st}$ heat To | 57.49 | 49.10 | 59.24 | 59.97 |
| | $2^{nd}$ heat Tp | 63.40 | 57.18 | 61.59 | 61.20 |
| | $2^{nd}$ heat To | 57.44 | 50.13 | 59.56 | 55.14 |

Line 14 (Examples 1I-20I) of Tables 1A, 1B and 1C summarizes the preparation of uniform mixtures of dcl and each of the 5 polymers (1A, 5A, 16A, 17A and 18A) which did not yield uniform mixtures in Examples 1C-20C (in which IPA was used). Uniform 2-phase mixtures were prepared by mixing dcl into the molten polymer at the weight ratio of 1/10 at 50-70° C. using a homogenizer for 1 min. in a vial. During the cooling stage, the vial continued to rotate until the mixture in the vial was solidified.

Line 15 (Examples 1J-20J) of Tables 1A, 1B and 1C summarizes the preparation of mixtures of risp and the polymers of Examples 1A-20A by mixing risp, polymer and IPA at the ratio of risp/polymer/IPA of 1/10/40 at 70° C., followed by removing IPA in a 70° C. oven. The dry mixture was obtained by removing residual IPA under the reduced pressure at 70° C. Only 5 out of the mixtures were uniform. In the uniform mixtures, the polymers were 2A, 3A, 4A, 19A and 20A, all containing carboxylic acid moieties. Line 16 reports the DSC characteristics of the uniform mixtures.

Line 17 (Examples 1K-20K) of Tables 1A, 1B and 1C summarizes the preparation of mixtures of risp and the polymers of Examples 1A-20A. The mixtures contain 16.7% of risperidone and were prepared by mixing risperidone with each of 5 polymers (2A, 3A, 4A, 19A and 20A) in IPA at the ratio of risp/polymer/IPA=2/10/80 at 70° C., followed by removing IPA in a 70° C. oven. The final dry mixtures were obtained by removing residual IPA under reduced pressure at 70° C. Only polymer 3A yielded a uniform mixture at 16.7% loading. As summarized in Table K1 below, compositions containing polymer 3A and a wider range of risperidone loading were prepared using the same process as in Examples 1J-20J. All the resulting mixtures were uniform. When the loading was higher than 25%, the mixture was more viscous and a temperature higher than 70° C. was used to prepare the disk.

TABLE K1

| Example | Risperidone | Polymer | IPA | % drug on polymer | % drug in composition |
|---------|-------------|---------|-----|-------------------|----------------------|
| 1K | 0.25 | 5 | 10 | 5.0 | 4.8 |
| 2K | 0.5 | 5 | 20 | 10.0 | 9.1 |
| 3K | 1 | 5 | 40 | 20.0 | 16.7 |
| 4K | 1.5 | 5 | 60 | 30.0 | 23.1 |
| 5K | 2 | 5 | 80 | 40.0 | 28.6 |
| 6K | 2.5 | 5 | 100 | 50.0 | 33.3 |
| 7K | 3 | 5 | 120 | 60.0 | 37.5 |

Examples 1L-4L

Using the same process as in Examples 1J-20J, 4 mixtures were prepared by mixing risp with polymers 2A and 3A, polymers 2A and 4A, polymers 2A and 19A, and polymers 2A and 20A, respectively, using the amounts (in grams) shown in Table L1. Dry mixtures L1, L2 and L4 were uniform. The dry mixture L3 was not uniform.

TABLE L1

| Example | Risp | Polymer 2A | Polymer 3A | Polymer 4A | Polymer 19A | Polymer 20A | IPA |
|---------|------|------------|------------|------------|-------------|-------------|-----|
| 1L | 0.5 | 2.5 | 2.5 | | | | 20 |
| 2L | 0.5 | 2.5 | | 2.5 | | | 20. |
| 3L | 0.5 | 2.5 | | | 2.5 | | 20 |
| 4L | 0.5 | 2.5 | | | | 2.5 | 20 |

Examples 1M-20M

Uniform mixtures of risperidone at 9.1% loading with polymers 1H, 2H, 3H and 4H were prepared in the same manner as in Examples 1J-20J.

Line 18 (Examples 1N-20N) of Tables 1A, 1B and 1C summarizes the preparation of uniform two-phase mixtures of risp and each of four polymers (1A, 5A, 16A and 18A) by mixing risperidone powder (0.5 g) into the molten polymer (5 g) at 50-70° C. using a homogenizer for 1 min in a vial. During the cooling stage, the vial continued to rotate until the mixture in the vial was solidified. Since risperidone was not miscible with these 4 polymers, it became uniformly distributed in the CYSC polymer as a discrete phase.

Examples 1 O-2 O

Five mixtures (2J, 3J, 4J, 19J and 20J) from Example 1J-20J were subjected to a hand grinding process to generate powder, and then passed through a 450 micron filter screen. Mixture 19J was sticky and agglomerated. Test articles for the release of risperidone from these particles were prepared by confining 0.5 gram of powder in a wine-bottle-shaped wire mesh (200×200 wires per linear inch—an opening of about 75 micron). The resulting article was then placed in the bottom of a 20 ml vial, ready for a release test.

Examples 1P-20P

Uniform mixture 2J from Examples 1J-20J was prepared as a thin flat disc in a 20 ml scintillation vial (28×61 mm=OD×H) by loading 0.05 gram of mixture at the bottom and warming in a 70° C. oven so that the mixture flowed and fused together, resulting in, after cooling, a very thin disc with a uniform flat surface. Such a thin disk was prepared to speed up the risperidone release as well as probe the effect of temperature triggering on release rate. Once the temperature triggering conditions were established, 0.5 g scale discs were prepared using the same methods in Examples 1J-20J and the dynamic temperature triggered release tests were performed using the conditions established in Examples 1P-20P Example 20Q A uniform two-phase mixture was obtained by mixing Polymer 20A with Bovine serum albumin (BSA, Fraction V, 99% from Aldrich, 66,000 Daltons). The BSA was mixed into the molten polymer at 50-70° C. using a homogenizer for one minute in a vial. During the cooling stage, the vial continued to rotate until the mixture in the vial was solid. Since BSA was not miscible with polymer 20A at the molecular level, it became uniformly distributed in the CYSC polymer as discrete phase.

Example 20R

The procedure of Example 20Q was followed, but replacing the BSA by Leuprorelin powder, which, like BSA, was not miscible with the polymer at the molecular level and was uniformly distributed in the CYSC polymer as a discrete phase.

Lines 19 and 20 (Examples 1S-20S) of Tables 1A, 1B and 1C summarize the preparation of mixtures of pravastatin sodium (9.1%) and the polymers of Examples 1A-20A, using the same method as in Examples 1J-20J. There was no phase separation in any of the mixtures. The DSC characteristics of the mixtures are shown in line 20.

Lines 21 and 22 (Examples 1T-20T) of Tables 1A, 1B and 1C summarize the preparation of mixtures of dexamethasone (9.1%) and the polymers of Examples 1A-20A, using the same method as in Examples 1J-20J. Only the mixtures containing polymers 3A and 19A showed no phase separation in any of the mixtures. The DSC characteristics of those mixtures are shown in line 22.

Lines 23 and 24 (Examples 1T-20T) of Tables 1A, 1B and 1C summarize the preparation of mixtures containing dexamethasone (9.1%). Using the same method as in Examples 1N-20N, uniform two-phase mixtures were prepared by mixing each of polymers 2A, 4A, 7A, 10A, 17A, 18A and 20A with dexamethasone powder. The dexamethasone was added to the molten polymer at 50-70° C. at a wt ratio of 1/10 using a homogenizer for 1 min. in a vial. During the cooling stage, the vial continued to rotate until the mixture in the vial was solidified. Since dexamethasone was not miscible with these 7 polymers at the molecular level, it became uniformly distributed in the CYSC polymer as discrete phase. Line 24 shows the DSC characteristics of the mixtures.

Examples 2U, 3U, 4U and 20U

Polymers 2U, 3U, 4U and 20U contain the same ingredients as polymers 2A, 3A, 4A and 20A respectively and were prepared in the same manner except for additional post treatment to remove residual monomers. For polymers 2U and 4U, an additional 0.25% AIBN was used before IPA was removed, followed by 2 washes with methanol. For polymer 4U, additional 0.25% AIBN, 0.5% L575 and 0.5% T42S was used to reduce the residual monomer. For polymer 20U, an additional 0.25% AIBN was used before IPA was removed, followed by 2 washes with DI water. The Mw, Mn and the DSC characteristics of the polymers are in Table U1.

TABLE U1

| Example | CYSC | Reference | Average (Mw) | Average (Mn) | First Heat (° C.) Tp | First Heat (° C.) To | Second Heat (° C.) Tp | Second Heat (° C.) To |
|---|---|---|---|---|---|---|---|---|
| 2U | 332-129 | purified 2A | 3,481 | 3,093 | 45.82 | 43.34 | 42.67 | 33.99 |
| 3U | 332-137 | purified 3A | 2,865 | 2,571 | 50.00 | 46.79 | 47.40 | 43.42 |
| 4U | 332-128 | purified 4A | 5,503 | 4,583 | 47.26 | 43.53 | 43.70 | 36.50 |
| 20U | 332-130 | purified 20A | 16,605 | 5,391 | 41.94 | 34.95 | 37.34 | 30.64 |

Examples 2V, 3V, 4V and 20V

Using the method described in Examples 1J-20J, polymers 2U, 3U, 4U and 20U were converted into cylindrical articles (diameter 6 mm, length 20 mm) containing 9.1% risperidone. The articles were sterilized by cobalt radiation at greater than 25 KGy.

Lines 25 and 26 (Examples 1W-20W) of Tables 1A, 1B and 1C summarize the preparation of mixtures of Tacrolimus (9.1%) and the polymers of Examples 1A-20A. The mixtures were prepared by mixing tacrolimus with the polymer in IPA at a ratio of 1/10/40 at 50-70° C., followed by removal of IPA in a 70° C. oven. The final dry mixture was obtained by removing residual IPA under reduced pressure at 70° C. All the dry mixtures were uniform. Line 26 shows the DSC characteristics of the dry mixtures.

The invention claimed is:

1. A method for making a drug formulation comprising a polymer and a drug which is uniformly distributed in the polymer, the polymer being a crystalline side chain (CYSC) polymer which:
   (A) comprises a plurality of repeating units having the formula:

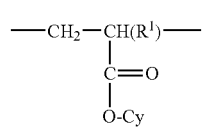

(1)

where R' is hydrogen or methyl, and
Cy is a moiety comprising an n-alkyl moiety containing 18-24 carbon atoms;
(B) has a crystalline melting temperature (Tp) of at least 40° C., an onset-of-melting temperature (To) such that Tp−To is less than $Tp^{0.7}$, and a heat of fusion of at least 5 J/g;

(C) has a number average molecular weight (Mn) less than 10,000;
(D) is a random copolymer comprising two or more randomly polymerized monomers; and
(E) is not cross-linked;
wherein the polymer comprises an alkylated hyaluronic acid or hydrolysed hyaluronic acid polymer structure;
the method comprising the steps of (1) distributing the drug in the polymer by mixing the drug with the polymer while the polymer is at a temperature above its crystalline melting temperature, and (2) cooling the mixture.

2. The method of claim 1 wherein the step (1) is carried out at a temperature of less than about 60° C., and the drug is a drug which is damaged by exposure to a temperature above about 60° C.

3. The method of claim 1 wherein the CYSC polymer has a Tp of between 40° C. and 60° C.

4. The method of claim 1 wherein Cy comprises an n-alkyl moiety containing 18 carbon atoms or an n-alkyl moiety containing 22 carbon atoms.

5. The method of claim 1 wherein the weight of the drug is at least 5% of the total weight of the formulation.

6. The method of claim 1 wherein the drug is selected from the group consisting of at least one of the following: anti-pain medications, anti-psychotics, neurotransmitter agonists, neurotransmitter antagonists, anti-inflammatories, hormones, anti-osteoporosis drugs, anti-angeogenics, cytotoxic agents, chemotherapeutics and contraceptives.

7. The method of claim 1 wherein the drug is an antipsychotic drug.

8. The method of claim 7 wherein the drug is selected from the group consisting of at least one of the following compounds: compounds containing functional groups of benzisoxazole and/or piperidine, olanzapine, fluphenazine maleate, chlorpromazine, chlorpromazine hibenzoate, sulpiride, carpipramine hydrochloride, carpipramine maleate, clocapramine hydrochloride, mosapramine hydrochloride, clozapine, oranzapine, sertindole, or an SSRI.

9. The method of claim 7 wherein the drug is Risperidone.

10. The method of claim 1 wherein the drug is Diclofenac.

11. The method of claim 1 wherein the drug comprises a protein or a polypeptide.

12. The method of claim 1 wherein the product of step (2) is formed into a shaped solid suitable for introduction by a trocar into a subject under the skin or intramuscularly, wherein the product is a microparticle from 1 to 125 microns in size.

13. The method of claim 12 wherein the drug is an antipsychotic drug.

14. The method of claim 12 wherein the shaped solid, having been implanted either subcutaneously or intramuscularly into a subject, releases the drug with a profile selected from the group consisting of: (i) release of drug no greater than 20 milligrams per day averaged over any 24 hour period during the first 168 hours of elution; (ii) release of drug continuously between 0.1 milligram and 20 milligrams per day over a period of at least 30 days; (iii) release of drug between 0.1 milligram and 20 milligrams per day, averaged over any 24 hour period during a period from 12 hours to 168 hours following inception of elution; and (iv) release of no more than 20% by weight of total drug loaded into the formulation over any period of 24 hours.

15. The method of claim 1 wherein the drug is a small molecule drug, a polypeptide drug or a protein drug; the product of step (2) is administered orally to a subject as a controlled-release pharmaceutical formulation, and thereafter releases a therapeutic dose of the drug from the formulation within the gastrointestinal tract only after the formulation had passed through the acid environment of the stomach into the small intestine, large intestine or colon.

16. The method of claim 15 wherein a therapeutic dose of the drug is released from the formulation within the alkaline environment of the small intestine and not within the acidic environment of the stomach.

17. The method of claim 1 wherein the weight of the drug is at least 15% of the total weight of the formulation.

18. The method of claim 1 wherein step (1) is carried out in the absence of a solvent.

19. The method of claim 1 wherein step (1) is carried out in the absence of a solvent, and the product of step (2) is formed into a shaped solid implant suitable for introduction by a trocar into a subject under the skin or intramuscularly.

20. The method of claim 1 wherein step (2) comprises dispersing the mixture comprising the drug and molten polymer into cold water.

21. The method of claim 1 wherein the product of step (2) is formulated as a formulation suitable for oral delivery.

22. The method of claim 1 wherein the drug is a small molecule drug and the product of step (2) is formulated as a formulation suitable for oral delivery.

23. The method of claim 1 wherein the drug is a protein drug or a polypeptide drug and the product of step (2) is formulated as a formulation suitable for oral delivery.

24. The method of claim 1 wherein the drug is interferon.

25. The method of claim 1 wherein the Cy moiety contains a polyoxyalkylene moiety.

26. A method of making a drug formulation comprising a polymer and a drug distributed in the polymer, the polymer being a crystalline side chain (CYSC) polymer which:
(A) has a backbone which comprises
(A1) a plurality of repeating units having the formula:

where $R^1$ is hydrogen or methyl, and
Cy is a moiety comprising an n-alkyl moiety containing 18-24 carbon atoms, and
(A2) a plurality of repeating units having the formula.

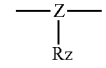

where Z is a moiety which forms part of the polymer backbone, and
Rz is a moiety which (i) does not contain a Cy moiety, and (ii) is a nitrogen-containing side chain, an oxygen-containing side chain, a fluorine-containing side chain, a phosphorus-containing side chain, a silicon-containing side chain or a ligand group which binds to target receptor sites;
(B) has a crystalline melting temperature (Tp) of at least 40° C., an onset-of-melting temperature (To) such that Tp−To is less than $Tp^{0.7}$, and a heat of fusion of at least 5 J/g;
(C) has a number average molecular weight (Mn) less than 10,000;

(D) is a random copolymer comprising two or more randomly polymerized monomers not a thermoplastic elastomer, is not a block copolymer and is not a graft copolymer; and (E) is not cross-linked;

wherein the polymer comprises an alkyl glucoside;

the method comprising the steps of (1) distributing the drug in the polymer by mixing the drug with the polymer while the polymer is at a temperature above its crystalline-melting temperature, and (2) cooling the mixture.

27. The method of claim 26 wherein step (1) is carried out at a temperature of less than about 60° C., and the drug is a drug which is damaged by exposure to a temperature above about 60° C.

28. The method of claim 26 wherein the CYSC polymer has a Tp of between 40° C. and 60° C.

29. The method of claim 26 wherein Cy comprises an n-alkyl moiety containing 18 carbon atoms or an n-alkyl moiety containing 22 carbon atoms.

30. The method of claim 26 wherein the CYSC polymer comprises alkylated carbohydrates, sugars, or starches.

31. The method of claim 26 wherein the CYSC polymer comprises carbohydrates, sugars, or starches esterified with crystalline fatty acids.

32. The method of claim 26 wherein the weight of the drug is at least 15% of the total weight of the formulation.

33. The method of claim 26 wherein step (1) is carried out in the absence of a solvent.

34. The method of claim 26 wherein step (1) is carried out in the absence of a solvent, and the product of step (2) is formed into a shaped solid implant in the form of a tablet, pill or capsule suitable for introduction into a subject under the skin or intramuscularly.

35. The method of claim 26 wherein step (2) comprises dispersing the mixture comprising the drug and molten polymer into cold water.

36. The method of claim 26 wherein the product of step (2) is formulated as a formulation suitable for oral delivery.

37. The method of claim 26 wherein the drug is a small molecule drug and the product of step (2) is formulated as a formulation suitable for oral delivery.

38. The method of claim 26 wherein the drug is a protein drug or a polypeptide drug and the product of step (2) is formulated as a formulation suitable for oral delivery.

39. The method of claim 26 wherein the drug is Risperidone.

40. The method of claim 26 wherein the drug is Diclofenac.

41. The method of claim 26 wherein the drug is a protein or polypeptide.

42. The method of claim 26 wherein the drug is interferon.

43. The method of claim 26 wherein the drug is a protein or polypeptide and the repeating units of the formula —Z(Rz)- contain cationic or anionic groups which associate ionically or through hydrogen bonding with carboxyl or amide groups of the protein or polypeptide.

44. The method of claim 1 wherein the mixture is shaped into a solid shape selected from rods, ovals and tablets.

45. The method of claim 44 wherein the mixture is shaped while it is molten.

46. The method of claim 44 wherein the mixture is shaped after it has solidified.

47. The method of claim 26 wherein the mixture is shaped into a solid shape selected from rods, ovals and tablets.

48. The method of claim 47 wherein the mixture is shaped while it is molten.

49. The method of claim 47 wherein the mixture is shaped after it has solidified.

* * * * *